US009701738B2

(12) United States Patent
McAdow et al.

(10) Patent No.: US 9,701,738 B2
(45) Date of Patent: Jul. 11, 2017

(54) **COMPOSITIONS AND METHODS RELATED TO ANTIBODIES THAT NEUTRALIZE COAGULASE ACTIVITY DURING *STAPHYLOCOCCUS AUREUS* DISEASE**

(71) Applicant: The University of Chicago, Chicago, IL (US)

(72) Inventors: Molly McAdow, Chicago, IL (US); Carla Emolo, Chicago, IL (US); Dominique Missiakas, Chicago, IL (US); Olaf Schneewind, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 14/397,049

(22) PCT Filed: Mar. 15, 2013

(86) PCT No.: PCT/US2013/031927
§ 371 (c)(1),
(2) Date: Oct. 24, 2014

(87) PCT Pub. No.: WO2013/162751
PCT Pub. Date: Oct. 31, 2013

(65) Prior Publication Data
US 2015/0368322 A1    Dec. 24, 2015

Related U.S. Application Data

(60) Provisional application No. 61/638,797, filed on Apr. 26, 2012.

(51) Int. Cl.
*A61K 39/395* (2006.01)
*C07K 16/00* (2006.01)
*C07K 16/12* (2006.01)
*A61K 38/00* (2006.01)

(52) U.S. Cl.
CPC .......... *C07K 16/1271* (2013.01); *A61K 38/00* (2013.01); *C07K 2317/24* (2013.01); *C07K 2317/33* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,648,240 | A  | 7/1997  | Hook et al. ............... 435/69.3 |
| 5,801,234 | A  | 9/1998  | Hodgson et al. ........... 536/23.7 |
| 5,840,846 | A  | 11/1998 | Hook et al. ............... 530/350 |
| 6,008,341 | A  | 12/1999 | Foster et al. .............. 536/23.7 |
| 6,288,214 | B1 | 9/2001  | Hook et al. .............. 530/387.1 |
| 7,875,280 | B2 | 1/2011  | Schneewind et al. |
| 8,758,765 | B2 | 6/2014  | Missiakas et al. |
| 8,808,699 | B2 | 8/2014  | Schneewind et al. |
| 8,821,894 | B2 | 9/2014  | Schneewind et al. |
| 8,840,906 | B2 | 9/2014  | Bubeck-Wardenburg et al. |
| 8,945,588 | B2 | 2/2015  | Schneewind et al. |
| 2002/0169288 | A1 | 11/2002 | Hook et al. .............. 530/350 |
| 2010/0183623 | A1 | 7/2010  | Patti et al. .............. 424/150.1 |
| 2011/0059085 | A1 | 3/2011  | Kim ..................... 424/133.1 |

FOREIGN PATENT DOCUMENTS

| WO | WO 98/57994   | 12/1998 |
| WO | WO 00/02523   | 1/2000  |
| WO | WO 00/12132   | 3/2000  |
| WO | WO 00/12689   | 3/2000  |
| WO | WO 00/15238   | 3/2000  |
| WO | WO 01/60852   | 8/2001  |
| WO | WO 2006/032472 | 3/2006 |
| WO | WO 2006/032475 | 3/2006 |
| WO | WO 2006/032500 | 3/2006 |
| WO | WO 2007/113222 | 10/2007 |
| WO | WO 2007/113223 | 10/2007 |
| WO | WO 2011/005341 | 1/2011  |
| WO | WO 2011127032 | 10/2011 |

OTHER PUBLICATIONS

Rudikoff et al (Proc Natl Acad Sci USA 1982 vol. 79 p. 1979).*
MacCallum et al. J. Mol. Biol. (1996) 262,732-745.*
Pascalis et al. The Journal of Immunology (2002) 169, 3076-3084.*
Casset et al. (2003) BBRC 307, 198-205.*
Vajdos et al. (2002) 320, 415-428.*
Chen et al. J. Mol. Bio. (1999) 293, 865-881.*
Wu et al. J. Mol. Biol. (1999) 294, 151-162.*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
(Campbell, Laboratory Techniques, vol. 13, 1984.*
Partial Supplementary European Search Report for EP 13781905.8, mailed Aug. 14, 2015.
U.S. Appl. No. 12/161,315, filed Feb. 19, 2009.
U.S. Appl. No. 13/122,793, filed Jun. 29, 2011.
U.S. Appl. No. 13/260,878, filed Dec. 6, 2011.
U.S. Appl. No. 13/742,155, filed Jan. 15, 2013.
U.S. Appl. No. 13/821,943, filed May 22, 2013.
U.S. Appl. No. 13/821,937, filed Jun. 3, 2013.
U.S. Appl. No. 14/238,811, filed Feb. 13, 2014.
U.S. Appl. No. 14/233,109, filed May 27, 2014.
U.S. Appl. No. 14/237,320, filed May 27, 2014.

(Continued)

*Primary Examiner* — Jennifer Graser
(74) *Attorney, Agent, or Firm* — Norton Rose Fulbright US LLP

(57) ABSTRACT

Embodiments concern methods and compositions for treating or preventing a bacterial infection, particularly infection by a *Staphylococcus* bacterium. Aspects include methods and compositions for providing a passive immune response against the bacteria, in certain embodiments, the methods and compositions involve an antibody that binds Coagulase (Coa).

13 Claims, 10 Drawing Sheets

(56) References Cited

OTHER PUBLICATIONS

U.S. Appl. No. 14/335,411, filed Jul. 18, 2014.
U.S. Appl. No. 14/466,514, filed Aug. 22, 2014.
U.S. Appl. No. 14/397,031, filed Oct. 24, 2014.
U.S. Appl. No. 14/397,049, filed Oct. 24, 2014
U.S. Appl. No. 14/422,756, filed Feb. 20, 2015.
DeDent et al., *Seminars in Immunopathology* 34(2):317-333, 2012.
Duthie et al., *J. Gen. Microbiol.* 6(1-2):95-107, 1952.
Bjerketorp J, Jacobsson K, Frykberg I. (2004) The von Willebrand factor-binding protein (vWbp) of *Staphylococcus aureus* is a coagulase. *FEMS Microbiology Letters* 234: 309-314.
Cheng et al., "Contribution of coagulases towards *Staphylococcus aureus* disease and protective immunity," *PLoS Pathogens* 6(8):e1001036, 2010.
Friedrich R, Panizzi P, Fuentes-Prior P, Richter K, Verhamme I, et al. (2003) Staphylocoagulase is a prototype for the mechanism of cofactor-induced zymogen activation. *Nature* 425: 535-539.
International Search Report and Written Opinion for PCT/US2013/031927, mailed Jun. 25, 2013.
McAdow M, Kim HK, Dedent AC, Hendrickx AP, Schneewind O, et al. (2011) Preventing *Staphylococcus aureus* sepsis through the inhibition of its agglutination in blood. *PLoS Pathogens* 7: e1002307.
McAdow M, Missiakas DM, Schneewind O (2012) *Staphylococcus aureus* Secretes Coagulase and von Willebrand Factor Binding Protein to Modify the Coagulation Cascade and Establish Host Infections. *Journal of Innate Immunity* 4: 141-148.
McAdow MD, A.C.; Emolo, C.; Cheng, A.G.; Kreiswirth, B.; Missiakas, D.M.; Schneewind, O. (2012) Coagulases as determinants of protective immune responses against *Staphylococcus aureus*. *Infect. Immun.* 80(1):3389-3398.
NCBI, "GenBank: AJ249487—*Staphylococcus epidermidis* aap gene for accumulation-associated protein, strain RP62A," <http://www.ncbi.nlm.nih.gov/nuccore/AJ249487>, 2000. Retrieved May 15, 2015.
NCBI, "GenBank: CAC80837—autolysin [*Staphylococcus aureus*]," <http://www.ncbi.nlm.nih.gov/protein/CAC80837>, 2005. Retrieved May 15, 2015.
NCBI, "GenBank: NP_372518—anti repressor [*Staphylococcus aureus* subsp. *aureus* Mu50]," <http://www.ncbi.nlm.nih.gov/protein/NP372518.1?report=genpept>, 2014. Retrieved May 15, 2015.
Palma M, Shannon O, Quezada HC, Berg A, Flock JI (2001) Extracellular fibrinogen-binding protein, Efb, from *Staphylococcus aureus* blocks platelet aggregation due to its binding to the alpha-chain. *The Journal of Biological Chemistry* 276: 31691-31697.
Panizzi P, Friedrich R, Fuentes-Prior P, Richter K, Bock PE, et al. (2006) Fibrinogen substrate recognition by staphylocoagulase. (pro)thrombin complexes. *The Journal of Biological Chemistry* 281: 1179-1187.
Phonimdaeng P, O'Reilly M, Nowlan P, Bramley AJ, Foster TJ (1990) The coagulase of *Staphylococcus aureus* 8325-4. Sequence analysis and virulence of site-specific coagulase-deficient mutants. *Molecular Microbiology* 4: 393-404.
Watanabe S, Ito T, Sasaki T, Li S, Uchiyama I, et al. (2009) Genetic diversity of staphylocoagulase genes (coa): insight into the evolution of variable chromosomal virulence factors in *Staphylococcus aureus*. *PLoS One* 4: e5714.
Watanabe S, Ito T, Takeuchi F, Endo M, Okuno E, et al. (2005) Structural comparison of ten serotypes of staphylocoagulases in *Staphylococcus aureus*. *Journal of Bacteriology* 187(11): 3698-3707.

* cited by examiner

FIG. 8A

Alignment of Coa from five S. aureus strains
```
USA300_Coa    ATGAAAAAGCAAATAATTTCGCTAGGCGCATTAGCAGTTGCATCTAGCTTATTTACATGG 60
N315_Coa      ATGAAAAAGCAAATAATTTCGCTAGGCGCATTAGCAGTTGCATCTAGCTTATTTACATGG 60
MRSA252_Coa   ATGAAAAAGCAAATAATTTCGCTAGGCGCATTAGCAGTTGCATCTAGCTTATTTACATGG 60
MW2_Coa       ATGAAAAAGCAAATAATTTCGCTAGGCGCATTAGCAGTTGCATCTAGCTTATTTACATGG 60
WIS_Coa       ------------------------------------------------------------

USA300_Coa    GATAACAAAGCAGATGCGATAGTAACAAAGGATTATAGTGGGAAATCACAAGTTAATGCT 120
N315_Coa      GATAACAAAGCAGATGCGATAGTAACAAAGGATTATAGTAAAGAATCAAGAGTGAATGAG 120
MRSA252_Coa   GATAACAAAGCAGATGCGATAGTAACTAAAGATTATAGTAAAGAATCAAGAGTGAATGAG 120
MW2_Coa       GATAACAAAGCAGATGCGATAGTAACAAAGGATTATAGTGGGAAATCACAAGTTAATGCT 120
WIS_Coa       -----------------ATAGTAACAAAGGATTATAGTGGGAAATCACAAGTTAATGCT 42
                               ******** ** ********  *****  *** ****

USA300_Coa    GGGAGTAAAAATGGGAC-ATTAAT---AGATAGCAGATATTTAAATTCAGCTCTATATTA 176
N315_Coa      AAAAGTAAAAAGGGAGCTACTGTTTC-AGATTATTACTATTGGAAAATAATT---GATAG 176
MRSA252_Coa   AACAGTAAAATACGATAC-ACCAATTCCAGATTG---GTATCTAGGTAGTATTTTAAACAG 176
MW2_Coa       GGGAGTAAAAATGGGAA-ACAAATTGCAGATGGATATTATTGGGGAATAATT---GAAAA 176
WIS_Coa       GGGAGTAAAAATGGGAA-ACAAATTGCAGATGGATATTATTGGGGAATAATT---* * 98
               ******  *  *       *   *   ****    ***          *    *

USA300_Coa    TTTGGAAGACTATATAATTTAT----GCTATAGGATTAACTAATAAATATGAATATGGAG 232
N315_Coa      TTTAGAGG----CACAATTTACTGGAGCAATAGACTTATTGGAAGATTATAAATATGGAG 232
MRSA252_Coa   ATTAGGGGATCAAATATACTAC----GCTAAGGAATTAACTAATAAATACGAATATGGTG 232
MW2_Coa       TCTAGAAAACCA---GTTTTAC-AATATTTTTCATTTACTGGATCAGCATAAATATGCAG 232
WIS_Coa       TCTAGAGAACCA---GTTTTAC-AATATTTTTCATTTATTGGATCAGCATAAATATGCAG 154
                * *           ***     *   *  *     ****** *

USA300_Coa    ATAATATTTATAAAGAAGCTAAAGATAGGTTGTTGGAAAAGGTATTAAGGGAAGATCAAT 292
N315_Coa      ATCCTATCTATAAAGAAGCGAAAGATAGATTGATGACAAGAGTATTAGGAGAAGACCAGT 292
MRSA252_Coa   AGAAAGAGTATAAGCAAGCGATAGATAAATTGATGACTAGAGTTTTGGGAGAAGATCATT 292
MW2_Coa       AAAAAGAATATAAAGATGCAGTAGATAAATTAAAAACTAGAGTTTTAGAGGAAGACCAAT 292
WIS_Coa       AAAAAGAATATAAAGATGCATTAGATAAATTAAAAACTAGAGTTTTAGAGGAAGACCAAT 214
              *    *****  * **  *****  **      *  ** ** ***** ** *

USA300_Coa    ATCTTTTGGAGAGAAAGAAATCTCAATATGAAGATTATAAACAATGGTATGCAAATTATA 352
N315_Coa      ATTTATTAAAGAAAAAGATTGATGAATATGAGCTTTATAAAAAGTGGTATAAAAGTT-CA 351
MRSA252_Coa   ATCTATTAGAAAAAAAGAAAGCACAATATGAAGCATACAAAAAATGGTTTGAAAAACATA 352
MW2_Coa       ACCTGCTAGAAAGAAAAAAAGAAAAATACGAAATTTATAAAGAACTATATAAAAAATACA 352
WIS_Coa       ACCTGCTAGAAAGAAAAAAAGAAAAATACGAAATTTATAAAGAACTATATAAAAAATACA 274
              * *   *  * ***  *     **** **  ** *** *     * *  **

USA300_Coa    AAAAAGAAAATCCTCGTACAGATTTAAAAATGGCTAATTTTCATAAATATAATTTAGAAG 412
N315_Coa      AATAAGACACT-------------AATATGCTTACTTTCCATAAATAATAATCTTTACA 397
MRSA252_Coa   AAAGTGAAAATCCACATTCTAGTTTAAAAAAGATTAAATTTGACGATTTTGATTTATATA 412
MW2_Coa       AAAAAGAGAATCCTAATACTCAAGTTAAAATGAAAGCATTTGATAAATACGATCTTGGCG 412
WIS_Coa       AAAAAGAGAATCCTAATACTCAGGTTAAAATGAAAGCATTTGATAAATACGATCTTGGCG 334
              **  **  *      *           ** *     **  * *    * ** *

USA300_Coa    AACTTTCGATGAAAGAATACAATGAACTACAGGATGCATTAAAGAGAGCACTGGATGATT 472
N315_Coa      ATTTAACAATGAATGAATATAACGATATATTTTAACTCTTTGAAAGATGCAGTTTATCAAT 457
MRSA252_Coa   GATTACGAAGAAAGAATACAATGAGTTACATCAATCATTAAAAGAAGCTGTTGATGAGT 472
MW2_Coa       ATTTAACTATGGAAGAATACAATGACTTATCAAAATTATTAACAAAAGCATTGGATAACT 472
WIS_Coa       ATTTAACTATGGAAGAATACAATGACTTATCAAAATTATTAACAAAAGCATTGGATAACT 394
                * *  *  **** ** **        *  **  *        ** *  ** ** *

USA300_Coa    TTCACAGAGAAGTTAAAGATATTAAGGATAAGAATTCAGACTTGAAAACTTTTAATGCAG 532
N315_Coa      TTAATAAAGAAGTTAAAGAAATAGAGCATAAAAATGTTGACTTGAAGCAGTTTGATAAAG 517
MRSA252_Coa   TTAATAGTGAAGTGAAAAATATTCAATCTAAACAAAAGGATTTATTACCTTATGATGAAG 532
MW2_Coa       TTAAGTTAGAAGTAAAGAAAATTGAATCAGAGAATCCAGATTTAAAACCATATTCTGAAA 532
WIS_Coa       TTAAGTTAGAAGTAAAGAAAATTGAATCAGAGAATCCAGATTTAAGACCATATTCTGAAA 454
              **  *    ****** **  ** **     * *    * **

USA300_Coa    CAGAAGAAGATAAAGCAACTAAGGAAGTATACGATCTCGTATCTGAAATTGATACATTAG 592
N315_Coa      ATGGAGAAGACAAGGCAACTAAAGAAGTTTATGACCTTGTTTCTGAAATTGATACATTAG 577
MRSA252_Coa   CAACTGAAAATCGAGTAACAAATGGAATATATGATTTTGTTTGCGAGATTGACACATTAT 592
MW2_Coa       GCGAAGAAAGAACAGCATATGGTAAAATAGATTCACTTGTTGATCAAGCATATAGTGTAT 592
WIS_Coa       GTGAAGAGAGAACAGCATATGGTAAAATAGATTCACTTGTTGATCAAGCATATAGTGTAT 514
                 * *  *     **   **    *     *    ***   *   ** ** **

USA300_Coa    TTGTATCATATTATGGTGATAAGGATTATGGGGAGCACGCGAAAGAGTTACGAGCAAAAC 652
N315_Coa      TTGTAACTTATTATGCTGATAAGGATTATGGGGAGCATGCGAAAGAGTTACGAGCAAAAC 637
MRSA252_Coa   ACGCAGCTATTTTTAATCATAGCCAATATGGTCATAATGCTAAAGAATTAAGAGCAAAGC 652
MW2_Coa       ATTTTGCCTACGTTACAGATGCACAACATAAAACAGAAGCATTAAATCTTAGGGCGAAAA 652
```

FIG. 8B

```
WIS_Coa         ATTTTGCCTACGTTACAGATGCTCAACATAAAACAGAAGCATTAAATCTTAGGGCAAAAA 574
                  * **   *   **    *    * **    * *  * ***  **

USA300_Coa      TGGACTTAATCCTTGGAGATACAGACAATCCACATAAAATTACAAATGAACGTATTAAAA 712
N315_Coa        TGGACTTAATCCTTGGAGATACAGACAATCCACATAAAATTACAAATGAGCGTATAAAAA 697
MRSA252_Coa     TAGATATAATTCTTGGTGATGCTAAAGATCCTGTTAGAATTACGAATGAAAGAATAAGAA 712
MW2_Coa         TTGATTTGATTTTAGGTGATGAAAAAGATCCAATTAGAGTTACGAATCAACGTACTGAAA 712
WIS_Coa         TAGATTTGATTTTAGGTGATGAAAAAGATCCAATTAGAGTGACGAATCAACGTACTGAAA 634
                 * **   *  **  * ** ***      *     **** ** * * *** ** * *  **

USA300_Coa      AAGAAATGATTGATGACTTAAATTCAATTATTGATGATTTCTTTATGGAAACTAAACA-A 771
N315_Coa        AAGAAATGATCGATGACTTAAATTCAATTATAGATGATTTCTTTATGGAGACTAAACA-A 756
MRSA252_Coa     AAGAAATGATGGATGATTTAAATTCTATTATTGATGATTTCTTTATGGATAC-AAACATG 771
MW2_Coa         AAGAAATGATTAAAGATTTAGAATCTATTATTGATGATTTCTTCATTGAAACCAAGTT-G 771
WIS_Coa         AAGAAATGATTAAAGATTTAGAATCTATTATTGATGATTTCTTCATTGAAACAAAGTT-G 693
                **********  *  ** ***  *  ** ***** ********* ** ** ** **

USA300_Coa      AATAGACCGAAATCTATAACGAAATATAATCCTACAACACATAACTATAAAACAAATAGT 831
N315_Coa        AATAGACCGAATTCTATAACAAAATATGATCCAACAAAACACAATTTTAAAGAGAAGAGT 816
MRSA252_Coa     AATAGACCATTAAACATAACTAAATTTAATCCGAATATTCATGACTATACTAATAAGCCT 831
MW2_Coa         AATAGACCTAAACACATTACTAGGTATGATGGAACTAAACATGATTACCA--------T 822
WIS_Coa         AATAGACCTCAACACATTACTAGATATGATGGAACTAAACATGATTACCA--------T 744
                ********             ** **  * * * **   * **   * *            *

USA300_Coa      GATAATAAACCTAATTTTGATAAATTAGTTGAAGAAACGAAAAAAGCAGTTAAAGAAGCA 891
N315_Coa        GAAAATAAACCTAATTTTGATAAATTAGTTGAAGAAACAAAAAAAGCAGTTAAAGAAGCA 876
MRSA252_Coa     GAAAATAGAGATAACTTCGATAAATTAGTCAAAGAAACAAGAGAAGCAATCGCAAACGCT 891
MW2_Coa         AAACATAAAGATGGATTTGATGCTCTAGTTAAAGAAACAAGAGAAGCGGTTGCAAAGGCT 882
WIS_Coa         AAACATAAAGATGGATTTGATGCTTTAGTTAAAGAAACAAGAGAAGCGGTTTCTAAGGCT 804
                 *  ***  *  *   ** ***    **** *******  *  ****       *  **

USA300_Coa      GATGATTCTTGGAAAAAGAAAACTGTCAAAAAATACGGAGAAACTGAAACAAAATCGCCA 951
N315_Coa        GACGAATCTTGGAAAAATAAAACTGTCAAAAAATACGAGGAAACTGTAACAAAATCTCCT 936
MRSA252_Coa     GACGAATCTTGGAAAACAAGAACCGTCAAAAATTACGGTGAATCTGAAACAAAATCTCCT 951
MW2_Coa         GACGAATCTTGGAAAAATAAAACTGTCAAAAAATACGAGGAAACTGTAACAAAATCTCCA 942
WIS_Coa         GACGAATCTTGGAAAACTAAAACTGTCAAAAAATACGGGGAAACTGAAACAAAATATCCT 864
                ** ** **********  *  *** ******** ****   ***  ***  ******* **

USA300_Coa      GTAGTAAAAGAAGAGAAGAAAGTTGAAGAACCTCAAGCACCTAAAGTTGATAACCAACAA 1011
N315_Coa        GTTGTAAAAGAAGAGAAGAAAGTTGAAGAACCTCAATTACCTAAAGTTGGAAACCAGCAA 996
MRSA252_Coa     GTTGTAAAAGAAGAGAAGAAAGTTGAAGAACCTCAATTACCTAAAGTTGGAAACCAGCAA 1011
MW2_Coa         GTTGTAAAAGAAGAGAAGAAAGTTGAAGAACCTCAATCACCTAAATTTGATAACCAACAA 1002
WIS_Coa         GTTGTAAAAGAAGAGAAGAAAGTTGAAGAACCTCAATCACCTAAAGTTTCTGAAAAAGTG 924
                ** *******************************   ******* *    *  *

USA300_Coa      GAGGTTAAAACTACGGCTGGTAAAGCTGAAGAAACAACACAACCAGTTGCACAACCATTA 1071
N315_Coa        GAGGTTAAAACTACGGCTGGTAAAGCTGAAGAAACAACACAACCAGTGGCACAGCCATTA 1056
MRSA252_Coa     GAGGATAAAATTACAGTTGGTACAACTGAAGAAGCACCATTACCAATTGCGCAACCACTA 1071
MW2_Coa         GAGGTTAAAATTACAGTTGATAAAGCTGAAGAAACAACAACCAGTGGCACAGCCATTA 1062
WIS_Coa         GATGTTCAGGAAACGGTTGGTACAACTGAAGAAGCACCATTACCAATTGCGCAACCACTA 984
                ** * *   ** * ** **  *  *  ********  **  **     *  ** ** **

USA300_Coa      GTTAAAATTCCACAGGGCACAATTACAGGTGAAATTGTAAAAGGTCCGGAATATCCAACG 1131
N315_Coa        GTAAAAATTCCACAAGAAACAATCTATGGTGAAACTGTAAAAGGTCCAGAATATCCAACG 1116
MRSA252_Coa     GTTAAAATTCCACAGGGCACAATTCAAGGTGAAATTGTAAAAGGTCCGGAATATCTAACG 1131
MW2_Coa         GTTAAAATTCCACAGGGCACAATTACAGGTGAAATTGTAAAAGGTCCAGATTATCCAACG 1122
WIS_Coa         GTTAAATTACCACAAATTGGGACTCAAGGCGAAATTGTAAAAGGTCCCGACTATCCAACT 1044
                ** ***  * *****        *   *** ***** ************  **** ***

USA300_Coa      ATGGAAAATAAAACGGTACAAGGTGAAATCGTTCAAGGTCCCGATTTTCTAACAATGGAA 1191
N315_Coa        ATGGAAAATAAAACGTTACAAGGTGAAATCGTTCAAGGTCCCGATTTTCTAACAATGGAA 1176
MRSA252_Coa     ATGGAAAATAAAACGTTACAAGGTGAAATCGTTCAAGGTCCAGATTTCCCAACAATGGAA 1191
MW2_Coa         ATGGAAAATAAAACGTTACAAGGTGAAATCGTTCAAGGTCCAGATTTCCCAACAATGGAA 1182
WIS_Coa         ATGGAAAATAAAACGTTACAAGGTGTAATTGTTCAAGGTCCAGATTTCCCAACAATGGAA 1104
                **************  ********  ** *  *********  ***** * *********

USA300_Coa      CAAAGCGGCCCATCATTAAGCAATAATTATACAAACCCA--------------------- 1230
N315_Coa        CAAAACAGACCATCTTTAAGCGATAATTATACTCAACCG--------------------- 1215
MRSA252_Coa     CAAAACAGACCATCTTTAAGCGATAATTATACTCAACCG--------------------- 1230
MW2_Coa         CAAAACAGACCATCTTTAAGCGATAATTATACTCAACCG--------------------- 1221
WIS_Coa         CAAAACAGACCATCTTTAAGTGACAATTATACACAACCATCTGTGACTTTACCGTCAATT 1164
                ****  * * **** *****  *  ******** ******

USA300_Coa      -----------CCGTTAACGAACCCTATTTTAGAAGGTCTTGAAGGTAGCTCATCTAAA 1278
N315_Coa        -----------ACGACACCGAACCCTATTTTAGAAGGTCTTGAAGGTAGCTCATCTAAA 1263
MRSA252_Coa     -----------ACGACACCGAACCCTATTTTAAAAGGTATTGAAGGAAACTCAACTAAA 1278
```

FIG. 8C

```
MW2_Coa      ------------ACGACACCGAACCCTATTTTAGAAGGTCTTGAAGGTAGCTCATCTAAA 1269
WIS_Coa      ACAGGTGAAAGTACACCAACGAACCCTATTTTAAAAGGTATTGAAGGAAACTCATCTAAA 1224
                         *  * **************  *****  *******  *  **** *****

USA300_Coa   CTTGAAATAAAACCACAAGGTACTGAATCAACGTTAAAAGGTACTCAAGGAGAATCAAGT 1338
N315_Coa     CTTGAAATAAAACCACAAGGTACTGAATCAACGTTGAAAGGTATTCAAGGAGAATCAAGT 1323
MRSA252_Coa  CTTGAAATAAAACCACAAGGTACTGAATCAACGTTAAAAGGTACTCAAGGAGAATCAAGT 1338
MW2_Coa      CTTGAAATAAAACCACAAGGTACTGAATCAACGTTAAAAGGTACTCAAGGAGAATCAAGT 1329
WIS_Coa      CTTGAAATAAAACCACAAGGTACTGAATCAACGTTGAAAGGTATTCAAGGAGAATCAAGT 1284
             ***********************************  ******* ***************

USA300_Coa   GATATTGAAGTTAAACCTCAAGCAACTGAAACAACAGAAGCTTCTCAATATGGTCCGAGA 1398
N315_Coa     GATATTGAAGTTAAACCTCAAGCAACTGAAACAACAGAAGCTTCTCAATATGGTCCGAGA 1383
MRSA252_Coa  GATATTGAAGTTAAACCTCAAGCAACTGAAACAACAGAAGCATCACATTATCCAGCGAGA 1398
MW2_Coa      GATATTGAAGTTAAACCTCAAGCATCTGAAACAACAGAAGCATCACATTATCCAGCAAGA 1389
WIS_Coa      GATATTGAAGTTAAACCTCAAGCAACTGAAACAACAGAAGCATCACATTATCCAGCGAGA 1344
             ***********************  **************** ** ** ***    * ***

USA300_Coa   CCGCAATTTAACAAAACACCTAAATATGTTAAATATAGAGATGCTGGTACAGGTATCCGT 1458
N315_Coa     CCGCAATTTAACAAAACACCTAAGTATGTGAAATATAGAGATGCTGGTACAGGTATCCGT 1443
MRSA252_Coa  CCTCAATTTAACAAAACACCTAAGTATGTGAAATATAGAGATGCTGGTACAGGTATCCGT 1458
MW2_Coa      CCTCAATTTAACAAAACACCTAAATATGTTAAATATAGAGATGCTGGTACAGGTATCCGT 1449
WIS_Coa      CCGCAATTTAACAAAACACCTAAATATGTGAAATATAGAGATGCTGGTACAGGTATTCGT 1404
             ** *******************  *****  **************************** ***

USA300_Coa   GAATACAACGATGGAACATTTGGATATGAAGCGAGACCAAGATTCAATAAGCCA------ 1512
N315_Coa     GAATACAACGATGGAACATTTGGATATGAAGCGAGACCAAGATTCAACAAGCCAAGTGAA 1503
MRSA252_Coa  GAATACAACGATGGAACATTTGGATATGAAGCGAGACCAAGATTCAACAAGCCAAG---- 1514
MW2_Coa      GAATACAACGATGGAACATTTGGATATGAAGCGAGACCAAGATTCAATAAGCCATCAGAA 1509
WIS_Coa      GAATACAACGATGGAACTTTTGGATATGAAGCGAGACCAAGATTCAACAAGCCATCAGAA 1464
             ***************** ****************************** ******

USA300_Coa   --------------------TCA------------------------------------- 1515
N315_Coa     ACAAATGCATACAACGTAACGACAAATCAAGATGGCACAGTATCATACGGAGCTCGCCCA 1563
MRSA252_Coa  --------------------C--------------------------------------- 1515
MW2_Coa      ACAAACGCATACAACGTAACGACAAATCAAGATGGCACAGTAACATATGGCGCTCGCCCA 1569
WIS_Coa      ACAAACGCATACAACGTAACGACAAATCAAGATGGCACAGTATCATATGGGGCTCGCCCA 1524
                                  *

USA300_Coa   -----------------GAAACAAATGCATATAACGTAACAACACATGCAAATGGTCAA 1557
N315_Coa     ACACAAAACAAGCCAAGTGAAACAAACGCATATAACGTAACAACACATGCAAATGGTCAA 1623
MRSA252_Coa  -----------------GAAACAAATGCATACAACGTAACGACAAATCAAGATGGCACA 1557
MW2_Coa      ACACAAAACAAACCAAGCAAAACAAATGCATACAACGTAACAACACATGCAAATGGTCAA 1629
WIS_Coa      ACACAAAACAAGCCAAGCAAAACAAATGCATATAACGTAACAACACATGCAAACGGCCAA 1584
                                *******  ***** ********  **  *  * **   *

USA300_Coa   GTATCATACGGAGCTCGTCCGACA------------------------------------ 1581
N315_Coa     GTATCATACGGTGCTCGCCCAACA------------------------------------ 1647
MRSA252_Coa  GTATCATATGGCGCTCGCCCGACA------------------------------------ 1581
MW2_Coa      GTATCATATGGCGCTCGCCCGACA------------------------------------ 1653
WIS_Coa      GTATCATATGGCGCTCGCCCCGACATACAACAAGCCAAGTGAAACAAATGCATACAACGTA 1644
             ******** ** ***** ** ***

USA300_Coa   -------------------------------------------CAAAACAAGCCAAGC 1596
N315_Coa     -------------------------------------------CAAAAAAGCCAAGC 1662
MRSA252_Coa  -------------------------------------------CAAAACAAGCCAAGC 1596
MW2_Coa      -------------------------------------------CAAAACAAGCCAAGC 1668
WIS_Coa      ACGACAAATCGAGATGGCACAGTATCATATGGCGCTCGCCCGACACAAAACAAGCCAAGC 1704
                                                        *****  *********

USA300_Coa   AAAACAAACGCATATAACGTAACAACACATGGAAACGGCCAAGTATCATATGGCGCTCGC 1656
N315_Coa     AAAACAAATGCATACAACGTAACAACACATGCAAATGGTCAAGTATCATATGGCGCTCGC 1722
MRSA252_Coa  GAAACAAACGCATATAACGTAACAACACATGCAAACGGCCAAGTATCATACGGAGCTCGT 1656
MW2_Coa      AAAACAAATGCATATAACGTAACAACACATGCAAATGGTCACAGTATCATACGGAGCTCGC 1728
WIS_Coa      GAAACGAATGCATATAACGTAACAACACACGGAAATGGCCAAGTATCATATGGCGCTCGT 1764
             ****  ** ******  ************   *  **  ***********  **  *****

USA300_Coa   CCAACACAAAACAAGCCAAGCAAAACAAATGCATACAACGTAACAACACATGCAAACGGT 1716
N315_Coa     CCGACACAAAAAAAGCCAAGCAAAACAAATGCATATAACGTAACAACACATGCAAATGGT 1782
MRSA252_Coa  CCGACACAAAACAAGCCAAGCGAAACGAACGCATATAACGTAACAACACATGCAAACGGT 1716
MW2_Coa      CCGACACAAAACAAGCCAAGCAAAACAAATGCATATAACGTAACAACACATGCAAACGGT 1788
WIS_Coa      CCGACACAAAAGAAGCCAAGCAAAACAAATGCATATAACGTAACAACACATGCAAACGGC 1824
             **  ********* ********  **  * **** ** ************* ***** **

USA300_Coa   CAAGTGTCATACGGAGCTCGCCCGACATACAAGAAGCCAAGTAAAACAAATGCATACAAT 1776
N315_Coa     CAAGTATCATACGGAGCTCGCCCCGACATACAAGAAGCCAAGCGAAACAAATGCATACAAC 1842
```

FIG. 8D

```
MRSA252_Coa    CAAGTGTCATACGGAGCTCGCCCAACACAAAACAAGCCAAGTAAAACAAATGCATACAAT 1776
MW2_Coa        CAAGTGTCATACGGAGCTCGCCCGACATACAAGAAGCCAAGTAAAACAAATGCATACAAT 1848
WIS_Coa        CAAGTATCATATGGCGCTCGTCCGACATACAACAAGCCAAGTAAAACAAATGCATACAAT 1884
               ***** ***** ** ***** ** *** * ** ******* ****************

USA300_Coa     GTAACAACACATGCA--------------------------------------------- 1791
N315_Coa       GTAACAACACATGCAAATGGTCAAGTATCATATGGCGCTCGCCCGACACAAAAAAAGCCA 1902
MRSA252_Coa    GTAACAACACATGCA--------------------------------------------- 1791
MW2_Coa        GTAACAACACATGCA--------------------------------------------- 1863
WIS_Coa        GTAACAACACATGCA--------------------------------------------- 1899
               ***************

USA300_Coa     ---------------------------------------GATGGTACTGCGACATATGGGCCT 1815
N315_Coa       AGCGAAACAAACGCATATAACGTAACAACACATGCAGATGGTACTGCGACATATGGGCCT 1962
MRSA252_Coa    ---------------------------------------GATGGTACTGCGACATATGGTCCT 1815
MW2_Coa        ---------------------------------------GATGGTACTGCGACATATGGGCCT 1887
WIS_Coa        ---------------------------------------GATGGTACTGCGACATATGGTCCT 1923
                                                       ******************** ***

USA300_Coa     AGAGTAACAAAATAA 1830
N315_Coa       AGAGTAACAAAATAA 1977
MRSA252_Coa    AGAGTAACAAAATAA 1830
MW2_Coa        AGAGTAACAAAATAA 1902
WIS_Coa        AGAGTAACAAAATAA 1938
               ***************
```

SEQUENCE LISTING

<160> NUMBER OF SEQ ID NOS: 61

<210> SEQ ID NO 1
<211> LENGTH: 1830
<212> TYPE: DNA
<213> ORGANISM: Staphylococcus aureus

<400> SEQUENCE: 1

```
atgaaaaagc aaataatttc gctaggcgca ttagcagttg catctagctt atttacatgg      60
gataacaaag cagatgcgat agtaacaaag gattatagtg ggaaatcaca agttaatgct     120
gggagtaaaa atgggacatt aatagatagc agatatttaa attcagctct atattatttg     180
gaagactata taatttatgc tataggatta actaataaat atgaatatgg agataatatt     240 tataagaag  ctaaagatag gttgttggaa aaggtattaa gggaagatca atatctttg      300 gagagaaaga aatctcaata tgaagattat aaacaatggt atgcaaatta taaaaagaa      360 aatcctcgta cagatttaaa aatggctaat tttcataaat ataatttaga agaactttcg     420
```

```
atgaaagaat acaatgaact acaggatgca ttaaagagag cactggatga ttttcacaga      480
gaagttaaag atattaagga taagaattca gacttgaaaa cttttaatgc agcagaagaa      540
gataaagcaa ctaaggaagt atacgatctc gtatctgaaa ttgatacatt agttgtatca      600
tattatggtg ataaggatta tggggagcac gcgaaagagt tacgagcaaa actggactta      660
atccttggag atacagacaa tccacataaa attacaaatg aacgtattaa aaagaaatg       720 attgatgact taaattcaat tattgatgat ttctttatgg aaactaaaca aaatagaccg      780
aaatctataa cgaaatataa tcctacaaca cataactata aaacaaatag tgataataaa      840
cctaattttg ataaattagt tgaagaaacg aaaaaagcag ttaaagaagc agatgattct      900
tggaaaaaga aaactgtcaa aaaatacgga gaaactgaaa caaaatcgcc agtagtaaaa      960
gaagagaaga aagttgaaga acctcaagca cctaaagttg ataaccaaca agaggttaaa      1020
actacggctg gtaaagctga agaaacaaca caaccagttg cacaaccatt agttaaaatt      1080
ccacagggca caattacagg tgaaattgta aaaggtccgg aatatccaac gatgaaaat       1140 aaaacggtac aaggtgaaat cgttcaaggt cccgattttc taacaatgga acaaagcggc      1200
ccatcattaa gcaataatta tacaaaccca ccgttaacga accctatttt agaaggtctt      1260
gaaggtagct catctaaact tgaaataaaa ccacaaggta ctgaatcaac gttaaaaggt      1320
actcaaggag aatcaagtga tattgaagtt aaacctcaag caactgaaac aacagaagct      1380
tctcaatatg gtccgagacc gcaatttaac aaaacaccta aatatgttaa atatagagat      1440
gctggtacag gtatccgtga atacaacgat ggaacatttg gatatgaagc gagaccaaga      1500
ttcaataagc catcagaaac aaatgcatat aacgtaacaa cacatgcaaa tggtcaagta      1560
tcatacggag ctcgtccgac acaaaacaag ccaagcaaaa caaacgcata taacgtaaca      1620
acacatggaa acggccaagt atcatatggc gctcgcccaa cacaaaacaa gccaagcaaa      1680
acaaatgcat acaacgtaac aacacatgca acggtcaagt gtcatacgg agctcgcccg      1740 acatacaaga agccaagtaa aacaaatgca tacaatgtaa caacacatgc agatggtact      1800
gcgacatatg ggcctagagt aacaaaataa                                      1830
```

<210> SEQ ID NO 2
<211> LENGTH: 1977
<212> TYPE: DNA
<213> ORGANISM: Staphylococcus aureus

<400> SEQUENCE: 2

```
atgaaaaagc aataatttc gctaggcgca ttagcagttg catctagctt atttacatgg       60
gataacaaag cagatgcgat agtaacaaag gattatagta agaatcaag agtgaatgag       120 aaaagtaaaa agggagctac tgtttcagat tattactatt ggaaaataat tgatagttta      180
gaggcacaat ttactggagc aatagactta ttggaagatt ataaatatgg agatcctatc      240 tataagaag cgaaagatag attgatgaca agagtattag gagaagacca gtatttatta      300
aagaaaaaga ttgatgaata tgagctttat aaaaagtggt ataaaagttc aaataagaac      360
actaatatgc ttactttcca taaatataat ctttacaatt taacaatgaa tgaatataac      420
gatattttta actctttgaa agatgcagtt tatcaattta taaagaagt taagaaata       480 gagcataaaa atgttgactt gaagcagttt gataaagatg gagaagacaa ggcaactaaa      540
gaagtttatg accttgtttc tgaaattgat acattagttg taacttatta tgctgataag      600
gattatgggg agcatgcgaa agagttacga gcaaaactgg acttaatcct tggagataca      660
```

-continued

```
gacaatccac ataaaattac aaatgagcgt ataaaaaaag aaatgatcga tgacttaaat      720
tcaattatag atgatttctt tatggagact aaacaaaata gaccgaattc tataacaaaa      780
tatgatccaa caaaacacaa ttttaaagag aagagtgaaa ataaacctaa ttttgataaa      840
ttagttgaag aaacaaaaaa agcagttaaa gaagcagacg aatcttggaa aaataaaact      900
gtcaaaaaat acgaggaaac tgtaacaaaa tctcctgttg taaaagaaga gaagaaagtt      960
gaagaacctc aattacctaa agttggaaac cagcaagagg ttaaaactac ggctggtaaa     1020
gctgaagaaa caacacaacc agtggcacag ccattagtaa aaattccaca agaaacaatc     1080
tatggtgaaa ctgtaaaagg tccagaatat ccaacgatgg aaaataaaac gttacaaggt     1140
gaaatcgttc aaggtcccga ttttctaaca atggaacaaa acagaccatc tttaagcgat     1200
aattatactc aaccgacgac accgaaccct attttagaag gtcttgaagg tagctcatct     1260
aaacttgaaa taaaaccaca aggtactgaa tcaacgttga aaggtattca aggagaatca     1320
agtgatattg aagttaaacc tcaagcaact gaaacaacag aagcttctca atatggtccg     1380
agaccgcaat ttaacaaaac acctaagtat gtgaaatata gagatgctgg tacaggtatc     1440
cgtgaataca acgatggaac atttggatat gaagcgagac caagattcaa caagccaagt     1500
gaaacaaatg catacaacgt aacgacaaat caagatggca cagtatcata cggagctcgc     1560
ccaacacaaa acaagccaag tgaaacaaac gcatataacg taacaacaca tgcaaatggt     1620
caagtatcat acggtgctcg cccaacacaa aaaaagccaa gcaaaacaaa tgcatacaac     1680
gtaacaacac atgcaaatgg tcaagtatca tatggcgctc gcccgacaca aaaaaagcca     1740
agcaaaacaa atgcatataa cgtaacaaca catgcaaatg gtcaagtatc atacggagct     1800
cgcccgacat acaagaagcc aagcgaaaca aatgcataca acgtaacaac acatgcaaat     1860
ggtcaagtat catatggcgc tcgcccgaca caaaaaaagc caagcgaaac aaacgcatat     1920
aacgtaacaa cacatgcaga tggtactgcg acatatgggc ctagagtaac aaaataa       1977
```

<210> SEQ ID NO 3
<211> LENGTH: 1902
<212> TYPE: DNA
<213> ORGANISM: Staphylococcus aureus

<400> SEQUENCE: 3

```
atgaaaaagc aaataatttc gctaggcgca ttagcagttg catctagctt atttacatgg       60
gataacaaag cagatgcgat agtaacaaag gattatagtg ggaaatcaca agttaatgct      120
gggagtaaaa atgggaaaca aattgcagat ggatattatt ggggaataat tgaaaatcta      180
gaaaaccagt tttacaatat tttttcattta ctggatcagc ataaatatgc agaaaaagaa      240
tataaagatg cagtagataa attaaaaact agagttttag aggaagacca ataccctgcta     300 gaaagaaaaa aagaaaaata cgaaatttat aaagaactat ataaaaaata caaaaaagag     360
aatcctaata ctcaagttaa aatgaaagca tttgataaat acgatcttgg cgatttaact     420
atggaagaat acaatgactt atcaaaatta ttaacaaaag cattggataa ctttaagtta     480
gaagtaaaga aaattgaatc agagaatcca gatttaaaac catattctga agcgaagaa      540 agaacagcat atggtaaaat agattcactt gttgatcaag catatagtgt atatttttgcc     600 tacgttacag atgcacaaca taaaacagaa gcattaaatc ttagggcgaa aattgatttg     660 atttaggtg atgaaaaaga tccaattaga gttacgaatc aacgtactga aaagaaaatg     720
attaaagatt tagaatctat tattgatgat ttcttcattg aaaccaagtt gaatagacct     780
aaacacatta ctaggtatga tggaactaaa catgattacc ataaacataa agatggattt     840
```

-continued

```
gatgctctag ttaaagaaac aagagaagcg gttgcaaagg ctgacgaatc ttggaaaaat      900
aaaactgtca aaaatacga ggaaactgta acaaatctc cagttgtaaa agaagagaag       960
aaagttgaag aacctcaatc acctaaattt gataaccaac aagaggttaa aattacagtt    1020
gataaagctg aagaaacaac acaaccagtg gcacagccat tagttaaaat tccacagggc    1080
acaattacag gtgaaattgt aaaaggtccg gaatatccaa cgatggaaaa taaaacgtta    1140
caaggtgaaa tcgttcaagg tccagatttc ccaacaatgg aacaaaacag accatcttta    1200
agcgataatt atactcaacc gacgacaccg aaccctattt tagaaggtct tgaaggtagc    1260
tcatctaaac ttgaaataaa accacaaggt actgaatcaa cgttaaaagg tactcaagga    1320
gaatcaagtg atattgaagt taaacctcaa gcatctgaaa caacagaagc atcacattat    1380
ccagcaagac ctcaatttaa caaaacacct aaatatgtta aatatagaga tgctggtaca    1440
ggtatccgtg aatacaacga tggaacattt ggatatgaag cgagaccaag attcaataag    1500
ccatcagaaa caaacgcata caacgtaacg acaaatcaag atggcacagt aacatatggc    1560
gctcgcccaa cacaaaacaa accaagcaaa acaaatgcat acaacgtaac aacacatgca    1620
aatggtcaag tatcatatgg cgctcgcccg cacaaaaca agccaagcaa aacaaatgca    1680
tataacgtaa caacacatgc aaatggtcaa gtatcatacg gagctcgccc gacacaaaac    1740
aagccaagca aaacaaatgc atataacgta acaacacacg caaacggtca agtgtcatac    1800
ggagctcgcc cgacatacaa gaagccaagt aaaacaaatg catacaatgt aacaacacat    1860
gcagatggta ctgcgacata tgggcctaga gtaacaaaat aa                       1902
```

<210> SEQ ID NO 4
<211> LENGTH: 1830
<212> TYPE: DNA
<213> ORGANISM: Staphylococcus aureus

<400> SEQUENCE: 4

```
atgaaaaagc aaataatttc gctaggcgca ttagcagttg catctagctt atttacatgg     60
gataacaaag cagatgcgat agtaactaaa gattatagta agaatcaag agtgaatgag    120 aacagtaaat acgatacacc aattccagat tggtatctag gtagtatttt aaacagatta    180
ggggatcaaa tatactacgc taaggaatta actaataaat acgaatatgg tgagaaagag    240
tataagcaag cgatagataa attgatgact agagttttgg gagaagatca ttatctatta    300 gaaaaaaga aagcacaata tgaagcatac aaaaaatggt ttgaaaaaca taaagtgaa     360 aatccacatt ctagtttaaa aaagattaaa tttgacgatt ttgatttata tagattaacg    420
aagaaagaat acaatgagtt acatcaatca ttaaaagaag ctgttgatga gtttaatagt    480
gaagtgaaaa atattcaatc taaacaaaag gatttattac cttatgatga agcaactgaa    540
aatcgagtaa caaatggaat atatgatttt gtttgcgaga ttgacacatt atacgcagca    600
tattttaatc atagccaata tggtcataat gctaaagaat taagagcaaa gctagatata    660
attcttggtg atgctaaaga tcctgttaga attacgaatg aaagaataag aaaagaaatg    720
atggatgatt taaattctat tattgatgat ttctttatgg atacaaacat gaatagacca    780
ttaaacataa ctaaatttaa tccgaatatt catgactata ctaataagcc tgaaaataga    840
gataacttcg ataaattagt caaagaaaca agagaagcaa tcgcaaacgc tgacgaatct    900
tggaaaacaa gaaccgtcaa aaattacggt gaatctgaaa caaatctcc tgttgtaaaa     960 gaagagaaga agttgaaga acctcaatta cctaaagttg gaaccagca agaggataaa    1020
```

| | |
|---|---|
| attacagttg gtacaactga agaagcacca ttaccaattg cgcaaccact agttaaaatt | 1080 |
| ccacagggca caattcaagg tgaaattgta aaaggtccgg aatatctaac gatggaaaat | 1140 |
| aaaacgttac aaggtgaaat cgttcaaggt ccagatttcc caacaatgga acaaaacaga | 1200 |
| ccatctttaa gcgataatta tactcaaccg acgacaccga accctatttt aaaaggtatt | 1260 |
| gaaggaaact caactaaact tgaaataaaa ccacaaggta ctgaatcaac gttaaaaggt | 1320 |
| actcaaggag aatcaagtga tattgaagtt aaacctcaag caactgaaac aacagaagca | 1380 |
| tcacattatc cagcgagacc tcaatttaac aaaacaccta agtatgtgaa atatagagat | 1440 |
| gctggtacag gtatccgtga atacaacgat ggaacatttg gatatgaagc gagaccaaga | 1500 |
| ttcaacaagc caagcgaaac aaatgcatac aacgtaacga caaatcaaga tggcacagta | 1560 |
| tcatatggcg ctcgcccgac acaaaacaag ccaagcgaaa caaacgcata acgtaaca | 1620 |
| acacatgcaa acggccaagt atcatacgga gctcgtccga cacaaaacaa gccaagcgaa | 1680 |
| acgaacgcat ataacgtaac aacacatgca acggtcaag tgtcatacgg agctcgccca | 1740 |
| acacaaaaca agccaagtaa aacaaatgca tacaatgtaa caacacatgc agatggtact | 1800 |
| gcgacatatg gtcctagagt aacaaaataa | 1830 |

<210> SEQ ID NO 5
<211> LENGTH: 1938
<212> TYPE: DNA
<213> ORGANISM: Staphylococcus aureus

<400> SEQUENCE: 5

| | |
|---|---|
| atagtaacaa aggattatag tgggaaatca caagttaatg ctgggagtaa aaatgggaaa | 60 |
| caaattgcag atggatatta ttggggaata attgaaaatc tagagaacca gttttacaat | 120 |
| attttcatt tattggatca gcataaatat gcagaaaaag aatataaaga tgcattagat | 180 |
| aaattaaaaa ctagagtttt agaggaagac caatacctgc tagaaagaaa aaagaaaaa | 240 |
| tacgaaattt ataaggaact atataaaaaa tacaaaaaag agaatcctaa tactcaggtt | 300 |
| aaaatgaaag catttgataa atacgatctt ggcgatttaa ctatggaaga atacaatgac | 360 |
| ttatcaaaat tattaacaaa agcattggat aactttaagt tagaagtaaa gaaaattgaa | 420 |
| tcagagaatc cagatttaag accatattct gaaagtgaag agagaacagc atatggtaaa | 480 |
| atagattcac ttgttgatca gcatatagt gtatattttg cctacgttac agatgctcaa | 540 |
| cataaaacag aagcattaaa tcttagggca aaaatagatt tgattttagg tgatgaaaaa | 600 |
| gatccaatta gagtgacgaa tcaacgtact gaaaaagaaa tgattaaaga tttagaatct | 660 |
| attattgatg atttcttcat tgaaacaaag ttgaatagac ctcaacacat tactagatat | 720 |
| gatggaacta acatgatta ccataaacat aaagatggat tgatgctttt agttaaagaa | 780 |
| acaagagaag cggtttctaa ggctgacgaa tcttggaaaa ctaaaactgt caaaaaatac | 840 |
| ggggaaactg aaacaaaata tcctgttgta aagaagagaa agaagttga agaacctcaa | 900 |
| tcacctaaag tttctgaaaa agtggatgtt caggaacgg ttggtacaac tgaagaagca | 960 |
| ccattaccaa ttgcgcaacc actagttaaa ttaccacaaa ttgggactca aggcgaaatt | 1020 |
| gtaaaaggtc ccgactatcc aactatgaa aataaaacgt acaaggtgt aattgttcaa | 1080 |
| ggtccagatt tcccaacaat ggaacaaaac agaccatctt aagtgacaa ttatacacaa | 1140 |
| ccatctgtga ctttaccgtc aattacaggt gaaagtacac caacgaaccc tattttaaaa | 1200 |
| ggtattgaag gaaactcatc taaacttgaa ataaaaccac aaggtactga atcaacgttg | 1260 |
| aaaggtattc aaggagaatc aagtgatatt gaagttaaac ctcaagcaac tgaaacaaca | 1320 |

```
gaagcatcac attatccagc gagaccgcaa tttaacaaaa cacctaaata tgtgaaatat    1380
agagatgctg gtacaggtat tcgtgaatac aacgatggaa cttttggata tgaagcgaga    1440
ccaagattca acaagccatc agaaacaaac gcatacaacg taacgacaaa tcaagatggc    1500
acagtatcat atggggctcg cccaacacaa aacaagccaa gcaaaacaaa tgcatataac    1560
gtaacaacac atgcaaacgg ccaagtatca tatggcgctc gcccgacata caacaagcca    1620
agtgaaacaa atgcatacaa cgtaacgaca atcgagatg gcacagtatc atatggcgct    1680
cgcccgacac aaaacaagcc aagcgaaacg aatgcatata acgtaacaac acacggaaat    1740
ggccaagtat catatggcgc tcgtccgaca caaaagaagc caagcaaaac aaatgcatat    1800
aacgtaacaa cacatgcaaa cggccaagta tcatatggcg ctcgtccgac atacaacaag    1860
ccaagtaaaa caaatgcata caatgtaaca acacatgcag atggtactgc gacatatggt    1920
cctagagtaa caaaataa                                                   1938

<210> SEQ ID NO 6
<211> LENGTH: 2013
<212> TYPE: DNA
<213> ORGANISM: Staphylococcus aureus

<400> SEQUENCE: 6
gattgggcaa ttcattttg gaggaattaa aaaattatga aaaagcaaat aatttcgcta      60
ggcgcattag cagttgcatc tagcttattt acatgggata caaagcaga tgcgatagta     120 acaaaggatt atagtaaaga atcaagagtg aatgagaaaa gtaaaaaggg agctactgtt     180
tcagattatt actattggaa ataaattgat agtttagagg cacaatttac tggagcaata     240
gacttattgg aagattataa atatggagat cctatctata agaagcgaa agatagattg     300 atgacaagag tattaggaga agaccagtat ttattaaaga aaaagattga tgaatatgag     360
ctttataaaa agtggtataa aagttcaaat aagaacacta atatgcttac tttccataaa     420
tataatcttt acaatttaac aatgaatgaa tataacgata ttttttaactc tttgaaagat     480 gcagtttatc aatttaataa agaagttaaa gaaatagagc ataaaatgt tgacttgaag     540 cagtttgata agatggaga agacaaggca actaaagaag tttatgaccct tgtttctgaa     600 attgatacat tagttgtaac ttattatgct gataaggatt atggggagca tgcgaaagag     660
ttacgagcaa aactggactt aatccttgga gatacagaca atccacataa aattacaaat     720
gagcgtataa aaaagaaat gatcgatgac ttaaattcaa ttatagatga tttcttttatg     780 gagactaaac aaaatagacc gaattctata acaaaatatg atccaacaaa acacaattttt     840 aaagagaaga gtgaaaataa acctaattttt gataaattag ttgaagaaac aaaaaaagca     900
gttaaagaag cagacgaatc ttggaaaaat aaaactgtca aaaatacga ggaaactgta     960 acaaaatctc ctgttgtaaa agaagagaag aaagttgaag aacctcaatt acctaaagtt    1020
ggaaaccagc aagaggttaa aactacggct ggtaaagctg aagaacaac acaaccagtg    1080 gcacagccat tagtaaaaat tccacaagaa acaatctatg gtgaaactgt aaaaggtcca    1140
gaatatccaa cgatggaaaa taaaacgtta caaggtgaaa tcgttcaagg tcccgatttt    1200
ctaacaatgg aacaaacag accatcttta agcgataatt tactcaacc gacgacaccg    1260 aaccctatt tagaaggtct tgaaggtagc tcatctaaac ttgaaataaa accacaaggt    1320
actgaatcaa cgttgaaagg tattcaagga gaatcaagtg atattgaagt taaacctcaa    1380
gcaactgaaa caacagaagc ttctcaatat ggtccgagac cgcaattaa caaaacacct    1440
```

-continued

| | |
|---|---|
| aagtatgtga aatatagaga tgctggtaca ggtatccgtg aatacaacga tggaacattt | 1500 |
| ggatatgaag cgagaccaag attcaacaag ccaagtgaaa caaatgcata caacgtaacg | 1560 |
| acaaatcaag atggcacagt atcatacgga gctcgcccaa cacaaaacaa gccaagtgaa | 1620 |
| acaaacgcat ataacgtaac aacacatgca aatggtcaag tatcatacgg tgctcgccca | 1680 |
| acacaaaaaa agccaagcaa acaaatgcta caacgtaa caacacatgc aaatggtcaa | 1740 |
| gtatcatatg cgctcgccc gacacaaaaa aagccaagca aaacaaatgc atataacgta | 1800 |
| acaacacatg caaatggtca agtatcatac ggagctcgcc cgacatacaa gaagccaagc | 1860 |
| gaaacaaatg catacaacgt aacaacacat gcaaatggtc aagtatcata tggcgctcgc | 1920 |
| ccgacacaaa aaaagccaag cgaaacaaac gcatataacg taacaacaca tgcagatggt | 1980 |
| actgcgacat atgggcctag agtaacaaaa taa | 2013 |

<210> SEQ ID NO 7
<211> LENGTH: 1914
<212> TYPE: DNA
<213> ORGANISM: Staphylococcus aureus

<400> SEQUENCE: 7

| | |
|---|---|
| atagtaacta aagattatag taaagaatca agagtgaatg agaacagtaa atacgataca | 60 |
| ccaattccag attggtatct aggtagtatt ttaaacagat taggggatca aatatactac | 120 |
| gctaaggaat taactaataa atacgaatat ggtgagaaag agtataagca agcgatagat | 180 |
| aaattgatga ctagagtttt gggagaagat cattatctat tagaaaaaaa gaaagcacaa | 240 |
| tatgaagcat acaaaaaatg gtttgaaaaa cataaagtg aaaatccaca ttctagttta | 300 |
| aaaaagatta aatttgacga ttttgattta tatagattaa cgaagaaaga atacaatgag | 360 |
| ttacatcaat cattaaaaga agctgttgat gagtttaata gtgaagtgaa aaatattcaa | 420 |
| tctaaacaaa aggatttatt accttatgat gaagcaactg aaaatcgagt aacaaatgga | 480 |
| atatatgatt ttgtttgcga gattgacaca ttatacgcag catattttaa tcatagccaa | 540 |
| tatggtcata atgctaaaga attaagagca aagctagata taattcttgg tgatgctaaa | 600 |
| gatcctgtta gaattacgaa tgaaagaata agaaaagaaa tgatggatga tttaaattct | 660 |
| attattgatg atttctttat ggatacaaac atgaatagac cattaaacat aactaaattt | 720 |
| aatccgaata ttcatgacta tactaataag cctgaaaata gagataactt cgataaatta | 780 |
| gtcaaagaaa caagagaagc agtcgcaaac gctgacgaat cttggaaaac aagaaccgtc | 840 |
| aaaaattacg gtgaatctga aacaaaatct cctgttgtaa agaagagaa gaaagttgaa | 900 |
| gaacctcaat tacctaaagt tggaaaccag caagaggata aaattacagt tggtacaact | 960 |
| gaagaagcac cattaccaat tgcgcaacca ctagttaaaa ttccacaggg cacaattcaa | 1020 |
| ggtgaaattg taaaggtcc ggaatatcta acgatggaaa ataaaacgtt acaaggtgaa | 1080 |
| atcgttcaag gtccagattt cccaacaatg gaacaaaaca gaccatcttt aagcgataat | 1140 |
| tatactcaac cgacgacacc gaaccctatt ttaaaggta ttgaaggaaa ctcaactaaa | 1200 |
| cttgaaataa aaccacaagg tactgaatca acgttaaaag gtactcaagg agaatcaagt | 1260 |
| gatattgaag ttaaacctca agcaactgaa acaacagaag catcacatta tccagcgaga | 1320 |
| cctcaatttta acaaaacacc taagtatgtg aaatatagag atgctggtac aggtatccgt | 1380 |
| gaatacaacg atggaacatt tggatatgaa gcgagaccaa gattcaacaa gccaagcgaa | 1440 |
| acaaatgcat acaacgtaac gacaaatcaa gatggcacag tatcatatgg cgctcgcccg | 1500 |
| acacaaaaaca aaccaagcga aacaaatgca tacaacgtaa caacacatgc aaacggccaa | 1560 |

| | | |
|---|---|---|
| gtatcatatg gcgcccgccc aacatacaag aagccaagcg aaacaaacgc atacaacgta | 1620 |
| acgacaaatc aagatggcac agtatcatat ggcgctcgcc cgacacaaaa caagccaagc | 1680 |
| gaaacaaacg catataacgt aacaacacat gcaaacggcc aagtatcata cggagctcgt | 1740 |
| ccgacacaaa acaagccaag cgaaacgaac gcatataacg taacaacaca tgcaaacggt | 1800 |
| caagtgtcat acggagctcg cccaacacaa aacaagccaa gtaaaacaaa tgcatacaat | 1860 |
| gtaacaacac atgcagatgg tactgcgaca tatggtccta gagtaacaaa ataa | 1914 |

<210> SEQ ID NO 8
<211> LENGTH: 1911
<212> TYPE: DNA
<213> ORGANISM: Staphylococcus aureus

<400> SEQUENCE: 8

| | | |
|---|---|---|
| atgaaaaagc aaataatttc gctaggcgca ttagcagttg catctagctt atttacatgg | 60 |
| gataacaaag cagatgcgat agtaacaaag gattatagtg ggaaatcaca agttaatgct | 120 |
| gggagtaaaa atgggacatt aatagatagc agatatttaa attcagctct atattatttg | 180 |
| gaagactata taatttatgc tataggatta actaataaat atgaatatgg agataatatt | 240 |
| tataaagaag ctaaagatag gttgttggaa aaggtattaa gggaagatca atatcttttg | 300 |
| gagagaaaga atctcaata tgaagattat aaacaatggt atgcaaatta taaaaaagaa | 360 |
| aatcctcgta cagatttaaa aatggctaat tttcataaat ataatttaga agaactttcg | 420 |
| atgaaagaat acaatgaact acaggatgca ttaagagag cactggatga ttttcacaga | 480 |
| gaagttaaag atattaagga taagaattca gacttgaaaa cttttaatgc agcagaagaa | 540 |
| gataaagcaa ctaaggaagt atacgatctc gtatctgaaa ttgatacatt agttgtatca | 600 |
| tattatggtg ataaggatta tggggagcac gcgaaagagt tacgagcaaa actggactta | 660 |
| atccttggag atacagacaa tccacataaa attacaaatg aacgtattaa aaagaaatg | 720 |
| attgatgact taaattcaat tattgatgat ttctttatgg aaactaaaca aaatagaccg | 780 |
| aaatctataa cgaaatataa tcctacaaca cataactata aacaaatag tgataataaa | 840 |
| cctaattttg ataaattagt tgaagaaacg aaaaaagcag ttaaagaagc agatgattct | 900 |
| tggaaaaaga aaactgtcaa aaaatacgga gaaactgaaa caaaatcgcc agtagtaaaa | 960 |
| gaagagaaga agttgaaga acctcaagca cctaaagttg ataaccaaca agaggttaaa | 1020 |
| actacggctg gtaaagctga agaaacaaca caaccagttg cacaaccatt agttaaaatt | 1080 |
| ccacagggca caattacagg tgaaattgta aaaggtccgg aatatccaac gatggaaaat | 1140 |
| aaaacggtac aaggtgaaat cgttcaaggt cccgattttc taacaatgga acaaagcggc | 1200 |
| ccatcattaa gcaataatta tacaaaccca ccgttaacga accctatttt agaaggtctt | 1260 |
| gaaggtagct catctaaact tgaaataaaa ccacaaggta ctgaatcaac gttaaaggt | 1320 |
| actcaaggag aatcaagtga tattgaagtt aaacctcaag caactgaaac aacagaagct | 1380 |
| tctcaatatg gtccgagacc gcaatttaac aaaacaccta aatatgttaa atatagagat | 1440 |
| gctggtacag gtatccgtga atacaacgat ggaacatttg gatatgaagc gagaccaaga | 1500 |
| ttcaataagc catcagaaac aaatgcatat aacgtaacaa cacatgcaaa tggtcaagta | 1560 |
| tcatacggag ctcgtccgac atacaagaag ccaagcgaaa cgaatgcata caatgtaaca | 1620 |
| acacatgcaa acggccaagt atcatacgga gctcgtccga cacaaaacaa gccaagcaaa | 1680 |
| acaaacgcat ataacgtaac aacacatgga aacggccaag tatcatatgg cgctcgccca | 1740 |

```
acacaaaaca agccaagcaa acaaatgca tacaacgtaa caacacatgc aaacggtcaa    1800
gtgtcatacg gagctcgccc gacatacaag aagccaagta aaacaaatgc atacaatgta    1860
acaacacatg cagatggtac tgcgacatat gggcctagag taacaaaata a             1911

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 9

Gln Ser Val Asp Tyr Asn Gly Ile Ser Tyr
1               5                   10

<210> SEQ ID NO 10
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 10

Ala Ala Ser
1

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 11

Gln Gln Ser Ile Glu Asp Pro Arg Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Gly Phe Asn Ile Lys Asp Ile Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 13

Ile Asp Pro Ala Asn Gly Asn Thr
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Peptide
```

```
<400> SEQUENCE: 14

Ser Arg Ser Gly Ala Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Ser Ser Val Ser Ser Tyr
1               5

<210> SEQ ID NO 16
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 16

Ser Thr Ser
1

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Gln Gln Tyr His Arg Ser Pro Pro Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 18

Gly Ala Ser Ile Thr Thr Ser Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Ile Ser Tyr Ser Gly Asn Thr
1               5

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20
```

```
Ala Ala Thr Tyr Tyr Asp Phe Asn Tyr Asp Gly Tyr Leu Asp Val
1               5                   10                  15

<210> SEQ ID NO 21
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 21

Ala Ala Ser
1

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 22

His Gln Ser Ile Glu Asp Pro Arg Thr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 23

Ser Arg Ser Gly Ala Phe
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 24

Gln Ser Ile Val His Ser Asn Gly Asn Thr Tyr
1               5                   10

<210> SEQ ID NO 25
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 25

Lys Val Ser
1

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 26
```

```
Phe Gln Gly Ser His Val Pro Leu Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 27

Gly Tyr Thr Phe Thr Ser Phe Asp
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 28

Ile Phe Pro Gly Asp Gly Ser Ser
1               5

<210> SEQ ID NO 29
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 29

Val Lys Asn His Gly Gly Trp Ser Phe Asp Val
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

His Gln Ser Ile Glu Asp Pro Arg Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 31

Ile Asp Pro Ala Asp Gly His Ser
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 32

Ser Arg Ser Gly Ala Ile
```

```
1               5
```

<210> SEQ ID NO 33
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 33

```
Gln Ser Leu Leu Asn Ser Arg Ala Arg Lys Asn Tyr
1               5                   10
```

<210> SEQ ID NO 34
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 34

```
Trp Ala Ser
1
```

<210> SEQ ID NO 35
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 35

```
Lys Gln Ser Tyr Asn Leu Trp Thr
1               5
```

<210> SEQ ID NO 36
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 36

```
Lys Gln Ser Tyr Tyr Leu Trp Thr
1               5
```

<210> SEQ ID NO 37
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 37

```
Ile Asn Thr Glu Thr Gly Glu Pro
1               5
```

<210> SEQ ID NO 38
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 38

```
Ala Arg Thr Ala Arg Ala Asp Tyr
1               5
```

```
<210> SEQ ID NO 39
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 39

Ala Arg Thr Ala Arg Asp Tyr
1               5

<210> SEQ ID NO 40
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 40

Gln Ser Leu Leu Asn Ser Arg Ala Arg Lys Asn Tyr
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 41

Gly Tyr Thr Leu Thr Asp Tyr Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic peptide

<400> SEQUENCE: 42

Gly Arg Thr Ala Arg Ala Asp Tyr
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 43

Ile Asn Thr Glu Thr Gly Asp Pro
1               5

<210> SEQ ID NO 44
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 44

Gln Ser Leu Leu Asn Ser Arg Thr Arg Lys Ile Tyr
1               5                   10
```

```
<210> SEQ ID NO 45
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 45

Lys Gln Ser Tyr Tyr Leu Tyr Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 46

Gly Phe Ser Phe Ser Asn Tyr Trp
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 47

Ile Arg Leu Lys Ser Asp Asn Tyr Gly Thr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 48

Ser Ala Tyr Gly Asp Tyr Glu Tyr
1               5

<210> SEQ ID NO 49
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 49

Gln Ser Leu Phe Asn Ser Arg Ala Arg Lys Asn Tyr
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 50

Gly Tyr Glu Phe Thr Asp Phe Glu
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: Synthetic peptide

<400> SEQUENCE: 51

Phe Asp Pro Glu Thr Gly Arg Ser
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 52

Ser Arg Phe His Tyr Tyr Gly Arg Thr Ala Tyr
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide

<400> SEQUENCE: 53

Gly Phe Thr Phe Ser Asn Tyr Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 54

Ile Lys Ser Asn Gly Val Ser Thr
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic peptide

<400> SEQUENCE: 55

Val Arg His Asp Gly Tyr Tyr Phe Ala Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide

<400> SEQUENCE: 56

Gln Asn Ile Val His Ser Asn Gly Asn Thr Tyr
1               5                   10

<210> SEQ ID NO 57
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 57

Leu Gln Gly Ser Asn Cys Ser Asn His
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 58

Gly Phe Ser Ile Lys Asp Thr Thr
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 59

Ile Asp Pro Thr Asp Gly His Asn
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 60

Lys Gln Ser Tyr Asn Leu Trp Thr
1               5

<210> SEQ ID NO 61
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa can be Alanine [A], Serine [S], Lysine [K]
      or Tryptophan [W]
<220> FEATURE:
<221> NAME/KEY: MISC_FEATURE
<222> LOCATION: (2)..(2)
<223> OTHER INFORMATION: Xaa can be Alanine [A], Threonine [T] or
      Valine [V]

<400> SEQUENCE: 61

Xaa Xaa Ser
1
```

US 9,701,738 B2

COMPOSITIONS AND METHODS RELATED TO ANTIBODIES THAT NEUTRALIZE COAGULASE ACTIVITY DURING *STAPHYLOCOCCUS AUREUS* DISEASE

This application is a national phase application under 35 U.S.C. §371 of International Applicatioon No. PCT/US2013/031927, filed Mar. 15, 2013, which claims priority to U.S. Provisional Patent Application Ser. No. 61/638,797 filed on Apr. 26, 2012. The entire contents of each of the above-referenced disclosures are specifically incorporated herein by reference without disclaimer.

This invention was made with government support under AI057153 and AI092711 awarded by the National Institutes of Health. The government has certain rights in the invention.

I. FIELD OF THE INVENTION

The present invention relates generally to the fields of immunology, microbiology, and pathology. More particularly, it concerns methods and compositions involving antibodies to bacterial proteins and bacterial peptides used to elicit such antibodies. The proteins include Coagulase (Coa).

II. BACKGROUND

North American hospitals are experiencing an epidemic of *Staphylococcus aureus*. This organism causes a wide range of diseases from minor skin infections to life-threatening sepsis, endocarditis, and pneumonia [2]. *S. aureus* is endowed with a wide range of virulence factors that enable its many disease manifestations. One of the defining characteristics of *S. aureus* that distinguishes it from less pathogenic species of staphylococci is its ability to clot anticoagulated blood [48,75]. This characteristic is due to two proteins, coagulase (Coa) and von Willebrand factor binding protein (vWbp). Coa and vWbp bind to and induce a conformational change in host prothrombin, which mimics the transition from the zymogen to activated thrombin, enabling the complex to cleave fibrinogen to fibrin [66,67, 71,72,133,146,188]. Fibrin forms the mesh network of a blood clot.

Coa and vWbp play an important role during the pathogenesis of *S. aureus* infection [212]. Infection with double mutants in coa and vwb results in delayed mortality in a murine sepsis model and nearly eliminates the ability of staphylococci to form abscesses (Cheng et al 2010). A humoral immune response against Coa and vWbp provides protection against staphylococcal infection (Cheng et al 2010). Pharmacologic inhibition of the coagulases with direct thrombin inhibitors neutralizes the activity of Coa and vWbp and provides prophylactic protection against staphylococcal sepsis [20,177,213].

*S. aureus* can survive on dry surfaces, increasing the chance of transmission. Any *S. aureus* infection can cause the staphylococcal scalded skin syndrome, a cutaneous reaction to exotoxin absorbed into the bloodstream. *S. aureus* can also cause a type of septicemia called pyaemia that can be life-threatening. Methicillin-resistant *Staphylococcus aureus* (MRSA) has become a major cause of hospital-acquired infections.

*S. aureus* infections are typically treated with antibiotics, with penicillin being the drug of choice, but vancomycin being used for methicillin resistant isolates. The percentage of staphylococcal strains exhibiting wide-spectrum resistance to antibiotics has increased, posing a threat to effective antimicrobial therapy. In addition, the recent appearance of vancomycin-resistant *S. aureus* strain has aroused fear that MRSA strains for which no effective therapy is available are starting to emerge and spread.

An alternative approach to antibiotics in the treatment of staphylococcal infections has been the use of antibodies against staphylococcal antigens in passive immunotherapy. Examples of this passive immunotherapy involves administration of polyclonal antisera (WO00/15238, WO00/12132) as well as treatment with monoclonal antibodies against lipoteichoic acid (WO98/57994).

The first generation of vaccines targeted against *S. aureus* or against the exoproteins it produces have met with limited success (Lee, 1996) and there remains a need to develop additional therapeutic compositions for treatment of *staphylococcus* infections.

SUMMARY OF THE INVENTION

*Staphylococcus aureus* is the most frequent cause of bacteremia and hospital-acquired infection in the United States. An FDA approved vaccine that prevents staphylococcal disease is currently unavailable.

In certain embodiments there are antibody compositions that inhibit, ameliorate, and/or prevent Staphylococcal infection.

Certain embodiments are directed to methods of inhibiting *Staphylococcus* infection in a patient determined to have or be at risk for *Staphylococcus* infection comprising administering to the patient an effective amount of a Coa binding polypeptide that specifically binds to Domain 1-2 of a Staphylococcal Coa polypeptide. In some embodiments, the method further comprises administering an effective amount of two or more Coa binding polypeptides. In some embodiments, the method further comprises administering an antibiotic or a Staphylococcal vaccine composition to the patient. In other embodiments, there are methods for treating a patient with or determined to have a *Staphylococcus* infection. In further embodiments, there are methods for preventing a *Staphylococcus* infection.

In some aspects, the Coa binding polypeptide specifically binds to Domain 1 of a Staphylococcal Coa polypeptide. In other aspects, the Coa binding polypeptide specifically binds to Domain 2 of a Staphylococcal Coa polypeptide. In further embodiments, the Coa binding polypeptide specifically binds to a region on both Domain 1 and Domain 2 of a Staphylococcal Coa polypeptide.

Certain embodiments are directed to a Coa binding polypeptide that specifically binds to an epitope in a polypeptide encoded by any of SEQ ID NOs: 1-8. In certain aspects, the Coa binding polypeptide specifically binds to an epitope in amino acids 1-149, 150-282, or 1-282 of a polypeptide encoded by any of SEQ ID NOs: 1-8. In certain aspects the epitope comprises at least, or has at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids (or any range derivable therein) from any of the sequences provided herein or encoded by any of the sequences provided herein.

In particular embodiments, the Coa binding polypeptide competes for binding of Staphylococcal Coa polypeptide with the 5D5.4 or 7H4.25 monoclonal antibody. In further embodiments, the monoclonal antibody is 4H9.20, 4B10.44, 3B3.14, 2A3.1, 2H10.12, 6D1.22, 6C4.15, 6C10.19, 8C2.9, or 4F1.7. In some embodiments, the Coa binding polypeptide has an association constant for the Staphylococcal Coa polypeptide of between about 0.5 and 20 nM$^{-1}$, 1.0 and 10 nM$^{-1}$, or 1.0 and 6.0 nM$^{-1}$ as measured by ELISA. In certain embodiments, the Coa binding polypeptide has an association constant for the Staphylococcal Coa Domain 1-2 of between about 0.5 and 20 nM$^{-1}$ or 1.0 and 10 nM$^{-1}$ as measured by ELISA.

The Coa binding polypeptide may be any polypeptide that specifically binds Coa proteins from staphylococcus bacteria. In certain embodiments, the Coa binding polypeptide is a purified monoclonal antibody or a purified polyclonal antibody. The polypeptide may be, for example, an antibody that is single domain, humanized, or chimeric. In some embodiments, two or more Coa binding polypeptides (e.g., two or more purified monoclonal antibodies or purified polyclonal antibodies) may be administered to the patient. In certain aspects, the Coa binding polypeptide is recombinant. In other embodiments, there may be chemical modifications to the polypeptide, such as the addition of one or more chemical modifications or moieties.

Embodiments are provided in which the Coa binding polypeptide comprises one or more CDR domains from an antibody that specifically binds to Domains 1-2 of a Staphylococcal Coa polypeptide. In particular embodiments, the Coa binding polypeptide comprises one, two, three, four, five, six, or more CDR domains from among the VH or VL domain of the 5D5.4 and 7H4.25 monoclonal antibodies. In certain aspects, the Coa binding polypeptide comprises six CDR domains from among the VH or VL domains of the 5D5.4 and 7H4.25 monoclonal antibodies. In some embodiments, the Coa binding polypeptide comprises a sequence at least or at most 70%, 75%, 80%, 85%, 90%, 95%, or 99% (or any range derivable therein) identical to the VH or VL domain of the 5D5.4 or 7H4.25 monoclonal antibodies. Embodiments are provided in which the Coa binding polypeptide comprises the VH domain from the 5D5.4 or 7H4.25 monoclonal antibody and/or the VL domain the 5D5.4 or 7H4.25 monoclonal antibody. In further embodiments, the monoclonal antibody is 4H9.20, 4B10.44, 3B3.14, 2A3.1, 2H10.12, 6D1.22, 6C4.15, 6C10.19, 8C2.9, or 4F1.7.

In some embodiments the Coa binding polypeptide comprises one or more CDR domains from a Coa binding polypeptide that specifically binds to Domain 1-2 of a Staphylococcal Coa polypeptide and a scaffold from a polypeptide selected from the group consisting of an immunoglobulin, a fibronectin or a *S. aureus* protein Z.

The Coa binding polypeptide may be operatively coupled to a second Coa binding polypeptide. In some aspects, the first and second Coa binding peptides are operatively coupled recombinantly. In other aspects, the first and second Coa binding peptides are operatively coupled chemically.

Embodiments are provided in which the Coa binding polypeptide is administered at a dose of about, at least about, or at most about 0.1 mg/kg to 5 mg/kg, 1 mg/kg to 5 mg/kg, 0.1 mg/kg to 1 mg/kg, or 2 mg/kg to 5 mg/kg (or any range derivable therein).

Embodiments also provide a purified polypeptide comprising one or more Coa binding polypeptide CDR domains from an antibody that specifically binds to Domain 1-2 of a Staphylococcal Coa polypeptide. In certain embodiments, the Coa binding polypeptide competes for binding of a Staphylococcal Coa polypeptide with the 4H9.20, 4B10.44, 3B3.14, 4F1.7, 6C4.15, 8C2.9, 2A3.1, 5C3.2, 2H10.12, 6D1.22, 6C10.19, 5D5.4 or 7H4.25 monoclonal antibody. In certain aspects, the polypeptide has an association constant for a Staphylococcal Coa polypeptide of between about 0.1 and 20 nM$^{-1}$, 0.5 and 10 nM$^{-1}$, or 1.0 and 10 nM$^{-1}$ as measured by ELISA. The polypeptide may comprise, for example, a single domain antibody Coa binding polypeptide, a humanized antibody, or a chimeric antibody.

In certain embodiments, the polypeptide is recombinant. In certain aspects, the recombinant polypeptide comprises at least 90%, 95%, or 99% of one or more CDR domains from the VH or VL domain of the 4H9.20, 4B10.44, 3B3.14, 4F1.7, 8C2.9, 2A3.1, 5C3.2, 2H10.12, 6D1.22, 6C4.15, 6C10.19, 5D5.4 or 7H4.25 monoclonal antibodies. In some embodiments, the recombinant polypeptide comprises two, three, four, five, six, or more CDR domains from the VH or VL domain of the 4H9.20, 4B10.44, 3B3.14, 4F1.7, 8C2.9, 2A3.1, 5C3.2, 2H10.12, 6D1.22, 6C4.15, 6C10.19, 5D5.4 and/or 7H4.25 monoclonal antibodies.

In some embodiments, a recombinant polypeptide comprises i) CDR1, CDR2, and/or CDR3 from the variable light chain of 4H9.20; and/or ii) CDR1, CDR2, and/or CDR3 from the variable heavy chain of 4H9.20. In some embodiments, a recombinant polypeptide comprises i) CDR1, CDR2, and/or CDR3 from the variable light chain of 5D5.4; and/or ii) CDR1, CDR2, and/or CDR3 from the variable heavy chain of 5D5.4. In some embodiments, a recombinant polypeptide comprises i) CDR1, CDR2, and/or CDR3 from the variable light chain of 4B10.44; and/or ii) CDR1, CDR2, and/or CDR3 from the variable heavy chain of 4B10.44. In some embodiments, a recombinant polypeptide comprises i) CDR1, CDR2, and/or CDR3 from the variable light chain of 3B3.14; and/or ii) CDR1, CDR2, and/or CDR3 from the variable heavy chain of 3B3.14. In some embodiments, a recombinant polypeptide comprises i) CDR1, CDR2, and/or CDR3 from the variable light chain of 7H4.25; and/or ii) CDR1, CDR2, and/or CDR3 from the variable heavy chain of 7H4.25. In some embodiments, a recombinant polypeptide comprises i) CDR1, CDR2, and/or CDR3 from the variable light chain of 2A3.1; and/or ii) CDR1, CDR2, and/or CDR3 from the variable heavy chain of 2A3.1. In some embodiments, a recombinant polypeptide comprises i) CDR1, CDR2, and/or CDR3 from the variable light chain of 2H110.12; and/or ii) CDR1, CDR2, and/or CDR3 from the variable heavy chain of 2H10.12. In some embodiments, a recombinant polypeptide comprises i) CDR1, CDR2, and/or CDR3 from the variable light chain of 6D1.22; and/or ii) CDR1, CDR2, and/or CDR3 from the variable heavy chain of 6D1.22. In some embodiments, a recombinant polypeptide comprises i) CDR1, CDR2, and/or CDR3 from the variable light chain of 6C4.15; and/or ii) CDR1, CDR2, and/or CDR3 from the variable heavy chain of 6C4.15. In some embodiments, a recombinant polypeptide comprises i) CDR1, CDR2, and/or CDR3 from the variable light chain of 6C10.19; and/or ii) CDR1, CDR2, and/or CDR3 from the variable heavy chain of 6C10.19. In some embodiments, a recombinant polypeptide comprises i) CDR1, CDR2, and/or CDR3 from the variable light chain of 8C2.9; and/or ii) CDR1, CDR2, and/or CDR3 from the variable heavy chain of 8C2.9. In some embodiments, a recombinant polypeptide comprises i) CDR1, CDR2, and/or CDR3 from the variable light chain of 4F1.7; and/or ii) CDR1, CDR2, and/or CDR3 from the variable heavy chain of 4F1.7. The sequences for these CDRs can be found in Table 5.

In some embodiments, there is a purified polypeptide comprising one or more Coa binding polypeptide CDR domains from an antibody that specifically binds to Domain 1-2 of a Staphylococcal Coa polypeptide. As indicated above, the polypeptide may comprise 1, 2, 3, 4, 5, or 6 CDRs from the light and/or heavy chain variable regions of a Coa antibody. Table 5 provides 12 different Coa antibodies and their CDR1, CDR2, and CDR3 sequences from both the light and heavy chain variable regions. In certain embodiments, a polypeptide contains CDR1, CDR2, and/or CDR3 from the light chain variable region of a particular antibody. It is contemplated that while in some embodiments a polypeptide has a CDR1, CDR2, and CDR3 from the variable region of a light chain and/or the variable region of a heavy chain that the CDR1, CDR2, and CDR3 need not be from the same antibody. While some polypeptides have CDR1, CDR2, and CDR3 from the same antibody or based on the same antibody, given the overlap in amino acid sequences, a CDR1 from one antibody may be substituted with a CDR from or based on another antibody. For example, a polypeptide may comprise a CDR1 from or based on the light chain variable region of 4F1.7, a CDR2 from or based on the light chain variable region of 4F1., but have a CDR3 from or based on the variable light chain region of 6C4.15. It is generally contemplated, however, that when a single set of CDR1, CDR2, and CDR3 are employed together that they all be from a light chain variable region or from a heavy chain variable region, but not a mix from both.

Alternatively, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs:9, 15, 24, 33, 40, 44, 56, and 49, which are CDR1 sequences from the light chain variable region of a Coa antibody. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs:10, 16, 21, 25, and 34, which are CDR2 sequences from the light chain variable region of a Coa antibody. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs: 11, 17, 22, 26, 30, 35, 36, 45, and 57, which are CDR3 sequences from the light chain variable region of a Coa antibody. Alternatively or additionally, the polypeptide may contain a CDR1 sequence that is, is at most or is at least 70, 75, 80, 85, 90, 95, 96, 97, 98, 99, 100% identical (or any range derivable therein) to the entire sequence set forth in SEQ ID NOs:12, 18, 27, 37, 41, 46, 50, 53, and 58, which are CDR1 sequences from the heavy chain variable region of a Coa antibody. Alternatively or additionally, the polypeptide may contain a CDR2 sequence that is, is at most or is at least 70, 75, 80, 85, 90, 95, 96, 97, 98, 99, 100% identical (or any range derivable therein) to the entire sequence set forth in SEQ ID NOs:13, 19, 28, 31, 38, 43, 47, 51, 54, and 59, which are CDR2 sequences from the heavy chain variable region of a Coa antibody. Alternatively or additionally, the polypeptide may contain a CDR3 sequence that is, is at most or is at least 70, 75, 80, 85, 90, 95, 96, 97, 98, 99, 100% identical (or any range derivable therein) to the entire sequence set forth in SEQ ID NOs:14, 20, 23, 29, 32, 39, 42, 48, 52, 55, and 60, which are CDR3 sequences from the heavy chain variable region of a Coa antibody. It is contemplated that in some embodiments, SEQ ID NO:61 is used in place of any of SEQ ID NOs:10, 16, 21, 25, and 34. In some embodiments, a CDR2 has the sequence of SEQ ID NO:61.

Other embodiments provide a recombinant polypeptide that comprises one or more CDR domain from an antibody that specifically binds to Domains 1-2 of a Staphylococcal Coa polypeptide and a scaffold from a polypeptide selected from the group consisting of an immunoglobulin, a fibronectin or a *S. aureus* protein Z. If it further contemplated that any polypeptide may be attached, fused or conjugated to an agent or substance, such a therapeutic moiety or a detectable moirty.

In certain aspects, the recombinant polypeptide is operatively coupled to a recombinant polypeptide that specifically binds to a second Staphylococcal protein.

In other embodiments, the polypeptide is an antibody comprising (a) a heavy chain comprising said VH region, and a human hinge, CH1, CH2, and CH3 regions from an IgG1, IgG2, IgG3 or IgG4 subtype; and (b) a light chain comprising said VL region, and either a human kappa CL or human lambda CL.

Certain embodiments provide a purified monoclonal antibody that specifically binds to a Staphylococcal Coa polypeptide, wherein the purified monoclonal antibody is the 5A10, 8E2, 3A6, 7E2, 3F6, 1F10, 6D11, 3D11, 5A11, 1B10, 4C1, 2F2, 8D4, 7D11, 2C3, 4C5, 6B2, 4D5, 2B8, 11H7, 6C10.19 or 6C4.15 monoclonal antibody.

In some aspects, the purified polypeptide does not consist of the mouse monoclonal antibody that is 4H9.20, 5D5.4, 4B10.44, 3B3.14, 7H4.25, 2A3.1, 2H10.12, 6D1.22, 6C4.15, 6C10.19, 8C2.9, and 4F1.7. In other embodiments the purified polypeptide is not an isolated mouse monoclonal antibody.

Other embodiments provide a pharmaceutical composition comprising one or more purified Coa binding polypeptide. In some embodiments, the pharmaceutical composition provides a single unit dose of the purified polypeptide in a sealed container. The pharmaceutical composition may comprise at least a second anti-bacterial agent including, but not limited to, an antibiotic, a Staphylococcal vaccine composition or a polypeptide that specifically binds to a second Staphylococcal protein.

Certain embodiments, provide a polynucleotide comprising a nucleic acid sequence encoding a Coa binding polypeptide.

Other embodiments provide an expression vector comprising a nucleic acid sequence encoding a Coa binding polypeptide operably linked to an expression control sequence. Some embodiments provide a host cell comprising the expression vector.

Embodiments also provide a method manufacturing a Coa binding polypeptide comprising expressing a nucleic acid sequence encoding the polypeptide operably linked to an expression control sequence in a host cell.

Embodiments also provide for the use of Coa antibodies in methods and compositions for the treatment of bacterial and/or staphylococcal infection. In certain embodiments, compositions are used in the manufacture of medicaments for the therapeutic and/or prophylactic treatment of bacterial infections, particularly staphylococcus infections.

Furthermore, in some embodiments there are methods and compositions that can be used to treat (e.g., limiting staphylococcal abscess formation and/or persistence in a subject) or prevent bacterial infection.

Certain aspects are directed to methods of reducing *Staphylococcus* infection or abscess formation comprising administering to a patient having or suspected of having a *Staphylococcus* infection an effective amount of one or more purified antibodies that specifically bind a Coa polypeptide. The antibody can be a purified polyclonal antibody, a purified monoclonal antibody, a recombinant polypeptide, or a fragment thereof. In certain aspects the antibody is humanized or human. In still further aspects the antibody is a recombinant antibody segment. In certain aspects a monoclonal antibody includes one or more of 5A10, 8E2, 3A6, 7E2, 3F6, 1F10, 6D11, 3D11, 5A11, 1B10, 4C1, 2F2, 8D4, 7D11, 2C3, 4C5, 6B2, 4D5, 2B8, 1H7, 6C10.19 or 6C4.15. An antibody can be administered at a dose of 0.1, 0.5, 1, 5, 10, 50, 100 mg or µg/kg to 5, 10, 50, 100, 500 mg or µg/kg, or any range derivable therein. The recombinant antibody segment can be operatively coupled to a second recombinant antibody segment. In certain aspects the second recombinant antibody segment binds a second Staphylococcal protein. The method can further comprise administering a second antibody that binds a second Staphylococcal protein. In certain aspects the method further comprises administering an antibiotic.

Embodiments are directed to monoclonal antibody polypeptides, polypeptides having one or more segments thereof, and polynucleotides encoding the same. In certain aspects a polypeptide can comprise all or part of the heavy chain variable region and/or the light chain variable region of Coa-specific antibodies. In a further aspect, a polypeptide can comprise an amino acid sequence that corresponds to a first, second, and/or third complementary determining regions (CDRs) from the light variable chain and/or heavy variable chain of a Coa-specific antibody.

In still further aspects, embodiments provide a hybridoma cell line that produces a monoclonal antibody of the embodiments. In embodiments the hybridoma cell line is a line that produces the 5A10, 8E2, 3A6, 7E2, 3F6, 1F10, 6D11, 3D11, 5A11, 1B10, 4C1, 2F2, 8D4, 7D11, 2C3, 4C5, 6B2, 4D5, 2B8, 1H7, 6C10.19 or 6C4.15 monoclonal antibody. In a further aspect, 1, 2, and/or 3 CDRs from the light and/or heavy chain variable region of a MAb can be comprised in a humanized antibody or variant thereof.

Certain aspects are directed to methods of treating a subject having or suspected of having a *Staphylococcus* infection comprising administering to a patient having or suspected of having a *Staphylococcus* infection an effective amount of a purified antibody or polypeptide that specifically binds a Coa polypeptide.

In a further aspect methods are directed to treating a subject at risk of a *Staphylococcus* infection comprising administering to a patient at risk of a *Staphylococcus* infection an effective amount of an antibody that binds a Coa polypeptide prior to infection with *Staphylococcus*.

Certain embodiments are directed to an antibody or binding polypeptide composition comprising an isolated and/or recombinant antibody or polypeptide that specifically binds a peptide segment as described above. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein.

In additional embodiments, there are pharmaceutical compositions comprising one or more polypeptides or antibodies or antibody fragments that are discussed herein. Such a composition may or may not contain additional active ingredients.

In certain embodiments there is a pharmaceutical composition consisting essentially of a polypeptide comprising one or more antibodies or antibody fragments discussed herein. It is contemplated that the composition may contain non-active ingredients.

Other aspects are directed to pharmaceutical compositions comprising an effective anti-bacterial amount of an antibody that specifically binds to a peptide described above and a pharmaceutically acceptable carrier.

The term "providing" is used according to its ordinary meaning to indicate "to supply or furnish for use." In some embodiments, the protein is provided directly by administering a composition comprising antibodies or fragments thereof that are described herein.

The subject typically will have (e.g., diagnosed with a persistent staphylococcal infection), will be suspected of having, or will be at risk of developing a staphylococcal infection. Compositions include Coa-binding polypeptides in amounts effective to achieve the intended purpose— treatment or protection of Staphylococcal infection. The term "binding polypeptide" refers to a polypeptide that specifically binds to a target molecule, such as the binding of an antibody to an antigen. Binding polypeptides may but need not be derived from immunoglobulin genes or fragments of immunoglobulin genes. More specifically, an effective amount means an amount of active ingredients necessary to provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods described herein, an effective amount or dose can be estimated initially from in vitro, cell culture, and/or animal model assays. For example, a dose can be formulated in animal models to achieve a desired response. Such information can be used to more accurately determine useful doses in humans.

Compositions can comprise an antibody that binds Coa. An antibody can be an antibody fragment, a humanized antibody, a monoclonal antibody, a single chain antibody or the like. In certain aspects, the Coa antibody is elicited by providing a Coa peptide or antigen or epitope that results in the production of an antibody that binds Coa in the subject. The Coa antibody is typically formulated in a pharmaceutically acceptable composition. The Coa antibody composition can further comprise at least 1, 2, 3, 4, 5, 6, 7, 8, 9, 10, 11, 12, 13, 14, 15, 16, 17, 18, or 19 for more staphylococcal antigens or immunogenic fragments thereof. Staphylococcal antigens include, but arc not limited to all or a segment of Eap, Ebh, Emp, EsaB, EsaC, EsxA, EsxB, IsdA, IsdB, SdrC, SdrD, SdrE, ClfA, ClfB, Coa, Hla (e.g., H35 mutants), IsdC, SasF, vWa, SpA and variants thereof (See U.S. Provisional Application Ser. Nos. 61/166,432, filed Apr. 3, 2009; 61/170,779, filed Apr. 20, 2009; and 61/103,196, filed Oct. 6, 2009; each of which is incorporated herein by reference in their entirety), vWh, 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter. IsaA/PisA, laminin receptor, Lipase GehD, MAP. Mg2+ transporter, MHC II analogue (U.S. Pat. No. 5,648,240), MRPII, Npase, RNA III activating protein (RAP), SasA, SasB, SasC, SasD, SasK, SBI, SdrF(WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). The staphylococcal antigen, or immunogenic fragment or segment can be administered concurrently with the Coa antibody. The staphylococcal antigen or immunogenic fragment and the Coa antibody can be administered in the same or different composition and at the same or different times. The composition may comprises multiple (e.g., 2, 3, 4. or more) Coa antibodies that bind Coa polypeptides from multiple strains of S. aureus.

The Coa antibody composition can further comprise antibodies, antibody fragments or antibody subfragments to at least 1, 2, 3, 4, 5, 6, 7, 8, 9, 10, 11, 12, 13, 14, 15, 16, 17, 18, or 19 of more (or any range derivable therein) staphylococcal antigens or immunogenic fragments thereof. Staphylococcal antigens to which such antibodies, antibody fragments of antibody subfragments are directed include, but are not limited to all or a segment of Eap, Ebh, Emp, EsaB, EsaC, EsxA, EsxB, IsdA, IsdB, SdrC, SdrD, SdrE, ClfA, ClfB, Coa, Hla (e.g., H35 mutants), IsdC, SasF, vWa, SpA and variants thereof (See U.S. Provisional Application serial numbers 61/166,432, filed Apr. 3, 2009; 61/170,779, filed Apr. 20, 2009; and 61/103,196, filed Oct. 6, 2009; each of which is incorporated herein by reference in their entirety), vWh, 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC 11 analogue (U.S. Pat. No. 5,648,240), MRPII, Npase, RNA III activating protein (RAP), SasA, SasB, SasC, SasD, SasK, SBI, SdrF(WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). The antibodies, antibody fragments or antibody subfragments to other staphylococcal antigens or immunogenic fragments thereof can be administered concurrently with the Coa antibody. The antibodies, antibody fragments or antibody subfragments to other staphylococcal antigens or immunogenic fragments thereof can be administered in the same or different composition to the Coa antibody and at the same or different times.

Embodiments include compositions that contain or do not contain a bacterium. A composition may or may not include an attenuated or viable or intact staphylococcal bacterium. In certain aspects, the composition comprises a bacterium that is not a Staphylococci bacterium or does not contain Staphylococci bacteria. In certain embodiments a bacterial composition comprises an isolated or recombinantly expressed Coa antibody or a nucleic acid encoding the same. In still further aspects, the Coa antibody is multimerized, e.g., a dimer, a trimer, a tertramer, etc.

In certain aspects, a peptide or an antigen or an epitope can be presented as multimers of 1, 2, 3, 4, 5, 6, 7, 8, 9, 10 or more peptide segments or peptide mimetics.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Compositions such as antibodies, peptides, antigens, or immunogens may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated.

The term "Coa antibody" refers to an antibody that specifically binds Coa proteins from staphylococcus bacteria. In certain embodiments the antibody may bind a specific Coa protein from a particular staphylococcus bacteria strain.

In further aspects a composition may be administered more than one time to the subject, and may be administered 1, 2, 3, 4, 5, 6, 7, 8, 9, 10, 15, 20 or more times (or any range derivable therein). The administration of the compositions include, but is not limited to oral, parenteral, subcutaneous and intravenous administration, or various combinations thereof, including inhalation or aspiration.

Compositions are typically administered to human subjects, but administration to other animals that are capable of providing a therapeutic benefit against a staphylococcus bacterium are contemplated, particularly cattle, horses, goats, sheep, birds and other domesticated animals. In further aspects the staphylococcus bacterium is a Staphylococcus aureus. In still further aspects, the methods and compositions may be used to prevent, ameliorate, reduce, or treat infection of tissues or glands. Other methods include, but are not limited to prophylactically reducing bacterial burden in a subject not exhibiting signs of infection, particularly those subjects suspected of or at risk of being colonized by a target bacteria, e.g., patients that are or will be at risk or susceptible to infection during a hospital stay, treatment, and/or recovery.

Still further embodiments include methods for providing a subject a protective or therapeutic composition against a staphylococcus bacterium comprising administering to the subject an effective amount of a composition including (i) a Coa antibody; or, (ii) a nucleic acid molecule encoding the same, or (iii) administering an Coa antibody with any combination or permutation of bacterial proteins described herein.

The embodiments in the Example section are understood to be embodiments that are applicable to all aspects of the invention, including compositions and methods.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIG. 1A shows an illustration of the primary structure of coagulase from S. aureus Newman ($Coa_{NM}$), which was purified via an N-terminal $His_6$ tag from E. coli. $Coa_{NM}$ encompasses the D1 and D2 domains involved in prothrombin binding, the linker (L) domain and the Repeat (R) domain, which is comprised of tandem repeats of a 27 residue peptide sequence that binds to fibrinogen. In addition to $Coa_{NM}$, the $D1_{Coa}$, $D2_{Coa}$, $D12_{Coa}$, $L_{Coa}$, and $R_{Coa}$ domains as well as a construct of $D1_{Coa}$ without amino acids 1-18, $D1_{\Delta1-18}$, were purified with N-terminal $His_6$ tags. FIG. 1B shows an an illustration of the regions of coagulase targeted by Coa-specific monoclonal antibodies 5D5, 8C2, 6C10, 3B3, 6C4, and 7H4.

FIG. 7C).

FIGS. 8A-D: Alignment of Coa sequences from USA300 (SEQ ID NO: 1), N315 (SEQ ID NO: 2), MRSA252 (SEQ ID NO: 4), MW2 (SEQ ID NO: 3), and WIS (SEQ ID NO: 5).

DETAILED DESCRIPTION OF THE INVENTION

*Staphylococcus aureus* is a commensal of the human skin and nares, and the leading cause of bloodstream, skin and soft tissue infections (Klevens et al., 2007). Recent dramatic increases in the mortality of staphylococcal diseases are attributed to the spread of methicillin-resistant S. aureus (MRSA) strains often not susceptible to antibiotics (Kennedy et al., 2008). In a large retrospective study, the incidence of MRSA infections was 4.6% of all hospital admissions in the United States (Klevens et al., 2007). The annual health care costs for 94,300 MRSA infected individuals in the United States exceed $2.4 billion (Klevens et al., 2007). The current MRSA epidemic has precipitated a public health crisis that needs to be addressed by development of a preventive vaccine (Boucher and Corey, 2008). To date, an FDA licensed vaccine that prevents *S. aureus* diseases is not available.

Coagulase (Coa) is an important virulence factor in the pathogenesis of staphylococcal sepsis. The conversion of fibrinogen to fibrin by the Coa:prothrombin complex enables *Staphylococcus aureus* to evade immune defenses and disseminate throughout the body. Humoral immunity toward Coa is protective in a murine sepsis model. Previous work demonstrated that there are protective epitopes in both the N- and C-terminus and that there is type-specific immunity, attributable to the genetic variation in the N-terminus of Coa among strains.

The inventors describe here staphylococcal coagulase-binding antibodies and the antigen binding determinants thereof. In particular, a panel of monoclonal antibodies were generated against Coa and characterized based on their affinity for individual domains of the protein and their disturbance of clotting. Based on in vitro characteristics, several monoclonal antibodies were tested for protection in a murine sepsis model resulting in the identification of a protective epitope in the conserved portion of the N-terminus. Importantly, antibodies targeting this epitope are able, when administered to animals, to reduce Staphylococcal sepsis following challenge with virulent *S. aureus*. Because these molecules are able to block the prothrombin-activating effects of Coa, such antibodies may also enhance host immune response following staphylococcal infection. Thus, the Coa-binding molecules of the embodiments offer a new and effective avenue to treat or prevent staphylococcal disease.

I. Coagulase Polypeptides

Figure 1A:
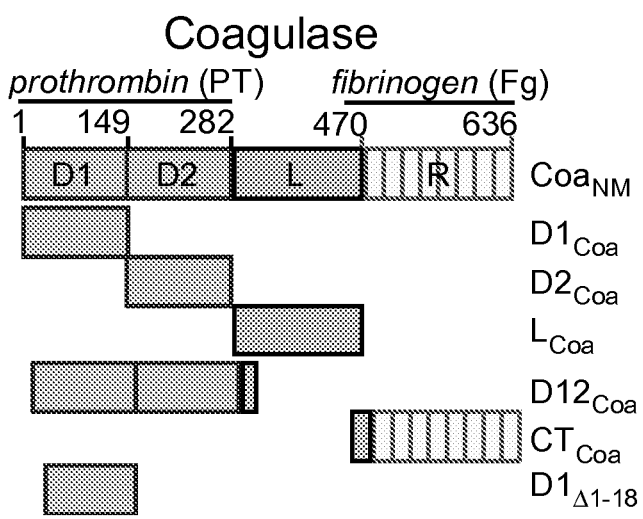
FIGS. 1A-1B: Illustrations of the primary structure of coagulase from S. aureus Newman ($Coa_{NM}$) and the regions of coagulase targeted by certain Coa-specific monoclonal antibodies.

Certain aspects of the embodiments concern coagulase (Coa) polypeptides. An illustration of the primary structure of Coa from *S. Aureus* Newman ($Coa_{NM}$) is provided in FIG. 1A. Nucleic acid sequences for Coa from eight *S. aureus* strains are provided in SEQ ID NOs: 1-8 as follows: USA300 (SEQ ID NO: 1), N315 (SEQ ID NO: 2), MW2 (SEQ ID NO: 3), MRSA252 (SEQ ID NO: 4), WIS (SEQ ID NO: 5), MU50 (SEQ ID NO: 6), 85/2082 (SEQ ID NO: 7), and Newman (SEQ ID NO: 8). An alignment of Coa sequences from USA300 (SEQ ID NO: 1), N315 (SEQ ID NO: 2), MRSA252 (SEQ ID NO: 4), MW2 (SEQ ID NO: 3), and WIS (SEQ ID NO: 5) is provided in FIG. 6.

Coagulase interacts with host prothrombin through its N-terminal domains, D1 and D2. The three-helix bundles of D1 and D2 share structural similarity but are poorly conserved at the sequence level [66]. The first 150 amino acids comprise the D1 domain [68]. The amino-terminal tetrapeptide of Coa inserts into the activation pocket of prothrombin and forms a salt bridge with prothrombin Asp194 [66]. The first of two high-affinity binding interactions between Coa and prothrombin occurs through a hydrophobic surface groove in D1 with the 148 loop of prothrombin [66]. $SC_{150-282}$ comprises the D2 domain [68]. The second high-affinity binding interaction is between the side chain of Tyr76 of the prothrombin exosite I and D2 alpha helices [66]. Coa forms a dimer in solution, with each monomer binding one molecule of prothrombin [66]. A complex formed by prothrombin and a recombinant construct of the D1D2 domain ($SC_{1-325}$) is able to bind fibrinogen through a distinct interaction from the substrate binding exosite on prothrombin [133].

Two other domains of Coa are less well understood. Following D2, there is a highly conserved Linker (L) region with unknown function [77]. Near the C-terminus is a region of tandem repeats of a 27 amino acid peptide, and the number of repeats varies among strains [77]. The repeat region is thought to be responsible for high affinity binding to fibrinogen[133,214].

The gene encoding Coa (coa) is found on all *S. aureus* chromosomes, yet it is one of the most variable proteins, with twelve known types (Watanabe et al 2005, Watanabe et al 2009). The majority of variability among Coa alleles resides in the D1 and D2 domains. The linker region is relatively conserved with 86.7% identity among serotypes (Watanabe et al 2005). Of note, the amino terminal end of mature Coa, i.e. the first seven residues following the signal peptidase cleavage site, activate prothrombin and these residues are conserved among all strains analyzed [68]. The C-terminal tandem repeats of a 27 residue peptide vary in number from five to nine but have greater than 90% identity among serotypes (Watanabe et at 2005). Antibodies that recognize epitopes in $SC_{1-282}$ are necessary to block the enzymatic activities of the Coa-prothrombin complex [215]. In vivo, antibodies against the C-terminal repeats also confer protection [215], though the mechanism of protection is not yet clear.

Coa polypeptides can be used as subunit vaccines and raise humoral immune responses and confer protective immunity against *S. aureus* challenge. In certain embodiments, polyvalent vaccines targeting Coa variation across multiple S. aurueus strains are contemplated. This embodiment is discussed in a U.S. Provisional Patent Application filed on Apr. 26, 2012 entitled "STAPHYLOCOCCAL COAGULASE ANTIGENS AND METHODS OF THEIR USE" in the names of Molly McAdow, Andrea DeDent, Alice Cheng, Carla Emolo, Dominique Missiakas, Olaf Schneewind, which is hereby incorporated by reference in its entirety.

II. Proteinaceous Compositions

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Codon Table, below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |

Codon Table

| Amino Acids | | | Codons |
|---|---|---|---|
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an antibody that binds Coa, and may be used in combination with other staphylococcal proteins or protein-binding antibodies described herein.

A. Polypeptides and Polypeptide Production

Embodiments involve polypeptides, peptides, and proteins and immunogenic fragments thereof for use in various aspects described herein. For example, specific antibodies are assayed for or used in neutralizing or inhibiting Staphylococcal infection. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects an immunogenic Coa fragment comprises substantially all of the D1 and/or D2 domains of a Coa protein isolatable from S. aureus.

Also included in immunogenic compositions are fusion proteins composed of Staphylococcal proteins, or immunogenic fragments of staphylococcal proteins (e.g., Coa). Alternatively, embodiments also include individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM 197.

B. Antibodies and Antibody-Like Molecules

In certain aspects, one or more antibodies or antibody-like molecules (e.g., polypeptides comprsing antibody CDR domains) may be obtained or produced which have a specificity for an Coa. In particular embodiments, one or more antibodies or antibody-like molecules (e.g., polypeptides comprsing antibody CDR domains) may be obtained or produced which have a specificity for the D1 and/or D2 domain of Coa. These antibodies may be used in various diagnostic or therapeutic applications described herein.

As used herein, the term "antibody" is intended to refer broadly to any immunologic binding agent such as IgG, IgM, IgA, IgD and IgE as well as polypeptides comprsing antibody CDR domains that retain antigen binding activity. Thus, the term "antibody" is used to refer to any antibody-like molecule that has an antigen binding region, and includes antibody fragments such as Fab', Fab, F(ab')$_2$, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region. Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al.(2003) describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate Coa-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art): small size: few or no post-transcriptional modifications; and/or easy to produce, express and purify.

The origin of such protein scaffolds can be, but is not limited to, the structures selected among: fibronectin and preferentially fibronectin type Ill domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as SpA binding molecules. Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibiters of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

1. Methods for Generating Antibodies

Methods for generating antibodies (e.g., monoclonal antibodies and/or monoclonal antibodies) are known in the art. Briefly, a polyclonal antibody is prepared by immunizing an animal with a Coa polypeptide or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions or vectors encoding such adjuvants.

Adjuvants that may be used in accordance with embodiments include, but are not limited to, IL-1, IL-2, IL-4, IL-7, IL-12, -interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, N.J.), cytokines such as -interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography, among others.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. In some embodiments, Rodents such as mice and rats are used in generating monoclonal antibodies. In some embodiments, rabbit, sheep or frog cells are used in generating monoclonal antibodies. The use of rats is well known and may provide certain advantages (Goding. 1986, pp. 60 61). Mice (e.g., BALB/c mice) are routinely used and generally give a high percentage of stable fusions.

The animals are injected with antigen, generally as described above. The antigen may be mixed with adjuvant, such as Freund's complete or incomplete adjuvant. Booster administrations with the same antigen or DNA encoding the antigen may occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Generally, spleen cells are a rich source of antibody-producing cells that are in the dividing plasmablast stage. Typically, peripheral blood cells may be readily obtained, as peripheral blood is easily accessible.

In some embodiments, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X63/Ag8, X63 Ag8.653, NS 1/1.Ag 4 1, Sp210 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al. (2002), for a discussion of myeloma expression systems.

One murine myeloma cell is the NS-1 mycloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azascrine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from mycloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in *E. coli*.

C. Antibody and Polypeptide Conjugates

Embodiments provide antibodies and antibody-like molecules against Coa proteins, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging". Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might use astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often used in certain embodiments, and technicium$^{99m}$ and/or indium$^{111}$ are also often used due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fec region have also been disclosed in the literature (O'Shannessy et al., 1987). This approach has been reported to produce diagnostically and therapeutically promising antibodies which are currently in clinical evaluation.

In some embodiments, anti-Coa antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays include, but are not limited to, those described above, including group II-VI, III-V and group IV semiconductors such as ZnS, ZnSe, ZnTc, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

III. Nucleic Acids

In certain embodiments, there are recombinant polynuclcotides encoding the proteins, polypeptides, or peptides described herein. Polynucleotide sequences contemplated include those encoding antibodies to Coa or Coa-binding portions thereof.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., an antibody or fragment thereof) that binds to Coa. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody that binds Coa.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

The particular promoter that is employed to control the expression of a peptide or protein encoding polynucleotide is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

D. Methods of Gene Transfer

Suitable methods for nucleic acid delivery to effect expression of compositions are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945, 100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Through the application of techniques such as these, organelle(s), cell(s), tissue(s) or organism(s) may be stably or transiently transformed.

IV. Methods of Treatment

As discussed above, the compositions and methods of using these compositions can treat a subject (e.g., limiting bacterial load or abscess formation or persistence) having, suspected of having, or at risk of developing an infection or related disease, particularly those related to staphylococci. One use of the compositions is to prevent nosocomial infections by inoculating a subject prior to hospital treatment.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a recipient patient. Treatment or therapy can be an active immune response induced by administration of immunogen or a passive therapy effected by administration of antibody, antibody containing material, or primed T-cells.

As used herein "passive immunity" refers to any immunity conferred upon a subject by administration of immune effectors including cellular mediators or protein mediators (e.g., an polypeptide that binds to Coa protein). An antibody composition may be used in passive immunization for the prevention or treatment of infection by organisms that carry the antigen recognized by the antibody. An antibody composition may include antibodies or polypeptides comprising antibody CDR domains that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to staphylococcus bacteria.

Passive immunity may be imparted to a patient or subject by administering to the patient immunoglobulins (Ig) or fragments thereof and/or other immune factors obtained from a donor or other non-patient source having a known immunoreactivity. In other aspects, an antigenic composition can be administered to a subject who then acts as a source or donor for globulin, produced in response to challenge from the composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat staphylococcus infection. Hyperimmune globulins are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition caused by a staphylococcus pathogen. In certain aspects embodiments include methods of treatment of staphylococcal infection, such as hospital acquired nosocomial infections. In some embodiments, the treatment is administered in the presence of staphylococcal antigens. Furthermore, in some examples, treatment comprises administration of other agents commonly used against bacterial infection, such as one or more antibiotics.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

A. Antibodies and Passive Immunization

Certain aspects are directed to methods of preparing an antibody for use in prevention or treatment of staphylococcal infection comprising the steps of immunizing a recipient with a vaccine and isolating antibody from the recipient, or producing a recombinant antibody. An antibody prepared by these methods and used to treat or prevent a staphylococcal infection is a further aspect. A pharmaceutical composition comprising antibodies that specifically bind Coa and a pharmaceutically acceptable carrier is a further aspect that could be used in the manufacture of a medicament for the treatment or prevention of staphylococcal disease. A method for treatment or prevention of staphylococcal infection comprising a step of administering to a patient an effective amount of the pharmaceutical preparation is a further aspect.

Inocula for polyclonal antibody production are typically prepared by dispersing the antigenic composition (e.g., a peptide or antigen or epitope of Coa or a consensus thereof) in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies. The antibodies can be isolated to the extent desired by well known techniques such as affinity chromatography (Harlow and Lane, *Antibodies: A Laboratory Manual* 1988). Antibodies can include antiserum preparations from a variety of commonly used animals e.g., goats, primates, donkeys, swine, horses, guinea pigs, rats or man. The animals are bled and serum recovered.

An antibody can include whole antibodies, antibody fragments or subfragments. Antibodies can be whole immunoglobulins of any class (e.g., IgG, IgM, IgA, IgD or IgE), chimeric antibodies, human antibodies, humanized antibodies, or hybrid antibodies with dual specificity to two or more antigens. They may also be fragments (e.g., F(ab')2, Fab', Fab, Fv and the like including hybrid fragments). An antibody also includes natural, synthetic or genetically engineered proteins that act like an antibody by binding to specific antigens with a sufficient affinity.

A vaccine can be administered to a recipient who then acts as a source of antibodies, produced in response to challenge from the specific vaccine. A subject thus treated would donate plasma from which antibody would be obtained via conventional plasma fractionation methodology. The isolated antibody would be administered to the same or different subject in order to impart resistance against or treat staphylococcal infection. Antibodies are particularly useful for treatment or prevention of staphylococcal disease in infants, immune compromised individuals or where treatment is required and there is no time for the individual to produce a response to vaccination.

An additional aspect is a pharmaceutical composition comprising two of more antibodies or monoclonal antibodies (or fragments thereof; preferably human or humanized) reactive against at least two constituents of the immunogenic composition, which could be used to treat or prevent infection by Gram positive bacteria, preferably staphylococci, more preferably *S. aureus* or *S. epidermidis*.

B. Combination Therapy

The compositions and related methods, particularly administration of an antibody that binds Coa or a peptide or consensus peptide thereof to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a therapy is used in conjunction with antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example antibiotic therapy is "A" and an antibody therapy that comprises an antibody that binds Coa or a peptide or consensus peptide thereof is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

C. General Pharmaceutical Compositions

In some embodiments, pharmaceutical compositions are administered to a subject. Different aspects may involve administering an effective amount of a composition to a subject. In some embodiments, an antibody that binds Coa or a peptide or consensus peptide thereof may be administered to the patient to protect against or treat infection by one or more bacteria from the *Staphylococcus* genus. Alternatively, an expression vector encoding one or more such antibodies or polypeptides or peptides may be given to a patient as a preventative treatment. Additionally, such compositions can be administered in combination with an antibiotic. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the intravenous, intramuscular, sub-cutaneous, or even intraperitoneal mutes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

V. Examples

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Monoclonal Antibodies that Neutralize Coagulase Activity During *Staphylococcus aureus* Disease Coa Mab specificity and affinity. Mabs were generated against $Coa_{NM}$ and their affinity to Coa was measured (Table 1). The monoclonal antibodies were also tested for binding to an irrelevant protein (IsdA), and those that did not exhibit a specific interaction were eliminated from further study. Because vWbp has some homology to Coa in its N-terminal D1 and D2 domains (Bjerketorp et al 2004, Watanabe et al 2005), binding of Coa monoclonals to vWbp was also tested. None of the Mabs displayed specific binding vWbp.

Figure 1B:
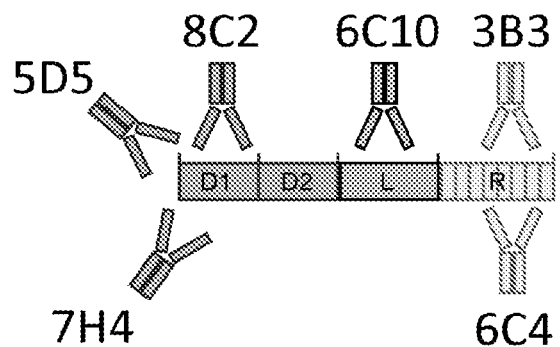

In order to determine the binding site of each Mab on Coa, subdomains representing D1 ($D1_{Coa}$), D2 ($D2_{Coa}$), the first 329 residues including the entire D1D2 domain and part of the linker domain ($D12_{Coa}$), linker ($L_{Coa}$), repeat region ($CT_{Coa}$), and a truncated form of D1 missing the first 18 amino acids ($D1_{\Delta1-18}$) were cloned and expressed in *E. coli* (FIG. 1). Eleven Mabs bound $D12_{Coa}$, all of which specifically recognized $D1_{Coa}$. (Table 1). Two Mabs bound $L_{Coa}$, and none of the Mabs bound $D2_{Coa}$. Two Mabs bound $CT_{Coa}$.

TABLE 1

Biochemical attributes and biological values of Mabs raised against Coa

| Mab | Isotype | $Coa_{NM}$ | $D12_{Coa}$ | $D1_{Coa}$ | $D1_{\Delta1-18}$ | $D2_{Coa}$ | $L_{Coa}$ | $CT_{Coa}$ |
|---|---|---|---|---|---|---|---|---|
| | | Affinity[a] | | | | | | |
| 4H9.20 | IgG1 | 0.04 | 0.01 | 0.01 | < | < | < | < |
| 5D5.4 | IgG1 | 4.06 | 2.55 | 3.94 | 1.03 | < | < | < |
| 6C10.19 | IgG1 | 3.82 | 4.39 | 0.01 | < | < | 6.58 | < |
| 4B10.44 | IgG1 | 0.03 | 0.01 | 0.02 | < | < | < | < |
| 3B3.14 | IgG1 | 3.2 | < | < | < | < | < | 5.25 |
| 7H4.25 | IgG1 | 1.64 | 1.42 | 1.02 | 0.28 | < | 0.01 | < |
| 4F1.7 | IgG1 | 0.68 | 0.05 | 1.01 | 0.1 | < | < | < |
| 8C2.9 | IgG2a | 3.4 | 3.2 | 0.78 | 0.57 | < | < | < |
| 2A3.1 | IgG2a | 0.17 | 0.24 | 0.12 | 0 | < | < | < |
| 5C3.2 | IgG2b | 0.4 | 0.3 | 0.35 | 0.02 | < | < | < |
| 2H10.12 | IgG2b | 2.39 | 2.87 | 2.13 | 0.03 | < | < | < |
| 6D1.22 | IgG2b | 2.79 | 3.28 | 2.13 | 0.03 | < | < | < |
| 6C4.15 | IgG2b | 5.97 | < | < | < | < | < | 6.70 |

[a]Determined by ELISA as the association constant ($K_a$) in $\times 10^{-9}$ M

TABLE 2

Inhibition of clotting of whole blood by *S. aureus* mutant strain vwb in the presence of monoclonal antibodies generated against Coa

| Isotype | Antibody | Fold delay in clotting time (SEM)[a] |
|---|---|---|
| IgG1 | IgG1 control | 1.0 |
| | 4H9.20 | 0.65 (0.18) |
| | 5D5.4 | 2.07 (0.58) |
| | 6C10.19 | 1.00 (0.14) |
| | 4B10.44 | 1.19 (0.15) |
| | 3B3.14 | 1.22 (0.18) |
| | 7H4.25 | 1.63 (0.16) |
| | 4F1.7 | 1.23 (0.14) |
| IgG2a | IgG2a control | 1.0 |
| | 8C2.9 | 1.30 (0.15) |
| | 2A3.11 | 0.83 (0.12) |
| IgG2b | IgG2b control | 1.0 |
| | 5C3.2 | 1.12 (0.22) |
| | 2H10.12 | 1.43 (0.18) |
| | 6D1.22 | 1.08 (0.19) |
| | 6C4.15 | 1.19 (0.15) |

[a]SEM, standard error of the mean as compared to isotype control

Figures 2A, 2B:
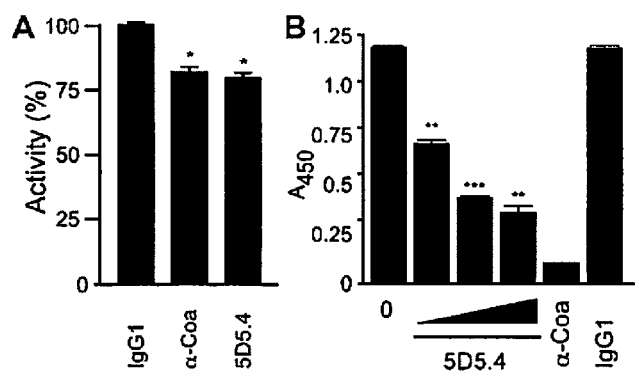
FIGS. 2A-2B: Mab 5D5.4 disrupts Coa-prothrombin activity. (A) Coa prothrombin enzymatic activity was measured with chromogenic substrate S-2238. Following pre-incubation with Mab 5D5.4 polyclonal purified α-Coa, activity was reduced. Statistical analysis was assessed using 1-way ANOVA followed by a post-hoc Dunnett's multiple comparison test. (B) The association of $Coa_{NM}$ with human prothrombin was measured by ELISA and perturbed with increasing concentrations Mab 5D5.4 or control IgG1. Compared to isotype control, *P<0.05, **P<0.01.

Mab 5D5.4 Prevents the Formation of Coa•prothrombin Complexes. Mab 5D5.4, which caused the most pronounced delay in clotting of all Mabs tested, was examined for its ability to disrupt Coa•prothrombin activity. Mixture of recombinant Coa with 5D5.4 prior to the addition of purified human prothrombin and the S-2238 chromogenic substrate Inhibition of Blood Coagulation by Monoclonal Antibodies. Coa-specific Mabs were screened for their ability to inhibit clotting of calcium-chelated mouse blood by *S. aureus* isogenic mutant vwb, which coagulates blood more slowly than wild-type (Cheng et al). Isolated *S. aureus* Newman vwb mutants ($1 \times 10^6$ CFU) were mixed with Mabs (3 µM) and added to mouse blood. Samples were monitored at timed intervals for coagulation. Compared to blood incubated with isotype controls, several Mabs prolonged the coagulation time. Antibodies that generated the greatest delay in time to clotting were 5D5.4, 714.25, and 8C.9 (Table 2). All three of these antibodies recognize $D1_{Coa}$ (Table 1), consistent with our previous observation that polyclonal rabbit serum that recognizes $D12_{Coa}$, but not those that recognize $CT_{Coa}$, delay clotting of whole mouse blood [215]. Antibodies that recognized $CT_{Coa}$ (6C4.15, 3B3.14) and the antibody that recognized $L_{Coa}$ (6C10.27) did not cause delays in staphylococcl coagulation (Table 2).

resulted in reduced enzymatic activity (IgG1 vs. 5D5.4, P<0.05) (FIG. 2A). Interestingly, treatment with 7H4.25 and 8C2.9, which caused delays in the coagulation of whole blood, did not significantly reduce the enzymatic activity in this assay (IgG1 vs. 7H4.25, P>0.05; IgG2a vs. 8C2.9, P>0.05) (data not shown).

To test whether 5D5.4 prevents the association of Coa to prothrombin, Maxisorb ELISA plates (Nunc) were coated with recombinant Coa and incubated with antibodies prior to incubation with human prothrombin. Prothrombin binding was detected by HRP-conjugated secondary antibody. 5D5.4 reduced the binding of prothrombin to Coa 3.3-fold at a concentration of 200 nM (IgG1 vs. 5D5.4, P<0.01) (FIG. 2B). These results indicate that 5D5.4 prevents the formation of the Coa•prothrombin complex, resulting in reduced enzymatic activity.

Four amino acids at the N-terminal end of Coa activate prothrombin [66]. To investigate whether any of the monoclonal antibodies bind D1 in a manner dependent on the N-terminus, a recombinant construct consisting of the D1$_{Coa}$ domain but lacking the first 18 amino acids (D1$_{\Delta 1-18}$) was expressed in E. coli and purified (FIG. 1). The association constant of each Mab that recognizes D1$_{Coa}$, was measured for association with the truncated protein. All of the Mabs, with the exception of 8C2.9, had at least a one-log reduction in association constant for D1$_{\Delta 1-18}$ (Table 1). Of note, 5D5.4 4F1.7, and 7H4.25 recognize Coa$_{USA3000}$, which is the same serotype as Coa$_{NM}$, albeit with lower affinity than Coa $_M$ (Table 3). Several antibodies also recognize the recombinant Coa of other S. aureus clinical isolates. 5D5.4 interacted with Coa$_{N35}$, Coa$_{WIS}$ and Coa$_{MW2}$ (Table 3), and 7H4.25 interacted with all serotypes of Coa albeit with low affinity (Table 3).

TABLE 3

Affinity of Mabs toward Coa of different strains

| Mab[a] | Domain[b] | Coa$_{Nm}$ | Coa$_{USA300}$ | Coa$_{85/2082}$ | Coa$_{N315}$ | Coa$_{MRSA}$ | Coa$_{MW2}$ | Coa$_{WIS}$ |
|---|---|---|---|---|---|---|---|---|
| 3B3.14 | R | 3.20 | 2.11 | 2.40 | 4.86 | 4.60 | 2.61 | 3.62 |
| 2H10.12 | D1 | 2.39 | 3.20 | < | < | < | < | < |
| 5D5.4 | D1 | 4.06 | 4.20 | < | 0.21 | < | 5.89 | 6.16 |
| 8C2.9 | D1 | 3.4 | 0.7 | < | 0.05 | 0.04 | < | < |
| 4F1.7 | D1 | 0.68 | 0.1 | < | 0 | < | < | < |
| 6C10.19 | L | 3.82 | 6.66 | < | 7.13 | < | < | < |
| 6C4.15 | R | 5.97 | 2.98 | 4.71 | 4.79 | 4.94 | 4.99 | 5.78 |
| 7H4.25 | D1 | 1.64 | 0.35 | 0.20 | 0.11 | 0.13 | 0.06 | 0.10 |

Figures 3A, 3B:
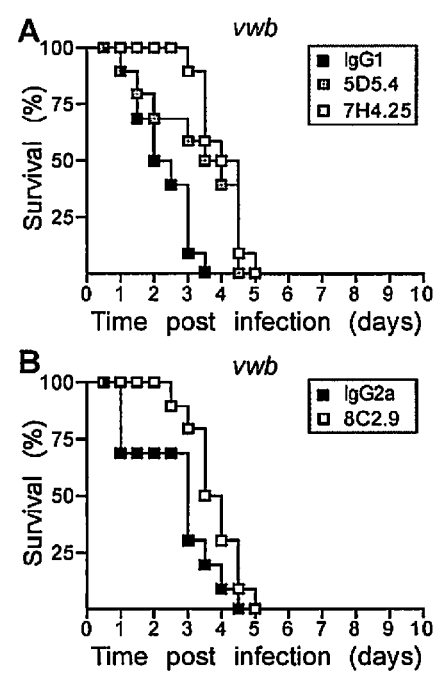
FIGS. 3A-3B: Protective value of coagulation-neutralizing antibodies. Monoclonal antibodies 5D5.4, 7H4.25, or IgG1 isotype control (A) or 8C2.9 or IgG2a isotype control (B) were injected at a concentration of 5 mg·kg$^{-1}$ body weight into the peritoneal cavity of naïve BALB/c mice. Passively immunized mice were challenged by intravenous injection with S. aureus Newman isogenic mutant vwb (2×10$^8$ CFU) and survival of animals was monitored over 10 days.

[a]Mouse monoclonal antibodies were purified from isolated hybridoma clones
[b]Coa domain recognized by each Mab (Table 1)
[c]Affinity was determined by ELISA as the association constant (K$_a$) in $10^9$ M$^{-1}$ for each protein.

recognized D1$_{Coa}$ with an affinity of 3.94 nM$^{-1}$ but interacted with D1$_{\Delta 1-18}$ with an affinity of 1.03 nM$^{-1}$. This observation, combined with its direct inhibition on the enzymatic activity of Coa, supports the idea that 5D5.4 recognizes an epitope near the N-terminus that may conserved among various Coa serotypes of different strains of S. aureus Reduction in Staphylococcal Sepsis by Coa Mabs. Previous results have suggested that type-specific immunity results from antibodies that recognize D12$_{Coa}$ and neutralize Coa activity [215]. To test whether Coa Mabs that delay clotting in vitro confer protective immunity against S. aureus in vivo, mice received intraperitoneal injections of monoclonal antibodies or an isotype control preparation. Six hours later, mice were infected by retro-orbital injection with S. aureus strain vwb (2×10$^8$ CFU). Mice were monitored for survival over a ten-day observation period, and protection was assessed by the Log rank test (FIG. 3). Two antibodies, Mab 5D5.4 and 7H4.25 conferred significant delay in time to death compared to the IgG1 control (IgG1 vs. 5D5.4, P<0.05; IgG1 vs. 7H4.25, P<0.001) (FIG. 3A). Monoclonal antibody 8C2.9, which delayed clotting in vitro, did not protect mice against a lethal dose of S. aureus strain vwb (IgG2a vs. 8C2.9, P=0.06) (FIG. 3B). These data are consistent with the hypothesis that protective immunity toward the D1 domain correlates with neutralization of coagulation activity. However, perturbation of in vitro coagulation is not sufficient to garner protective efficacy.

Figure 4:
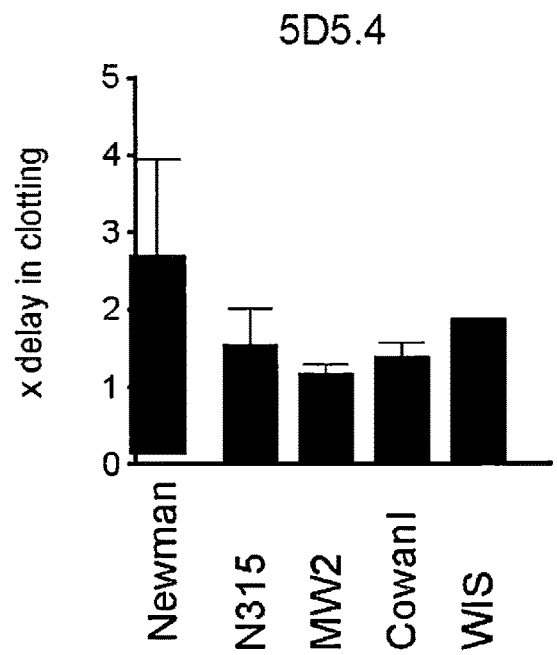
FIG. 4: Cross-protection of Mab 5D5.4 toward infection by clinical isolates of different Coa serotypes. Monoclonal antibody 5D5.4 or IgG1 isotype control was injected at a concentration of 5 mg·kg$^{-1}$ body weight into the peritoneal cavity of naïve BALB/c mice. Passively immunized mice were challenged by intravenous injection with S. aureus strains (A) N315 (1×10$^8$ CFU) or (B) MW2 (2×10$^8$ CFU), and survival of animals was monitored over 10 days.

Cross-Reactivity by Coa Mabs. Type-specific immunity toward Coa is derived from neutralizing antibodies that recognize D1$_{Coa}$ [215]. However, the N-terminal seven amino acids of Coa are conserved among Coa types [68]. To investigate whether the Mabs generated against recombinant Coa of strain Newman cross-react with Coa from other serotypes, Maxisorb ELISA plates (Nunc) were coated with Coa from epidemic strains USA300 (Coa type III), 85/2082 (Coa type IV), N315 (Coa type II), MRSA252 (Coa type IV), MW2 (Coa type VII), and WIS (Coa type VII). The association of Mabs to these alleles was measured (Table 3). The affinity of most antibodies to the other alleles of Coa is lower than the affinity to Coa$_{NM}$. 2H10.12, 5D5.4, 8C2.9, To investigate whether mAb 5D5.4 has cross-protective effect in delaying the coagulation by strains of other coagulase serotypes, preparations of S. aureus strains Newman, N315, MW2, CowanI, and WIS (1×10$^6$ CFU) were mixed with mAbs (3 µM final) and added to citrate-treated rabbit plasma. Plasma was incubated at 37° C. and monitored over time. mAb 5D5.4 failed to delay clotting by strains of any other coagulase serotype (FIG. 4).

Figures 5A, 5B, 5C, 5D:
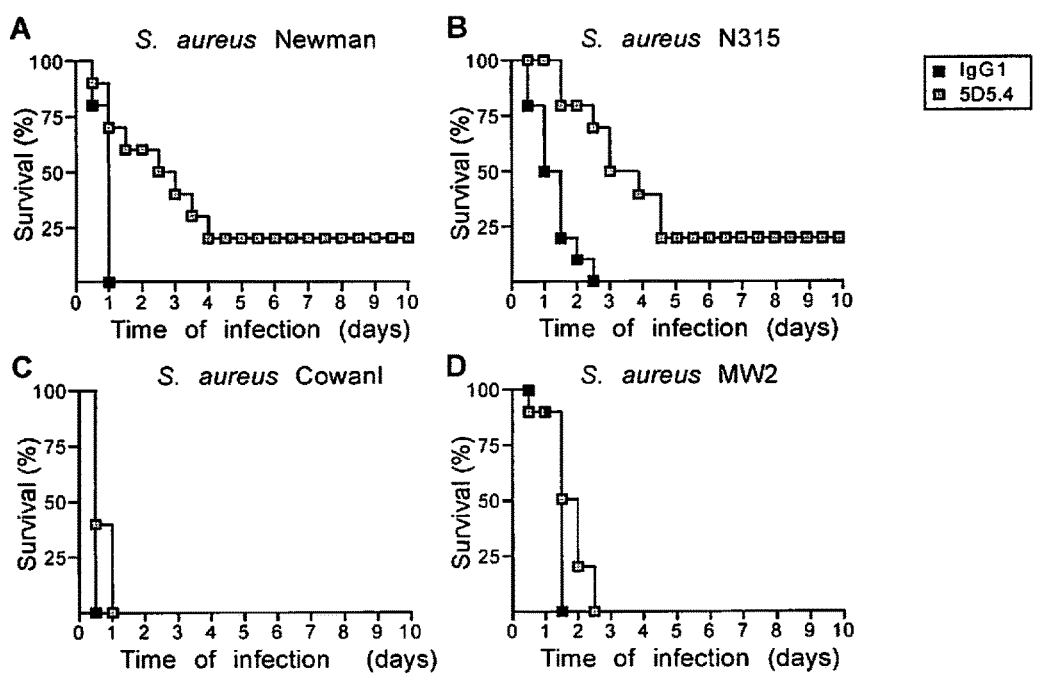
FIGS. 5A-D: Mice received intraperitoneal injections of 5D5.4 or an IgG1 isotype control, and were subsequently infected with a lethal dose of S. aureus strains Newman (Coa type III) (FIG. 5A), N315 (Coa type II) (FIG. 5B), CowanI (Coa type IV) (FIG. 5C), or MW2 (Coa type VII) (FIG. 5D), and were monitored over a ten-day observation period to assess their protective role. 5D5.4 treatment resulted in a delay in time-to-death for animals challenged with strains Newman (IgG1 vs 5D5.4, P<0.01), N315 (IgG vs. 5D5.4, P<0.05), CowanI (IgG1 vs. 5D5.4, P<0.05) or MW2 (IgG1 vs. 5D5.4, P<0.05).

The possibility that candidate Mabs may recognize an epitope conserved by all Coa serotypes was investigated. For example, 5D5.4 provided broad protection in animals but not in the clotting assay. Indeed, mice received intraperitoneal injections of 5D5.4 or an IgG1 isotype control, and were subsequently infected with a lethal dose of S. aureus strains Newman (Coa type III), N315 (Coa type II), CowanI (Coa type IV), or MW2 (Coa type VII), and were monitored over a ten-day observation period to assess their protective role (FIG. 5). 5D5.4 treatment resulted in a delay in time-to-death for animals challenged with strains Newman (IgG1 vs 5D5.4, P<0.01), N315 (IgG vs. 5D5.4, P<0.05), CowanI (IgG vs. 5D5.4, P<0.05) or MW2 (IgG1 vs. 5D5.4, P<0.05). Together, these data suggest that by recognizing a conserved epitope within the Coa D1 domain, 5D5.4 provides protection against lethal disease by strains with the three most common Coa serotypes in North America [144].

Role of Coa$_{CT}$ Monoclonal Antibodies in Immunity. The C-terminal domains of Coa display less sequence variation among staphylococcal isolates [68]. We isolated two monoclonal antibodies that recognize CT$_{Coa}$, 3B3.14 and 6C4.15 (Table 1). ELISA was used to investigate whether the Mabs generated against CT$_{Coa}$ of strain Newman cross-react with Coa from other strains (Table 3). Consistent with our expectations, 3B3.14 and 6C4.15 recognize Coa$_{USA300}$, Coa$_{85/2082}$, Coa$_{N315}$, Coa$_{MW2}$, and Coa$_{WIS}$.

Polyclonal antisera that recognize CT$_{Coa}$ (αCT$_{Coa}$) block the interaction between CT$_{Coa}$ and fibrinogen and confer protection against lethal staphylococcal disease [68,215]. Therefore, it is of interest whether any of the Mabs possess these activities. To test whether 3B3.14 and 6C4.15 inhibit the association of CT$_{Coa}$ with fibrinogen, Maxisorb ELISA plates (Nunc) were coated with CT$_{Coa}$ and incubated with Mabs or isotype controls prior to incubation with human fibrinogen. Fibrinogen binding was detected by HRP-conjugated secondary antibody. 3B3.14 reduced the binding of fibrinogen to $CT_{Coa}$ by 54% at a concentration of 1 µM (IgG1 vs. 3B3.14, P<0.001) (FIG. 6A). 6C4.15 did not disrupt the association of $CT_{Coa}$ to fibrinogen in this assay (FIG. 6B).

Figures 6A, 6B, 6C, 6D:
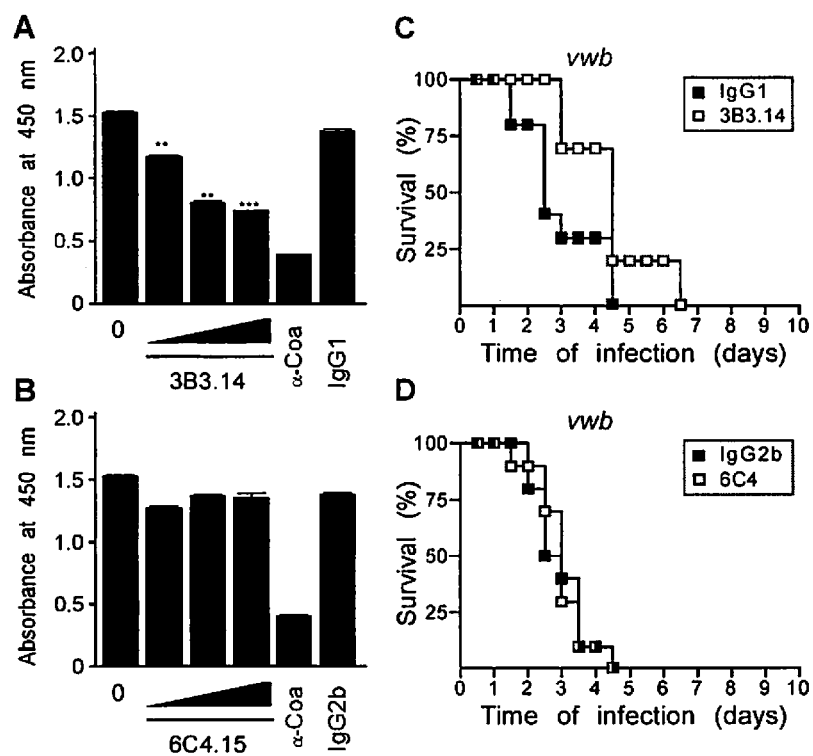
FIGS. 6A-6D: Monoclonal antibodies that recognize $CT_{Coa}$. (A-B) The association of $CT_{Coa}$ with human fibrinogen was measured by ELISA and perturbed with increasing concentrations Mab 3B3.14 or control IgG1 (A) or Mab 6C4.15 or control IgG2b (B). Compared to isotype control, *P<0.05, P<0.01, *P<0.001. (C-D) Monoclonal antibody 3B3.14 or IgG1 control (C) or 6C4.15 or IgG2b (D) was injected at a concentration of 5 mg·kg$^{-1}$ body weight into the peritoneal cavity of naïve BALB/c mice. Passively immunized mice were challenged by intravenous injection with S. aureus strain vwb and survival of animals was monitored over 10 days.

To investigate the effect of Mabs that recognize $Coa_{CT}$ on survival during staphylococcal disease, mice received intraperitoneal injections of 3B3.14, 6C4.15, or their isotype controls, and were challenged with $2\times10^8$ CFU of the S. aureus Newman variant with a deletion of vwb (FIGS. 6C-6D). Animals were monitored over a ten-day observation period to assess the contribution of antibody treatment on survival. Treatment with 3B3.14 or 6C4.15 did not result in a significant delay in time to death (P>0.05) (FIGS. 6C-6D). Thus, neither of the Mabs generated here retain the protective value of the polyclonal $\alpha CT_{Coa}$ antibodies that had been raised in rabbits.

Figures 7A, 7B, 7C, 7D:
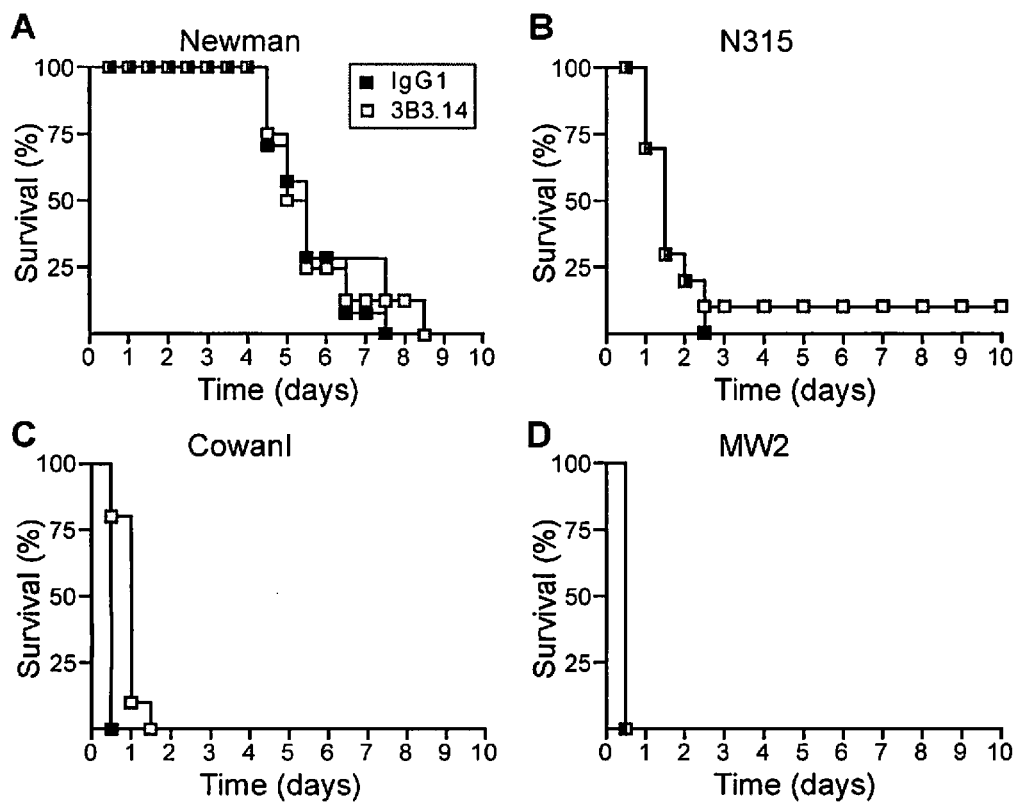
FIGS. 7A-D: Mice received intraperitoneal injections of 3B3.14 or IgG1 isotype control, and were subsequently infected with a lethal dose of S. aureus clinical isolate USA300 (Coa type III) (FIG. 7A), N315 (Coa type II) (FIG. 7B), CowanI (Coa type IV) (FIG. 7C), or MW2 (Coa type VII) (FIG. 7D). and were monitored over a ten-day observation period to assess their protective role. 3B3.14 did not protect mice against challenge with the wildtype Newman (IgG1 vs. 3B3.14 p>0.05 FIG. 7A), N315 (IgG1 vs. 3B3.14 p.0.05 FIG. 7B), or MW2 (IgG1 vs. 3B3.14 p.0.05 FIG. 7D). 3B3.14 provided a modest delay in time to death following challenge with strain CowanI (IgG1 vs. 3B3.14 p<0.001.

$CT_{Coa}$ is relatively conserved among strains of S. aureus, to investigate whether an antibody that neutralizes this portion of Coa would provide protection against staphylococcal infection by several S. aureus types, mice received intraperitoneal injections of 3B3.14 or IgG1 isotype control, and were subsequently infected with a lethal dose of S. aureus clinical isolate USA300 (Coa type III), N315 (Coa type II), CowanI (Coa type IV), or MW2 (Coa type VII), and were monitored over a ten-day observation period to assess their protective role (FIG. 7). 3B3.14 did not protect mice against challenge with the wildtype Newman (IgG1 vs. 3B3.14 p>0.05 FIG. 7A), N315 (IgG1 vs. 3B3.14 p.0.05 FIG. 7B), or MW2 (IgG1 vs. 3B3.14 p.0.05 FIG. 7D). 3B3.14 provided a modest delay in time to death following challenge with strain CowanI (IgG1 vs. 3B3.14 p<0.001FIG. 7C)

Discussion. Coagulase expression has been correlated with the virulence of S. aureus for nearly a century [212]. Recently, it was demonstrated that a humoral immune response generated against Coa and vWbp provides protection against challenge with S. aureus (Cheng et al 2010, McAdow et al 2011, [215]). Neutralization of Coa activity results in type-specific immune responses, while immune responses to $CT_{Coa}$ also confer protection, presumably by removal of the antigen from circulation [215]. Here, we identify monoclonal antibodies that neutralize Coa activity and exhibit some cross-protection toward coagulases of other serotypes. In this study, we generated monoclonal antibodies against Coa from strain Newman and mapped their binding to specific domains of the polypeptide.

Three Mabs (5D5.4, 8C2.9, and 7H4.25) bind $D1_{Coa}$ and delay blood coagulation by strain Newman. Mab 5D5.4, which results in the greatest delay in coagulation, also disrupts the formation of the Coa•prothrombin complex, thereby diminishing assembly of the enzyme that converts fibrinogen to fibrin. Mabs 5D5.4 and 7H4.25 provide protection against lethal disease by S. aureus strain vwb.

Because the N-terminal amino acids of Coa are required for activation of prothrombin, we wondered whether any of the monoclonal antibodies recognize this domain. To address this question, we asked whether the first 18 amino acids of $D1_{Coa}$, were required for Mabs to bind. 5D5.4 had greater than 1-log reduction in affinity to $D1_{\Delta1-18}$, and 7H4.25 failed to bind this construct. This finding supports the hypothesis that these two monoclonal antibodies disrupt coagulation by specifically interfering with the ability of the Coa N-terminus to insert into the prothrombin activation pocket.

If this hypothesis were true, Mabs 5D5.4 and 7H4.25 should recognize and neutralize recombinant Coa cloned from other strains of S. aureus. These antibodies do recognize recombinant Coa cloned from S. aureus strains that represent other common serotypes in the current epidemic, but they fail to delay clotting by strains of other Coa serotypes in our experiments. It therefore seems unlikely that these Mabs recognize specifically the amino terminus. Nevertheless, 5D5.4 provides protection against at least two other strains of S. aureus. This indicates that while the antibody does not specifically recognize the most conserved portion of Coa, its interaction with Coa does require the conserved residues.

Previously, we demonstrated that antibodies to the D1D2 domains of Coa generate type-specific immunity. The identification of a Mab that protects animals against several staphylococcal strains of distinct Coa serotypes provides evidence that it may be possible to generate protective immunity that neutralizes the Coa activity by an array of staphylococcal isolates.

Two monoclonal antibodies recognize $CT_{Coa}$. Neither has an effect on blood coagulation, consistent with previous observations [215]. One of these, 3B3.14 disrupted binding of fibrinogen to the C-terminal repeat region. A more refined mapping of the epitope recognized by Mab 3B3.14 could reveal how the Coa C-terminus binds fibrinogen, which has not been studied to date. Passive transfer of these Mabs did not protect mice against lethal challenge with staphylococci.

The monoclonal antibodies described here provide pharmacologic tools for the prevention of staphylococcal disease. They also can serve as tools for understanding the mechanisms of Coa during staphylococcal pathogenesis and immunity.

Example 2

Materials and Methods

Bacterial Strains and Growth of Cultures. S. aureus strains were cultured on tryptic soy agar or broth at 37° C. Generation of strain vwb was described previously (Cheng et al 2010). Escherichia coli strains DH5a and BL21 (DE3) were cultured on Luria Bertani agar or broth at 37° C. Ampicillin (100 µg/ml) was used for pET15b and pGEX6P-1 selection.

Protein Purification. E. coli BL21(DE3) harboring expression vectors containing coa and its subdomains from S. aureus strain Newman were grown at 37° C. and induced with 100 mM IPTG overnight at room temperature. Because of degradation during the purification of Coa, pGEX6P-1 expression vectors in E. coli DH5α were used to express coa from USA300, N315, MW2, MRSA252, 85/2082, and WIS as GST-tagged constructs. Three hours following induction, cells were centrifuged at 7,000×g, suspended in 1×column buffer (0.1 M Tris-HCl, pH 7.5, 0.5 M NaCl) and lysed in a French pressure cell at 14,000 lb/in². Lysates were subjected to ultracentrifugation at 40,000×g for 30 min. The supernatant of pET15b constructs was subjected to Ni-NTA chromatography, washed with column buffer containing 10 mM imidazole, and eluted with 500 mM imidazole. For GST-tagged proteins, culture supernatants were subjected to glutathione sepharose chromatography. To remove the GST tag, after washing with column buffer, PreScission protease cleavage buffer containing 1 mM DTT was flowed over the column, and the column was incubated with PreScission protease (GE Healthcare) overnight at the unit definition provided by the manufacturer. Liberated protein lacking the GST tag was then eluted with additional protease cleavage buffer. Eluates were desalted against phosphate buffered saline (PBS). For vaccine preparations, endotoxin was removed by the addition of 1:100 Triton-X114 was added and the solution was chilled for 10 min, incubated at 37° C. for 10 min, and centrifuged at 13,000×g. This was repeated twice. Supernatant was loaded onto a HiTrap desalting column to remove remnants of Triton-X114.

Production of Monoclonal Antibodies Against Coagulase. Three eight-week-old BALB/c female mice (Jackson Laboratory, Bar Harbor, Me.) were immunized intraperitoneally with 100 µg purified Coa, which was cloned from S. aureus strain Newman, in PBS emulsified 1:1 in Complete Freund's Adjuvant (DIFCO). On days 21 and 42, mice were boosted by intraperitoneal injection with 100 µg purified Coa emulsified 1:1 in Incomplete Freund's Adjuvant (DIFCO). On days 31 and 52, mice were bled and screened by ELISA on Nunc MaxiSorp 96-well flat bottom plates coated with Coa. Seventy-nine days after the initial immunization, mice that showed strong immunoreactivity to antigen were boosted with 25 µg Coa in PBS. Three days later splenocytes were harvested and fused, according to standard methods, with the mouse myeloma cell line SP2/mIL-6, an interleukin 6 secreting derivative of SP2/0 myeloma cell line. Hybridomas were screened by ELISA and antigen-specific clones were subcloned, by limiting dilution, to produce monoclonal antibody-secreting hybridomas arising from single cells. Antibodies were purified from the culture supernatant of cell lines and stored at a concentration of 1 mg ml$^{-1}$ in PBS.

Coa Affinity Mapping. For the determination of binding affinity of Coa specific Mabs, Nunc MaxiSorp 96-well plates were coated with the Coa variants at a concentration of 20 nM in 0.1M sodium bicarbonate. Plates were blocked with 3% BSA in PBS, followed by incubation with variable concentrations of Mabs in PBS-Tween. The affinity of Mabs to bind each Coa variant was measured as the ratio of the concentration of bound to free antibody using secondary antibody-HRP conjugates and chemiluminescence detection. Using this data, the association constant of antibody for antigen was calculated (Table 1). Moreover, in order to test the specificity of Mabs raised against Coa, ELISA plates (NUNC Maxisorp) were coated with affinity purified vWbp and IsdA Blocking Protein Interactions by ELISA. MaxSorb 96-well ELISA plates were coated with recombinant Coa variants (20 nM in IX coating buffer) overnight. After blocking, wells where then incubated with Mabs ranging in concentration from 20 nM to 1 µM. Wells were subsequently incubated with either 100 nM human fibrinogen or 20 nM human prothrombin. Sheep anti-human antibodies against the respective proteins were added at 1:1000 dilution followed by HRP-conjugated goat-anti-sheep antibody at 1:10,000. The wells were developed using OpEIA Kit (BD Lifesciences) and the absorbance at 450 nm was measured. Statistical analyses were performed using a two-tailed Student's t-test with GraphPad Prism.

Coagulation Assay. Overnight cultures of staphylococcal strains were diluted 1:100 into fresh TSB and grown at 37° C. until they reached an OD$_{600}$ 0.4. One mL of culture was centrifuged, and staphylococci were washed and suspended in 1 mL of sterile PBS to generate a suspension of 1×10$^8$ CFU/mL. Whole blood from naïve BALB/c mice was collected and sodium citrate was added to a final concentration 1% (w/v). To assess bacterial blood coagulating activity in the presence of antibodies, 10 µL of the stock bacterial culture was mixed with 10 µL of PBS containing 30 µM of antibodies in a sterile plastic test tube (BD Falcon) and incubated for fifteen minutes. To each tube, 80 µL of anti-coagulated mouse blood in a sterile plastic test tube (BD falcon). Test tubes were incubated at 37° C. and blood coagulation was verified by tipping the tubes to 45° angles at timed intervals. All experiments were repeated in at least two independent experiments.

Measurement of Coagulase Activity. 5×10$^{-8}$ M prothrombin (Innovative Research) was pre-incubated for 10 min with an equimolar amount of functional Coa at room temperature, followed by addition of S-2238 (a chromogenic substrate) to a final concentration of 1 mM in a total reaction buffer of 100 µl PBS. The change in absorbance was measured at 450 nm for 10 minutes in a spectrophotometer, plotted as a function of time, and fit to a linear curve. The slope of the curve (dA/dt) was interpreted to be the rate of S-2238 hydrolysis, and thus reflective of enzymatic function. The assay was repeated in presence of monoclonal antibodies added at 5×10$^{-9}$ M and data were normalized to the average activity without inhibition. All experiments were performed in triplicate.

Murine Sepsis with Passive Immunization. Affinity purified antibodies in PBS were injected at a concentration 5 mg·kg$^{-1}$ of experimental animal weight into the peritoneal cavity of BALB/c mice (6 week old, female, Charles River Laboratories) 6 hours prior to challenge with S. aureus. An overnight culture of S. aureus strain vwb was diluted 1:100 into fresh TSB and grown for 2 hours at 37° C. Staphylococci were sedimented, washed and suspended in PBS to the desired concentration. The following inocula were used: vwb, 2×10$^8$ CFU; N315, 1×10$^8$ CFU; MW2, 2×10$^8$ CFU. Inocula were confirmed by spreading sample aliquots on TSA and enumerating colonies formed on agar plates. Mice were anesthetized via intraperitoneal injection with 100 mg mL$^{-1}$ ketamine and 20 mg mL$^{-1}$ xylazine per kilogram of body weight. Mice were infected by retro-orbital injection with 100 µL of a staphylococcal suspension (vide supra). Mice were monitored for survival. Statistical analysis was performed using two-tailed Log Rank test using GraphPad Prism. All mouse experiments were performed in accordance with the institutional guidelines following experimental protocol review and approval by the Institutional Biosafety Committee (IBC) and the Institutional Animal Care and Use Committee (IACUC) at the University of Chicago.

Example 3

Coa mAb Heavy and Light Chain Amino Acid Sequences Alignment and Analysis

The light and heavy chain variable regions of the different monoclonal antibodies were sequenced. The CDRs of these regions in the antibodies is provided in Table 5 below. Following alignment of mAb sequences via IMGT vquest, CDRs were identified and amino acid sequences of heavy and light CDRs 1, 2, and 3 were aligned using Clustal Omega. Following sequence alignment and analysis, a handful of informative themes were present. Based on the full sequences (both heavy and light chains) available, no mAbs appeared to be identical in sequence, though families of mAbs with similar sequences did emerge. One of these included 4F1.7,2A3.1, 2H10.12, with the main sequence differences present in CDR3 of both heavy and light chain.7H4.25, 4H9.20, 4B10.44 shared exact CDR sequence matches within the light chain, while their light chains were different. An interesting group to emerge based on sequence similarity was 3B3.14 and 6C4.15 which bind the C terminal region of the protein, shared the ame CRDI in the light chain, but the heavy chain are different. Instaed 5D5.4 which bind the D domain, inhibit the binding of coa to prothrombin and is protective in "in vivo experiment" I very different in both light and heavy chain from all the others.

TABLE 5

Amino acid sequences of CDR regions of
variable light chain of monoclonal antibodies Amino acid sequencing data of coagulase
specific monoclonal antibodies

| [a]Antibody | Variable chain | CDR1 | SEQ ID NO. | CDR2 | SEQ ID NO. | CDR3 | SEQ ID NO. |
|---|---|---|---|---|---|---|---|
| 4H9.20 | Light | QSVDYNGISY | 9 | AAS | 10 | QQSIEDPRT | 11 |
| 5D5.4 | Light | SSVSSSY | 15 | STS | 16 | QQYHRSPPT | 17 |
| 4B10.44 | Light | QSVDYNGISY | 9 | AAS | 21 | HQSIEDPRT | 22 |
| 3B3.14 | Light | QSIVHSNGNTY | 24 | KVS | 25 | FQGSHVPLT | 26 |
| 7H4.25 | Light | QSVDYNGISY | 9 | AAS | 21 | HQSIEDPRT | 30 |
| 2A3.1 | Light | QSLLNSRARKNY | 33 | WAS | 34 | KQSYNLWT | 35 |
| 2H10.12 | Light | QSLLNSRARKNY | 40 | WAS | 34 | KQSYYLWT | 36 |
| 6D1.22 | Light | QSLLNSRARKNY | 40 | WAS | 34 | KQSYNLWT | 35 |
| 6C4.15 | Light | QSLLNSRTRKIY | 44 | WAS | 34 | KQSYYLYT | 45 |
| 6C10.19 | Light | QNIVHSNGNTY | 56 | KVS | 25 | LQGSNCSNH | 57 |
| 8C2.9 | Light | QSLLNSRARKNY | 40 | WAS | 34 | KQSYNLWT | 35 |
| 4F1.7 | Light | QSLFNSRARKNY | 49 | WAS | 34 | KQSYNLWT | 35 |
| 4H9.20 | Heavy | GFNIKDIY | 12 | IDPANGNT | 13 | SRSGAY | 14 |
| 5D5.4 | Heavy | GASITTSY | 18 | ISYSGNT | 19 | AATYYDFNYDGYLDV | 20 |
| 4B10.44 | Heavy | GFNIKDIY | 12 | IDPANGNT | 13 | SRSGAF | 23 |
| 3B3.14 | Heavy | GYTFTSFD | 27 | IFPGDGSS | 28 | VKNHGGWSFDV | 29 |
| 7H4.25 | Heavy | GFNIKDIY | 12 | IDPADGHS | 31 | SRSGAI | 32 |
| 2A3.1 | Heavy | YTLTDYS | 37 | INTETGEP | 38 | ARTARDY | 39 |
| 2H10.12 | Heavy | GYTLTDYS | 41 | INTETGEP | 38 | GRTARADY | 42 |
| 6D1.22 | Heavy | GYTLTDYS | 41 | INTETGDP | 43 | ARTARADY | 38 |
| 6C4.15 | Heavy | GFSFSNYW | 46 | IRLKSDNYGT | 47 | SAYGDYEY | 48 |
| 6C10.19 | Heavy | GYEFTDFE | 50 | FDPETGRS | 51 | SRFHYYGRTAY | 52 |
| 8C2.9 | Heavy | GFTFSNYY | 53 | IKSNGVST | 54 | VRHDGYYFAY | 55 |
| 4F1.7 | Heavy | GFSIKDTT | 58 | IDPTDGHN | 59 | KQSYNLWT | 60 |

[a]Amplified PCR products from cDNA which was synthesized from total RNA extracted from hybridoma cells were sequenced and analyzed using IMGT Vquest.

REFERENCES

The following references, to the extent that they provide exemplary procedural or other details supplementary to those set forth herein, are specifically incorporated herein by reference.

1. Ryan K J, Ray C G, Sherris J C, editors (2004) Sherris medical microbiology: an introduction to infectious diseases. 4th ed. New York: McGraw-Hill. xiii, 979 p. p.
2. Lowy F D (1998) Staphylococcus aureus infections. The New England journal of medicine 339: 520-532.
3. Boucher H W, Corey G R (2008) Epidemiology of methicillin-resistant Staphylococcus aureus. Clinical infectious diseases: an official publication of the Infectious Diseases Society of America 46 Suppl 5: S344-349.
4. Chu V H, Crosslin D R, Friedman J Y, Reed S D, Cabell C H, et al. (2005) Staphylococcus aureus bacteremia in patients with prosthetic devices: costs and outcomes. The American journal of medicine 118: 1416.
5. Kallen A J, Brunkard J, Moore Z, Budge P, Arnold K E, et al. (2009) Staphylococcus aureus community-acquired pneumonia during the 2006 to 2007 influenza season. Annals of emergency medicine 53: 358-365.
6. Kang J, Sickbert-Bennett E E, Brown V M, Weber D J, Rutala W A (2011) Relative frequency of health care-associated pathogens by infection site at a university hospital from 1980 to 2008. American journal of infection control.
7. Gravenkemper C F, Brodie J L, Kirby W M (1965) Resistance of Coagulase-Positive Staphylococci to Methicillin and Oxacillin. Journal of bacteriology 89: 1005-1010.
8. Saravolatz L D, Pohlod D J, Arking L M (1982) Community-acquired methicillin-resistant Staphylococcus

*aureus* infections: a new source for nosocomial outbreaks. Annals of internal medicine 97: 325-329.
9. Herold B C, Immergluck L C, Maranan M C, Lauderdale D S, Gaskin R E, et al. (1998) Community-acquired methicillin-resistant *Staphylococcus aureus* in children with no identified predisposing risk. JAMA: the journal of the American Medical Association 279: 593-598.
10. Noble W C, Virani Z, Cree R G (1992) Co-transfer of vancomycin and other resistance genes from *Enterococcus faecalis* NCTC 12201 to *Staphylococcus aureus*. FEMS microbiology letters 72: 195-198.
11. Weigel L M, Clewell D B, Gill S R, Clark N C, McDougal L K, et al. (2003) Genetic analysis of a high-level vancomycin-resistant isolate of *Staphylococcus aureus*. Science 302: 1569-1571.
12. McAlecse F M, Foster T J (2003) Analysis of mutations in the *Staphylococcus aureus* clfB promoter leading to increased expression. Microbiology 149: 99-109.
13. Sievert D M, Rudrik J T, Patel J B, McDonald L C, Wilkins M J, et al. (2008) Vancomycin-resistant *Staphylococcus aureus* in the United States, 2002-2006. Clinical infectious diseases: an official publication of the Infectious Diseases Society of America 46: 668-674.
14. Ferry T, Perpoint T, Vandenesch F, Etienne J (2005) Virulence determinants in *Staphylococcus aureus* and their involvement in clinical syndromes. Current infectious disease reports 7: 420-428.
15. Hartleib J, Kohler N, Dickinson R B, Chhatwal G S, Sixma J J, et al. (2000) Protein A is the von Willebrand factor binding protein on *Staphylococcus aureus*. Blood 96: 2149-2156.
16. Clarke S R, Foster S J (2006) Surface adhesins of *Staphylococcus aureus*. Advances in microbial physiology 51: 187-224.
17. Schneewind O, Fowler A, Faull K F (1995) Structure of the cell wall anchor of surface proteins in *Staphylococcus aureus*. Science 268: 103-106.
18. Mazmanian S K, Liu G, Ton-That H, Schneewind O (1999) *Staphylococcus aureus* sortase, an enzyme that anchors surface proteins to the cell wall. Science 285: 760-763.
19. Mazmanian S K, Liu G, Jensen E R, Lenoy E, Schneewind O (2000) *Staphylococcus aureus* sortase mutants defective in the display of surface proteins and in the pathogenesis of animal infections. Proceedings of the National Academy of Sciences of the United States of America 97: 5510-5515.
20. McAdow M, Kim H K, Dedent A C, Hendrickx A P, Schneewind O, et al. (2011) Preventing *Staphylococcus aureus* sepsis through the inhibition of its agglutination in blood. PLoS pathogens 7: e1002307.
21. Cheng A G, Kim H K, Burts M L, Krausz T, Schneewind O, et al. (2009) Genetic requirements for *Staphylococcus aureus* abscess formation and persistence in host tissues. The FASEB journal: official publication of the Federation of American Societies for Experimental Biology 23: 3393-3404.
22. Mazmanian S K, Skaar E P, Gaspar A H, Humayun M, Gornicki P, et al. (2003) Passage of heme-iron across the envelope of *Staphylococcus aureus*. Science 299: 906-909.
23. Weidenmaier C, Kokai-Kun J F, Kristian S A, Chanturiya T, Kalbacher H, et al. (2004) Role of teichoic acids in *Staphylococcus aureus* nasal colonization, a major risk factor in nosocomial infections. Nature medicine 10: 243-245.
24. Lee J C, Betley M J, Hopkins C A, Perez N E, Pier G B (1987) Virulence studies, in mice, of transposon-induced mutants of *Staphylococcus aureus* differing in capsule size. The Journal of infectious diseases 156: 741-750.
25. Lin W S, Cunneen T, Lee C Y (1994) Sequence analysis and molecular characterization of genes required for the biosynthesis of type 1 capsular polysaccharide in *Staphylococcus aureus*. Journal of bacteriology 176: 7005-7016.
26. Baddour L M, Lowrance C, Albus A, Lowrance J H, Anderson S K, et al. (1992) *Staphylococcus aureus* microcapsule expression attenuates bacterial virulence in a rat model of experimental endocarditis. The Journal of infectious diseases 165: 749-753.
27. Tuchscherr L P, Buzzola F R, Alvarez L P, Caccuri R L, Lee J C, et al. (2005) Capsule-negative *Staphylococcus aureus* induces chronic experimental mastitis in mice. Infection and immunity 73: 7932-7937.
28. Na'was T, Hawwari A, Hendrix E, Hebden J, Edelman R, et al. (1998) Phenotypic and genotypic characterization of nosocomial *Staphylococcus aureus* isolates from trauma patients. Journal of clinical microbiology 36: 414-420.
29. Paul-Satyaseela M, van Belkum A, Shivannavar C T, Gaddad S M (2004) Carriage of capsulated strains of *Staphylococcus aureus*: a population-based study performed in Gulbarga, South India. Epidemiology and infection 132: 831-838.
30. Melles D C, Taylor K L, Fattom A I, van Belkum A (2008) Serotyping of Dutch *Staphylococcus aureus* strains from carriage and infection. FEMS immunology and medical microbiology 52: 287-292.
31. Lattar S M, Tuchscherr L P, Caccuri R L, Centron D, Becker K, et al. (2009) Capsule expression and genotypic differences among *Staphylococcus aureus* isolates from patients with chronic or acute osteomyelitis. Infection and immunity 77: 1968-1975.
32. Sutter D E, Summers A M, Keys C E, Taylor K L, Frasch C E, et al. (2011) Capsular serotype of *Staphylococcus aureus* in the era of community-acquired MRSA. FEMS immunology and medical microbiology 63: 16-24.
33. Gonzalez M R, Bischofberger M, Pernot L, van der Goot F G, Freche B (2008) Bacterial pore-forming toxins: the (w)hole story?Cellular and molecular life sciences: CMLS 65: 493-507.
34. Wilke G A, Bubeck Wardenburg J (2010) Role of a disintegrin and metalloprotease 10 in *Staphylococcus aureus* alpha-hemolysin-mediated cellular injury. Proceedings of the National Academy of Sciences of the United States of America 107: 13473-13478.
35. Inoshima I, Inoshima N, Wilke G A, Powers M E, Frank K M, et al. (2011) A *Staphylococcus aureus* pore-forming toxin subverts the activity of ADAM 10 to cause lethal infection in mice. Nature medicine.
36. Powers M E, Kim H K, Wang Y, Bubeck Wardenburg J (2012) ADAM 10 Mediates Vascular Injury Induced by *Staphylococcus aureus* alpha-Hemolysin. The Journal of infectious diseases.
37. Kantyka T, Shaw L N, Potempa J (2011) Papain-like proteases of *Staphylococcus aureus*. Advances in experimental medicine and biology 712: 1-14.
38. de Haas C J, Veldkamp K E, Peschel A, Weerkamp F, Van Wamel W J, et al. (2004) Chemotaxis inhibitory protein of *Staphylococcus aureus*, a bacterial antiinflammatory agent. The Journal of experimental medicine 199: 687-695.
39. Rooijakkers S H, Ruyken M, Roos A, Daha M R, Presanis J S, et al. (2005) Immune evasion by a staphylococcal complement inhibitor that acts on C3 convertases. Nature immunology 6: 920-927.
40. Thammavongsa V, Kern J W, Missiakas D M, Schneewind O (2009) *Staphylococcus aureus* synthesizes adenosine to escape host immune responses. The Journal of experimental medicine 206: 2417-2427.
41. Palmqvist N, Patti J M, Tarkowski A, Josefsson E (2004) Expression of staphylococcal clumping factor A impedes macrophage phagocytosis. Microbes and infection/Institut Pasteur 6: 188-195.
42. Peterson P K, Verhoef J, Sabath L D, Quie P G (1977) Effect of protein A on staphylococcal opsonization. Infection and immunity 15: 760-764.
43. Goodyear C S, Silverman G J (2004) Staphylococcal toxin induced preferential and prolonged in vivo deletion of innate-like B lymphocytes. Proceedings of the National Academy of Sciences of the United States of America 101: 11392-11397.
44. Kim H K, Cheng A G, Kim H Y, Missiakas D M, Schneewind O (2010) Nontoxigenic protein A vaccine for methicillin-resistant *Staphylococcus aureus* infections in mice. The Journal of experimental medicine 207: 1863-1870.
45. Wang Z, Wilhelmsson C, Hyrsl P, LoofTG, Dobes P, et al. (2010) Pathogen entrapment by transglutaminase—a conserved early innate immune mechanism. PLoS pathogens 6: e1000763.
46. Loof T G, Morgelin M, Johansson L, Oehmcke S, Olin A I, et al. (2011) Coagulation, an ancestral serine protease cascade, exerts a novel function in early immune defense. Blood.
47. Krarup A, Wallis R, Presanis J S, Gal P, Sim R B (2007) Simultaneous activation of complement and coagulation by MBL-associated serine protease 2. PLoS one 2: e623.
48. Loeb L (1903) The Influence of certain Bacteria on the Coagulation of the Blood. The Journal of medical research 10: 407-419.
49. Cheng A G, McAdow M, Kim H K, Bae T, Missiakas D M, et al. (2010) Contribution of coagulases towards *Staphylococcus aureus* disease and protective immunity. PLoS pathogens 6.
50. Adams R L, Bird R J (2009) Review article: Coagulation cascade and therapeutics update: relevance to nephrology. Part 1: Overview of coagulation, thrombophilias and history of anticoagulants. Nephrology 14: 462-470.
51. Gailani D, Renne T (2007) Intrinsic pathway of coagulation and arterial thrombosis. Arteriosclerosis, thrombosis, and vascular biology 27: 2507-2513.
52. Procyk R, Blomback B (1990) Disulfide bond reduction in fibrinogen: calcium protection and effect on clottability. Biochemistry 29: 1501-1507.
53. Kollman J M, Pandi L, Sawaya M R, Riley M, Doolittle R F (2009) Crystal structure of human fibrinogen. Biochemistry 48: 3877-3886.
54. Blomback B, Hessel B, Hogg D, Therkildsen L (1978) A two-step fibrinogen-fibrin transition in blood coagulation. Nature 275: 501-505.
55. Yang Z, Mochalkin I, Doolittle R F (2000) A model of fibrin formation based on crystal structures of fibrinogen and fibrin fragments complexed with synthetic peptides. Proceedings of the National Academy of Sciences of the United States of America 97: 14156-14161.
56. Lorand L (2000) Sol Sherry Lecture in Thrombosis: research on clot stabilization provides clues for improving thrombolytic therapies. Arteriosclerosis, thrombosis, and vascular biology 20: 2-9.
57. Delvaeye M, Conway E M (2009) Coagulation and innate immune responses: can we view them separately?Blood 114: 2367-2374.
58. Walker J B, Nesheim M E (1999) The molecular weights, mass distribution, chain composition, and structure of soluble fibrin degradation products released from a fibrin clot perfused with plasmin. The Journal of biological chemistry 274: 5201-52 12.
59. Rijken D C, Lijnen H R (2009) New insights into the molecular mechanisms of the fibrinolytic system. Journal of thrombosis and haemostasis: JTH 7: 4-13.
60. Lord S T (2011) Molecular mechanisms affecting fibrin structure and stability. Arteriosclerosis, thrombosis, and vascular biology 31: 494-499.
61. Konings J, Govers-Riemslag J W, Philippou H, Mutch N J, Borissoff J I, et al. (2011) Factor XIIa regulates the structure of the fibrin clot independently of thrombin generation through direct interaction with fibrin. Blood.
62. Ariens R A, Philippou H, Nagaswami C, Weisel J W, Lane D A, et al. (2000) The factor XIII V34L polymorphism accelerates thrombin activation of factor XIII and affects cross-linked fibrin structure. Blood 96: 988-995.
63. Andersen M D, Kjalke M, Bang S, Lautrup-Larsen I, Becker P, et al. (2009) Coagulation factor XIII variants with altered thrombin activation rates. Biological chemistry 390: 1279-1283.
64. Wolberg A S (2010) Plasma and cellular contributions to fibrin network formation, structure and stability. Haemophilia: the official journal of the World Federation of Hemophilia 16 Suppl 3: 7-12.
65. Mutch N J, Engel R, Uitte de Willige S, Philippou H, Ariens R A (2010) Polyphosphate modifies the fibrin network and down-regulates fibrinolysis by attenuating binding of tPA and plasminogen to fibrin. Blood 115: 3980-3988.
66. Friedrich R, Panizzi P, Fuentes-Prior P, Richter K, Verhamme I, et al. (2003) Staphylocoagulase is a prototype for the mechanism of cofactor-induced zymogen activation. Nature 425: 535-539.
67. Kroh H K, Panizzi P, Bock P E (2009) Von Willebrand factor-binding protein is a hysteretic conformational activator of prothrombin. Proceedings of the National Academy of Sciences of the United States of America 106: 7786-7791.
68. Watanabe S, Ito T, Takeuchi F, Endo M, Okuno E, et al. (2005) Structural comparison of ten serotypes of staphylocoagulases in *Staphylococcus aureus*. Journal of bacteriology 187: 3698-3707.
69. Kawabata S, Morita T, Iwanaga S, Igarashi H (1985) Staphylocoagulase-binding region in human prothrombin. Journal of biochemistry 97: 325-331.
70. Cheung A I, Projan S J, Edelstein R E, Fischetti V A (1995) Cloning, expression, and nucleotide sequence of a *Staphylococcus aureus* gene (fbpA) encoding a fibrinogen-binding protein. Infection and immunity 63: 1914-1920.
71. Phonimdaeng P, O'Reilly M, O'Toole P W, Foster T J (1988) Molecular cloning and expression of the coagulase gene of *Staphylococcus aureus* 8325-4. Journal of general microbiology 134: 75-83.
72. Bjerketorp J, Jacobsson K, Frykberg L (2004) The von Willebrand factor-binding protein (vWbp) of *Staphylococcus aureus* is a coagulase. FEMS microbiology letters 234: 309-314.

73. Bjerketorp J, Nilsson M, Ljungh A. Flock J I, Jacobsson K, et al. (2002) A novel von Willebrand factor binding protein expressed by *Staphylococcus aureus*. Microbiology 148: 2037-2044.
74. Chapman G H, Berens C, Peters A, Curcio L (1934) Coagulase and Hemolysin Tests as Measures of the Pathogenicity of Staphylococci. Journal of bacteriology 28: 343-363.
75. Spink W W, Vivino J J (1942) The Coagulase Test for Staphylococci and Its Correlation with the Resistance of the Organisms to the Bactericidal Action of Human Blood. The Journal of clinical investigation 21: 353-356.
76. Ekstedt R D, Yotis W W (1960) Studies on staphylococci. II. Effect of coagulase on the virulence of coagulase negative strains. Journal of bacteriology 80: 496-500.
77. Phonimdaeng P, O'Reilly M, Nowlan P, Bramley A J, Foster T J (1990) The coagulase of *Staphylococcus aureus* 8325-4. Sequence analysis and virulence of site-specific coagulase-deficient mutants. Molecular microbiology 4: 393-404.
78. Baddour L M, Tayidi M M, Walker E, McDevitt D, Foster T J (1994) Virulence of coagulase-deficient mutants of *Staphylococcus aureus* in experimental endocarditis. Journal of medical microbiology 41: 259-263.
79. Moreillon P, Entenza J M, Francioli P, McDevitt D, Foster T J, et al. (1995) Role of *Staphylococcus aureus* coagulase and clumping factor in pathogenesis of experimental endocarditis. Infection and immunity 63: 4738-4743.
80. Stutzmann Meier P, Entenza J M, Vaudaux P, Francioli P, Glauser M P, et al. (2001) Study of *Staphylococcus aureus* pathogenic genes by transfer and expression in the less virulent organism *Streptococcus gordonii*. Infection and immunity 69: 657-664.
81. Sawai T, Tomono K, Yanagihara K, Yamamoto Y, Kaku M. et al. (1997) Role of coagulase in a murine model of hematogenous pulmonary infection induced by intravenous injection of *Staphylococcus aureus* enmeshed in agar beads. Infection and immunity 65: 466-471.
82. Haraldsson I, Jonsson P (1984) Histopathology and pathogenesis of mouse mastitis induced with *Staphylococcus aureus* mutants. Journal of comparative pathology 94: 183-196.
83. Jonsson P, Lindberg M, Haraldsson I, Wadstrom T (1985) Virulence of *Staphylococcus aureus* in a mouse mastitis model: studies of alpha hemolysin, coagulase, and protein A as possible virulence determinants with protoplast fusion and gene cloning. Infection and immunity 49: 765-769.
84. Seki K, Ogasawara M, Sakurada J, Murai M, Masuda S (1989) Altered virulence of a pleiotropic *Staphylococcus aurcus* mutant with a low producibility of coagulase and other factors in mice. Microbiology and immunology 33: 981-990.
85. Johnstone J M, Smith D D (1956) Coagulase activity in vivo. Nature 178: 982-983.
86. Lam G T, Sweeney F J, Jr., Witmer C M, Wise R I (1963) Abscess-Forming Factor(S) Produced by *Staphylococcus Aureus*. I. Collodion Bag Implantation Technique. Journal of bacteriology 86: 611-615.
87. Lam G T, Sweeney F J, Jr., Witmer C M, Wise R I (1963) Abscess-Forming Factor(S) Produced by *Staphylococcus Aureus*. Ii. Abscess Formation and Immunity by a *Staphylococcus* and Its Mutants. Journal of bacteriology 86: 87-91.
88. Cawdery M, Foster W D, Hawgood B C, Taylor C (1969) The role of coagulase in the defence of *Staphylococcus aureus* against phagocytosis. British journal of experimental pathology 50: 408-412.
89. Kapral F A (1966) Clumping of *Staphylococcus aureus* in the peritoneal cavity of mice. Journal of bacteriology 92: 1188-1195.
90. Yeaman M R, Norman D C, Bayer A S (1992) Platelet microbicidal protein enhances antibiotic-induced killing of and postantibiotic effect in *Staphylococcus aureus*. Antimicrobial agents and chemotherapy 36: 1665-1670.
91. Fitzgerald J R, Foster T J, Cox D (2006) The interaction of bacterial pathogens with platelets. Nature reviews Microbiology 4: 445-457.
92. Ni Eidhin D, Perkins S, Francois P, Vaudaux P, Hook M, et al. (1998) Clumping factor B (ClfB), a new surface-located fibrinogen-binding adhesin of *Staphylococcus aureus*. Molecular microbiology 30: 245-257.
93. O'Brien L, Kerrigan S W, Kaw G, Hogan M, Penades J, et al. (2002) Multiple mechanisms for the activation of human platelet aggregation by *Staphylococcus aureus*: roles for the clumping factors ClfA and ClfB, the scrine-aspartate repeat protein SdrE and protein A. Molecular microbiology 44: 1033-1044.
94. Niemann S, Spehr N, Van Aken H, Morgenstern E, Peters G, et al. (2004) Soluble fibrin is the main mediator of *Staphylococcus aureus* adhesion to platelets. Circulation 110: 193-200.
95. Much H (1908) IUber eine Vorstufe des Fibrinfermentes in Kulturen von Staphylokokkus *aureus*. Biochem Z 14: 143-155.
96. Birch-Hirschfeld L (1934) 1ber die Agglutination von Staphylokokken durch Bestandteile des Siugetierblutplasmas. Klinische Woschenschrift 13: 331.
97. Cadness-Graves B. WR, Harper C. J., Miles A. A. (1943) Slide test for coagulase-positive staphylococci. Lancet 2: 736-738.
98. Berger F (1943) Clumping of pathogenic staphylococci in plasma. Journal of Pathology and Bacteriology 55.
99. Duthie E S (1954) Evidence for two forms of staphylococcal coagulase. Journal of general microbiology 10: 427-436.
100. McDevitt D, Francois P, Vaudaux P, Foster T J (1994) Molecular characterization of the clumping factor (fibrinogen receptor) of *Staphylococcus aureus*. Molecular microbiology 11: 237-248.
101. Que Y A, Haefliger J A, Francioli P, Moreillon P (2000) Expression of *Staphylococcus aureus* clumping factor A in *Lactococcus lactis* subsp. *cremoris* using a new shuttle vector. Infection and immunity 68: 3516-3522.
102. Umeda A, Ikebuchi T, Amako K (1980) Localization of bacteriophage receptor, clumping factor, and protein A on the cell surface of *Staphylococcus aureus*. Journal of bacteriology 141: 838-844.
103. Jensen K (2007) A normally occurring *Staphylococcus* antibody in human serum. APMIS: acta pathologica, microbiologica, et immunologica Scandinavica 115: 533-539; discussion 540-531.
104. Deisenhofer J, Jones T A, Huber R, Sjodahl J, Sjoquist J (1978) Crystallization, crystal structure analysis and atomic model of the complex formed by a human Fc fragment and fragment B of protein A from *Staphylococcus aureus*. Hoppe-Seyler's Zeitschrift fur physiologische Chemie 359: 975-985.
105. Graille M, Stura E A, Corper A L, Sutton B J, Taussig M J, et al. (2000) Crystal structure of a *Staphylococcus aureus* protein A domain complexed with the Fab fragment of a human IgM antibody: structural basis for recognition of B-cell receptors and superantigen activity.

Proceedings of the National Academy of Sciences of the United States of America 97: 5399-5404.
106. O'Seaghdha M, van Schooten C J, Kerrigan S W, Emsley J, Silverman G J, et al. (2006) *Staphylococcus aureus* protein A binding to von Willebrand factor A1 domain is mediated by conserved IgG binding regions. The FEBS journal 273: 4831-4841.
107. Projan S J, Nesin M, Dunman P M (2006) Staphylococcal vaccines and immunotherapy: to dream the impossible dream?Current opinion in pharmacology 6: 473-479.
108. Shinefield H, Black S, Fattom A, Horwith G, Rasgon S, et al. (2002) Use of a *Staphylococcus aureus* conjugate vaccine in patients receiving hemodialysis. The New England journal of medicine 346: 491-496.
109. Fattom A, Fuller S, Propst M, Winston S, Muenz L, et al. (2004) Safety and immunogenicity of a booster dose of *Staphylococcus aureus* types 5 and 8 capsular polysaccharide conjugate vaccine (StaphVAX) in hemodialysis patients. Vaccine 23: 656-663.
110. Kuklin N A, Clark D J, Secore S, Cook J, Cope L D, et al. (2006) A novel *Staphylococcus aureus* vaccine: iron surface determinant B induces rapid antibody responses in rhesus macaques and specific increased survival in a murine *S. aureus* sepsis model. Infection and immunity 74: 2215-2223.
111. Harro C, Betts R, Orenstein W, Kwak E J, Greenberg H E, et al. (2010) Safety and immunogenicity of a novel *Staphylococcus aureus* vaccine: results from the first study of the vaccine dose range in humans. Clinical and vaccine immunology: CVI 17: 1868-1874.
112. Kernodle D S (2011) Expectations regarding vaccines and immune therapies directed against *Staphylococcus aureus* alpha-hemolysin. The Journal of infectious diseases 203: 1692-1693; author reply 1693-1694.
113. DeDent A, Kim H K, Missiakas D, Schneewind O (2012) Exploring *Staphylococcus aureus* pathways to disease for vaccine development. Seminars in immunopathology 34: 317-333.
114. Balaban N, Goldkorn T, Nhan R T, Dang L B, Scott S, et al. (1998) Autoinducer of virulence as a target for vaccine and therapy against *Staphylococcus aureus*. Science 280: 438-440.
115. Arrecubieta C, Matsunaga I, Asai T, Naka Y, Deng M C, et al. (2008) Vaccination with clumping factor A and fibronectin binding protein A to prevent *Staphylococcus aureus* infection of an aortic patch in mice. The Journal of infectious diseases 198: 571-575.
116. Bubeck Wardenburg J, Schneewind 0 (2008) Vaccine protection against *Staphylococcus aureus* pneumonia. The Journal of experimental medicine 205: 287-294.
117. Gong R, Hu C, Xu H, Guo A, Chen H, et al. (2010) Evaluation of clumping factor A binding region A in a subunit vaccine against *Staphylococcus aureus*-induced mastitis in mice. Clinical and vaccine immunology: CVI 17: 1746-1752.
118. Josefsson E, Hartford O, O'Brien L, Patti J M, Foster T (2001) Protection against experimental *Staphylococcus aureus* arthritis by vaccination with clumping factor A, a novel virulence determinant. The Journal of infectious diseases 184: 1572-1580.
119. Kim H K, DeDent A, Cheng A G, McAdow M, Bagnoli F, et al. (2010) IsdA and IsdB antibodies protect mice against *Staphylococcus aureus* abscess formation and lethal challenge. Vaccine 28: 6382-6392.
120. Nilsson I M, Patti J M, Bremell T, Hook M, Tarkowski A (1998) Vaccination with a recombinant fragment of collagen adhesin provides protection against *Staphylococcus aureus*-mediated septic death. The Journal of clinical investigation 101: 2640-2649.
121. Kennedy A D, Bubeck Wardenburg J, Gardner D J, Long D, Whitney A R, et al. (2010) Targeting of alpha-hemolysin by active or passive immunization decreases severity of USA300 skin infection in a mouse model. The Journal of infectious diseases 202: 1050-1058.
122. Stranger-Jones Y K, Bae T, Schneewind O (2006) Vaccine assembly from surface proteins of *Staphylococcus aureus*. Proceedings of the National Academy of Sciences of the United States of America 103: 16942-16947.
123. Kim H K, Kim H Y, Schneewind O, Missiakas D (2011) Identifying protective antigens of *Staphylococcus aureus*, a pathogen that suppresses host immune responses. FASEB journal: official publication of the Federation of American Societies for Experimental Biology 25: 3605-3612.
124. Watanabe S, Ito T, Sasaki T, Li S, Uchiyama I, et al. (2009) Genetic diversity of staphylocoagulase genes (coa): insight into the evolution of variable chromosomal virulence factors in *Staphylococcus aureus*. PloS one 4: e5714.
125. McCarthy A J, Lindsay J A (2010) Genetic variation in *Staphylococcus aureus* surface and immune evasion genes is lineage associated: implications for vaccine design and host-pathogen interactions. BMC microbiology 10: 173.
126. Klevens R M, Edwards J R, Gaynes R P, System NNIS (2008) The impact of antimicrobial-resistant, health care-associated infections on mortality in the United States. Clin Infect Dis 47: 927-930.
127. Rogers D E, Melly M A (1965) Speculations on the immunology of staphylococcal infections. Annals of the New York Academy of Sciences 128: 274-284.
128. Goodyear C S, Silverman G J (2003) Death by a B cell superantigen: In vivo VH-targeted apoptotic supraclonal B cell deletion by a Staphylococcal Toxin. The Journal of experimental medicine 197: 1125-1139.
129. Field H I, Smith, H. W. (1945) Coagulase test for staphylococci. J Comp Pathol 55: 63.
130. Smith W, Hale J H, Smith M M (1947) The role of coagulase in staphylococcal infections. British journal of experimental pathology 28: 57-67.
131. Kinoshita M. Kobayashi N, Nagashima S, Ishino M, Otokozawa S, et al. (2008) Diversity of staphylocoagulase and identification of novel variants of staphylocoagulase gene in *Staphylococcus aureus*. Microbiology and immunology 52: 334-348.
132. Duthie E S, Lorenz L L (1952) Staphylococcal coagulase: mode of action and antigenicity. J Gen Microbiol 6: 95-107.
133. Panizzi P, Friedrich R, Fuentes-Prior P, Richter K, Bock P E, et al. (2006) Fibrinogen substrate recognition by staphylocoagulase.(pro)thrombin complexes. The Journal of biological chemistry 281: 1179-1187.
134. Tager M, Drummond M C (1965) Staphylocoagulase. Annals of the New York Academy of Sciences 128: 92-111.
135. Baba T, Bae T, Schneewind O, Takeuchi F, Hiramatsu K (2007) Genome sequence of Staphylocccus *aureus* strain Newman and comparative analysis of staphylococcal genomes. J Bacteriol 190: 300-310.
136. Albus A, Arbeit R D, Lee J C (1991) Virulence of *Staphylococcus aureus* mutants altered in type 5 capsule production. Infection and immunity 59: 1008-1014.

137. Rothfork J M, Dessus-Babus S, Van Wamel W J, Cheung A L, Gresham H D (2003) Fibrinogen depletion attenuates Staphyloccocus *aureus* infection by preventing density-dependent virulence gene up-regulation. Journal of immunology 171: 5389-5395.

138. Silberman S, Bernik M B, Potter E V, Kwaan H C (1973) Effects of Ancrod (Arvin) in mice: studies of plasma fibrinogen and fibrinolytic activity. British journal of haematology 24: 101-113.

139. Bae T, Schneewind O (2006) Allelic replacement in *Staphylococcus aureus* with inducible counter-selection. Plasmid 55: 58-63.

140. Schneewind O, Mihaylova-Petkov D, Model P (1993) Cell wall sorting signals in surface proteins of gram-positive bacteria. The EMBO journal 12: 4803-4811.

141. Schneewind O, Model P, Fischetti V A (1992) Sorting of protein A to the staphylococcal cell wall. Cell 70: 267-281.

142. Harvey R P, Degryse E, Stefani L, Schamber F, Cazenave J P, et al. (1986) Cloning and expression of a cDNA coding for the anticoagulant hirudin from the bloodsucking leech, Hirudo medicinalis. Proceedings of the National Academy of Sciences of the United States of America 83: 1084-1088.

143. Markwardt F (1955) Untersuchungen √°ber Hirudin: naturwiss. F.

144. Klevens R M, Morrison M A, Nadle J, Petit S, Gershman K, et al. (2007) Invasive methicillin-resistant *Staphylococcus aureus* infections in the United States. JAMA: the journal of the American Medical Association 298: 1763-1771.

145. DeBord K L, Anderson D M, Marketon M M, Overheim K A, DePaolo R W, et al. (2006) Immunogenicity and protective immunity against bubonic and pneumonic plague by immunization of mice with the recombinant V10 antigen, a variant of LcrV. Infect Immun 74: 4910-4914.

146. Panizzi P, Friedrich R, Fuentes-Prior P, Kroh H K, Briggs J, et al. (2006) Novel fluorescent prothrombin analogs as probes of staphylocoagulase-prothrombin interactions. The Journal of biological chemistry 281: 1169-1178.

147. Kennedy A D, Otto M, Braughton K R, Whitney A R, Chen L, et al. (2008) Epidemic community-associated methicillin-resistant *Staphylococcus aureus*: recent clonal expansion and diversification. Proceedings of the National Academy of Sciences of the United States of America 105: 1327-1332.

148. Mainiero M, Goerke C, Geiger T, Gonser C, Herbert S, et al. (2010) Differential target gene activation by the *Staphylococcus aureus* two-component system saeRS. Journal of bacteriology 192: 613-623.

149. Geoghegan J A, Ganesh V K, Smeds E, Liang X, Hook M, et al. (2010) Molecular characterization of the interaction of staphylococcal microbial surface components recognizing adhesive matrix molecules (MSCRAMM) ClfA and Fbl with fibrinogen. The Journal of biological chemistry 285: 6208-6216.

150. Josefsson E, Higgins J, Foster T J, Tarkowski A (2008) Fibrinogen binding sites P336 and Y338 of clumping factor A are crucial for *Staphylococcus aureus* virulence. PloS one 3: e2206.

151. Palma M, Wade D, Flock M, Flock J I (1998) Multiple binding sites in the interaction between an extracellular fibrinogen-binding protein from *Staphylococcus aureus* and fibrinogen. The Journal of biological chemistry 273: 13177-13181.

152. Heilmann C, Herrmann M, Kehrel B E, Peters G (2002) Platelet-binding domains in 2 fibrinogen-binding proteins of *Staphylococcus aureus* identified by phage display. The Journal of infectious diseases 186: 32-39.

153. Hussain M, Becker K, von Eiff C, Schrenzel J, Peters G, et al. (2001) Identification and characterization of a novel 38.5-kilodalton cell surface protein of *Staphylococcus aureus* with extended-spectrum binding activity for extracellular matrix and plasma proteins. Journal of bacteriology 183: 6778-6786.

154. Streitfeld M M, Sallman B, Shoelson S M (1959) Staphylocoagulase inhibition by pooled human gamma-globulin. Nature 184(Suppl 21): 1665-1666.

155. Studier F W, Rosenberg A H, Dunn J J, Dubendorff J W (1990) Use of T7 RNA polymerase to direct expression of cloned genes. Methods in enzymology 185: 60-89.

156. Chambers H F, Deleo F R (2009) Waves of resistance: *Staphylococcus aureus* in the antibiotic era. Nature reviews Microbiology 7: 629-641.

157. Fowler V G, Jr., Miro J M, Hoen B, Cabell C H, Abrutyn E, et al. (2005) *Staphylococcus aureus* endocarditis: a consequence of medical progress. JAMA: the journal of the American Medical Association 293: 3012-3021.

158. DeLeo F R, Otto M, Kreiswirth B N, Chambers H F (2010) Community-associated meticillin-resistant *Staphylococcus aureus*. Lancet 375: 1557-1568.

159. Foster T J (2005) Immune evasion by staphylococci. Nature reviews Microbiology 3: 948-958.

160. Walsh E I, Miajlovic H, Gorkun O V, Foster T J (2008) Identification of the *Staphylococcus aureus* MSCRAMM clumping factor B (ClfB) binding site in the alphaC-domain of human fibrinogen. Microbiology 154: 550-558.

161. Cheng A G, DeDent A C, Schneewind O, Missiakas D (2011) A play in four acts: *Staphylococcus aureus* abscess formation. Trends in microbiology 19: 225-232.

162. Doolittle R F (2003) Structural basis of the fibrinogen-fibrin transformation: contributions from X-ray crystallography. Blood reviews 17: 33-41.

163. Kolle W, Otto, R. (1902) Die Differenzierung der Staphylokokken mittelst der Agglutination. Z Hygiene 41.

164. Hawiger J, Timmons S, Strong D D, Cottrell B A, Riley M, et al. (1982) Identification of a region of human fibrinogen interacting with staphylococcal clumping factor. Biochemistry 21: 1407-1413.

165. McDevitt D, Francois P, Vaudaux P, Foster T J (1995) Identification of the ligand-binding domain of the surface-located fibrinogen receptor (clumping factor) of *Staphylococcus aureus*. Molecular microbiology 16: 895-907.

166. McDevitt D, Nanavaty T, House-Pompeo K, Bell E, Turner N, et al. (1997) Characterization of the interaction between the *Staphylococcus aureus* clumping factor (ClfA) and fibrinogen. European journal of biochemistry/FEBS 247: 416-424.

167. Strong D D, Laudano A P, Hawiger J, Doolittle R F (1982) Isolation, characterization, and synthesis of peptides from human fibrinogen that block the staphylococcal clumping reaction and construction of a synthetic clumping particle. Biochemistry 21: 1414-1420.

168. Ganesh V K, Rivera J J, Smeds E, Ko Y P, Bowden M G, et al. (2008) A structural model of the *Staphylococcus aureus* ClfA-fibrinogen interaction opens new avenues for the design of anti-staphylococcal therapeutics. PLoS pathogens 4: e1000226.

169. Hair P S, Echague C G, Sholl A M, Watkins J A, Geoghegan J A, et al. (2010) Clumping factor A interaction with complement factor I increases C3b cleavage on the bacterial surface of *Staphylococcus aureus* and decreases complement-mediated phagocytosis. Infection and immunity 78: 1717-1727.
170. Hall A E, Domanski P J, Patel P R, Vernachio J H, Syribeys P J, et al. (2003) Characterization of a protective monoclonal antibody recognizing *Staphylococcus aureus* MSCRAMM protein clumping factor A. Infection and immunity 71: 6864-6870.
171. Weems J J, Jr., Steinberg J P, Filler S, Baddley J W, Corey G R, et al. (2006) Phase II, randomized, double-blind, multicenter study comparing the safety and pharmacokinetics of tefibazumab to placebo for treatment of *Staphylococcus aureus* bacteremia. Antimicrobial agents and chemotherapy 50: 2751-2755.
172. Bae T, Banger A K, Wallace A, Glass E M, Aslund F, et al. (2004) *Staphylococcus aureus* virulence genes identified by bursa aurealis mutagenesis and nematode killing. Proceedings of the National Academy of Sciences of the United States of America 101: 12312-12317.
173. Kaida S, Miyata T, Yoshizawa Y, Kawabata S, Morita T, et al. (1987) Nucleotide sequence of the staphylocoagulase gene: its unique COOH-terminal 8 tandem repeats. Journal of biochemistry 102: 1177-1186.
174. Palma M, Nozohoor S, Schennings T, Heimdahl A, Flock J I (1996) Lack of the extracellular 19-kilodalton fibrinogen-binding protein from *Staphylococcus aureus* decreases virulence in experimental wound infection. Infection and immunity 64: 5284-5289.
175. Hawiger J, Hammond D K, Timmons S (1975) Human fibrinogen possesses binding site for staphyococci on Aalpha and Bbeta polypeptide chains. Nature 258: 643-645.
176. Hijikata-Okunomiya A, Kataoka N (2003) Argatroban inhibits staphylothrombin. Journal of thrombosis and haemostasis: JTH 1: 2060-2061.
177. Vanassche T, Verhaegen J, Peetermans W E, Hoylaerts M F, Verhamme P (2010) Dabigatran inhibits *Staphylococcus aureus* coagulase activity. Journal of clinical microbiology 48: 4248-4250.
178. Hauel N H, Nar H, Priepke H, Ries U, Stassen J M, et al. (2002) Structure-based design of novel potent nonpeptide thrombin inhibitors. Journal of medicinal chemistry 45: 1757-1766.
179. Baba T, Takeuchi F, Kuroda M, Yuzawa H, Aoki K, et al. (2002) Genome and virulence determinants of high virulence community-acquired MRSA. Lancet 359: 1819-1827.
180. Kuroda M. Ohta T, Uchiyama I, Baba T, Yuzawa H, et al. (2001) Whole genome sequencing of meticillin-resistant *Staphylococcus aureus*. Lancet 357: 1225-1240.
181. Liu C, Bayer A, Cosgrove S E, Daum R S, Fridkin S K, et al. (2011) Clinical practice guidelines by the infectious diseases society of America for the treatment of methicillin-resistant *Staphylococcus aureus* infections in adults and children: executive summary. Clinical infectious diseases: an official publication of the Infectious Diseases Society of America 52: 285-292.
182. Walsh C T (1993) Vancomycin resistance: decoding the molecular logic. Science 261: 308-309.
183. Fowler V G, Jr., Boucher H W, Corey G R, Abrutyn E, Karchmer A W, et al. (2006) Daptomycin versus standard therapy for bacteremia and endocarditis caused by *Staphylococcus aureus*. The New England journal of medicine 355: 653-665.
184. Diep B A, Gill S R, Chang R F, Phan T H, Chen J H, et al. (2006) Complete genome sequence of USA300, an epidemic clone of community-acquired meticillin-resistant *Staphylococcus aureus*. Lancet 367: 731-739.
185. Donahue J P, Patel H, Anderson W F, Hawiger J (1994) Three-dimensional structure of the platelet integrin recognition segment of the fibrinogen gamma chain obtained by carrier protein-driven crystallization. Proceedings of the National Academy of Sciences of the United States of America 91: 12178-12182.
186. Ware S, Donahue J P, Hawiger J, Anderson W F (1999) Structure of the fibrinogen gamma-chain integrin binding and factor XIIIa cross-linking sites obtained through carrier protein driven crystallization. Protein science: a publication of the Protein Society 8: 2663-2671.
187. DeDent A, Bae T, Missiakas D M, Schneewind O (2008) Signal peptides direct surface proteins to two distinct envelope locations of *Staphylococcus aureus*. The EMBO journal 27: 2656-2668.
188. Panizzi P, Friedrich R, Fuentes-Prior P, Bode W, Bock P E (2004) The staphylocoagulase family of zymogen activator and adhesion proteins. Cellular and molecular life sciences: CMLS 61: 2793-2798.
189. Hale J H, Smith W (1945) The influence of coagulase on the phagocytosis of staphylococci. Br J Exp Pathol 26: 209-216.
190. Smith D D, Johnstone J M (1956) Coagulase activity in vivo. Nature 178: 982-983.
191. Kanemitsu K, Yamamoto H, Takemura, Kaku M, Shimada J (2001) Relatedness between the coagulase gene 3'-end region and coagulase serotypes among *Staphylococcus aureus* strains. Microbiol Immunol 45: 23-27.
192. Enright M C, Day N P J, Davies C E, Peacock S J, Spratt B G (2000) Multilocus sequence typing for characterization of methicillin-resistant and methicillin-susceptible clones of *Staphylococcus aureus*. J Clin Microbiol 38: 1008-1015.
193. Panizzi P, Nahrendorf M, Figueiredo J L, Panizzi J, Marinelli B, et al. (2011) In vivo detection of *Staphylococcus aureus* endocarditis by targeting pathogen-specific prothrombin activation. Nat Med 17: 1142-1146.
194. Patel G, Jenkins S G, Mediavilla J R, Kreiswirth B N, Radbill B, et al. (2011) Clinical and Molecular Epidemiology of Methicillin-Resistant *Staphylococcus aureus* among Patients in an Ambulatory Hemodialysis Center. Infection control and hospital epidemiology: the official journal of the Society of Hospital Epidemiologists of America 32: 881-888.
195. Tager M. Hales H B (1948) Properties of coagulase-reacting factor, and relation to blood clotting components. Journal of immunology 60: 1-9.
196. Lominski I, Roberts G B (1946) A substance in human serum inhibiting staphylocoagulase. The Journal of pathology and bacteriology 58: 187-199.
197. Lominski I (1949) Susceptibility and resistance to staphylococcal infection. Journal of general microbiology 3: ix.
198. Lominski I, Smith D D, Scott A C, Arbuthnott J P, Gray S, et al. (1962) Immunisation against experimental staphylococcal infection with coagulase-rich preparations. Lancet 1: 1315-1318.
199. Boake W C (1956) Antistaphylocoagulase in experimental staphylococcal infections. Journal of immunology 76: 89-96.
200. Rammelkamp C H, Hezebicks M M, Dingle J H (1950) Specific Coagulases of *Staphylococcus Aureus*. The Journal of experimental medicine 91: 295-307.

201. Duthie E S (1952) Variation in the antigenic composition of staphylococcal coagulase. Journal of general microbiology 7: 320-326.
202. Harrison K J (1964) The Protection of Rabbits against Infection with Staphylococci by Immunisation with Staphylocoagulase Toxin or Toxoid. The Journal of pathology and bacteriology 87: 145-150.
203. Rammelkamp Jr C H, Lebovitz J J (1956) Immunity, epidemiology and antimicrobial resistance. The role of coagulase in staphylococcal infections. Ann NY Acad Sci 65: 144-151.
204. Harrison K J (1963) Clinical trial of coagulase and alpha-hemolysin toxoids in chronic furunculosis. Br Mcd J 2: 149-152.
205. Koreen L, Ramaswamy S V, Graviss E A, Naidich S, Musser J M, et al. (2004) spa typing method for discriminating among *Staphylococcus aureus* isolates: implications for use of a single marker to detect genetic micro- and macrovariation. J Clin Microbiol 42: 792-799.
206. Lancefield R C (1928) The antigenic complex of *Streptoocccus hemolyticus*. I. Demonstration of a type-specific substance in extracts of *Streptococcus hemolyticus*. J Exp Med 47: 91-103.
207. Lancefield R (1962) Current knowledge of type-specific M antigens of group A streptococci. J Immunol 89: 307-313.
208. Mora M, Bensi G, Capo S, Falugi F, Zingaretti C, et al. (2005) Group A *Streptococcus* produce pilus-like structures containing protective antigens and Lancefield T antigens. Proc Natl Acad Sci USA 102: 15641-15646.
209. Nuccitelli A, Cozzi R, Goutlay L J, Donnarumma D, Necchi F, et al. (2011) A structure-based approach to rationally design a chimeric protein for an effective vaccine against Group B *Streptococcus* infections. Proc Natl Acad Sci USA 108: 10278-10283.
210. Schneewind O, Missiakas D (2011) Structural vaccinology to thwart antigenic variation in microbial pathogens. Proc Natl Acad Sci USA 108: 10029-10030.
211. Tenover F C, Tickler I A, Goering R V, Kreiswirth B N, Mediavilla J R, et al. (2012) Characterization of nasal and blood culture isolates of methicillin-resistant *Staphylococcus aureus* from patients in the United States. Antimicrob Agents Chemother 56: 1324-1330.
212. McAdow M, Missiakas D M, Schneewind O (2012) *Staphylococcus aureus* Secretes Coagulase and von Willebrand Factor Binding Protein to Modify the Coagulation Cascade and Establish Host Infections. Journal of innate immunity 4: 141-148.
213. Vanassche T, Verhaegen J, Peetermans W E, J VANR, Cheng A, et al. (2011) Inhibition of staphylothrombin by dabigatran reduces *Staphylococcus aureus* virulence. Journal of thrombosis and haemostasis: JTH 9: 2436-2446.
214. Palma M, Shannon O, Quezada H C, Berg A, Flock J I (2001) Extracellular fibrinogen-binding protein, Efb, from *Staphylococcus aureus* blocks platelet aggregation due to its binding to the alpha-chain. The Journal of biological chemistry 276: 31691-31697.
215. McAdow M D, A. C.; Emolo, C.; Cheng, A. G.; Kreiswirth, B.; Missiakas, D. M.; Schneewind, O. (2012) Coagulases as determinants of protective immune responses against *Staphylococcus aureus*. In preparation.
216. Kuehnert M J, Kruszon-Moran D, Hill H A, McQuillan G, McAllister S K, et al. (2006) Prevalence of *Staphylococcus aureus* nasal colonization in the United States, 2001-2002. The Journal of infectious diseases 193: 172-179.
217. Kluytmans J, van Belkum A, Verbrugh H (1997) Nasal carriage of *Staphylococcus aureus*: epidemiology, underlying mechanisms, and associated risks. Clinical microbiology reviews 10: 505-520.
218. Camargo I L, Gilmore M S (2008) *Staphylococcus aureus*-probing for host weakness?Journal of bacteriology 190: 2253-2256.
219. Plotkin S A, Orenstein W A, editors (2004) Vaccines. 4th ed. Philadelphia, Pa.: Saunders. xxi, 1662 p. p.
220. Levine M M, editor (2010) New generation vaccines. 4th ed. New York: Informa Healthcare USA. xxvii, 1011 p. p.
221. Zajdel M, Wagrzynowicz Z, Jeljaszewicz J (1975) Action of staphylothrombin on bovine fibrinogen. Thrombosis research 6: 501-510.
222. Soulier J P, Prou-Wartelle O (1967) Study of thrombin-coagulase. Thrombosis et diathesis haemorrhagica 17: 321-334.
223. Kawabata S, Morita T, Iwanaga S, Igarashi H (1985) Difference in enzymatic properties between alpha-thrombin-staphylocoagulase complex and free alpha-thrombin. Journal of biochemistry 97: 1073-1078.
224. Kawabata S, Morita T, Iwanaga S, Igarashi H (1985) Enzymatic properties of staphylothrombin, an active molecular complex formed between staphylocoagulase and human prothrombin. Journal of biochemistry 98: 1603-1614.
225. Hendrix H, Lindhout T, Mertens K, Engels W, Hemker H C (1983) Activation of human prothrombin by stoichiometric levels of staphylocoagulase. The Journal of biological chemistry 258: 3637-3644.
226. Kopec M, Wegrzynowicz Z, Budzynski A Z, Jeljaszewicz J, Latallo Z S, et al. (1967) Formation and properties of fibrin clots resulting from staphylocoagulase (SC) action. Thrombosis et diathesis haemorrhagica 18: 475-486.
227. Crawley J T, Zanardelli S, Chion C K, Lane D A (2007) The central role of thrombin in hemostasis. Journal of thrombosis and haemostasis: JTH 5 Suppl 1: 95-101.
228. Vanassche T, Kauskot A, Verhaegen J, Peetermans W E, van Ryn J, et al. (2012) Fibrin formation by staphylothrombin facilitates *Staphylococcus aureus*-induced platelet aggregation. Thrombosis and haemostasis 107.
229. Huber-Lang M, Sarma J V, Zetoune F S, Rittirsch D, Neff T A, et al. (2006) Generation of C5a in the absence of C3: a new complement activation pathway. Nature medicine 12: 682-687.
230. Deivanayagam C C, Wann E R, Chen W, Carson M, Rajashankar K R, et al. (2002) A novel variant of the immunoglobulin fold in surface adhesins of *Staphylococcus aureus*: crystal structure of the fibrinogen-binding MSCRAMM, clumping factor A. The EMBO journal 21: 6660-6672.
231. Lack C H (1948) Staphylokinase; an activator of plasma protease. Nature 161: 559.
232. Sakharov D V, Lijnen H R, Rijken D C (1996) Interactions between staphylokinase, plasmin(ogen), and fibrin. Staphylokinase discriminates between free plasminogen and plasminogen bound to partially degraded fibrin. The Journal of biological chemistry 271: 27912-27918.
233. Kwiecinski J, Josefsson E, Mitchell J, Higgins J, Magnusson M, et al. (2010) Activation of plasminogen by staphylokinase reduces the severity of *Staphylococcus aureus* systemic infection. The Journal of infectious diseases 202: 1041-1049.

234. Karesh A (2009) Pediatric Focused Safety Review: Argatroban. Pediatric Advisory Committee Meeting.
235. Walsh S (2010) FDA approves Pradaxa to prevent stroke in people with atrial fibrillation.
236. Rammelkamp C H (1948) Serologic Test for Staphylococcal Infections. American Journal of Medicine 4: 782-782.
237. Etz H, Minh D B, Henics T, Dryla A, Winkler B, et al. (2002) Identification of in vivo expressed vaccine candidate antigens from *Staphylococcus aureus*. Proceedings of the National Academy of Sciences of the United States of America 99: 6573-6578.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,338,298
U.S. Pat. No. 4,366,241
U.S. Pat. No. 4,472,509
U.S. Pat. No. 4,472,509
U.S. Pat. No. 4,554,101
U.S. Pat. No. 4,684,611
U.S. Pat. No. 4,748,018
U.S. Pat. No. 4,879,236
U.S. Pat. No. 4,938,948
U.S. Pat. No. 4,938,948
U.S. Pat. No. 4,952,500
U.S. Pat. No. 5,021,236
U.S. Pat. No. 5,196,066
U.S. Pat. No. 5,262,357
U.S. Pat. No. 5,302,523
U.S. Pat. No. 5,310,687
U.S. Pat. No. 5,322,783
U.S. Pat. No. 5,384,253
U.S. Pat. No. 5,464,765
U.S. Pat. No. 5,505,928
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,648,240
U.S. Pat. No. 5,656,610
U.S. Pat. No. 5,690,807
U.S. Pat. No. 5,702,932
U.S. Pat. No. 5,736,524
U.S. Pat. No. 5,741,957
U.S. Pat. No. 5,750,172
U.S. Pat. No. 5,756,687
U.S. Pat. No. 5,780,448
U.S. Pat. No. 5,789,215
U.S. Pat. No. 5,801,234
U.S. Pat. No. 5,827,690
U.S. Pat. No. 5,840,846
U.S. Pat. No. 5,871,986
U.S. Pat. No. 5,945,100
U.S. Pat. No. 5,981,274
U.S. Pat. No. 5,990,479
U.S. Pat. No. 5,994,624
U.S. Pat. No. 6,008,341
U.S. Pat. No. 6,048,616
U.S. Pat. No. 6,091,001
U.S. Pat. No. 6,274,323
U.S. Pat. No. 6,288,214
U.S. Pat. No. 6,630,307
U.S. Pat. No. 6,651,655
U.S. Pat. No. 6,756,361
U.S. Pat. No. 6,770,278
U.S. Pat. No. 6,793,923
U.S. Pat. No. 6,936,258
U.S. Patent Ser. 61/103,196
U.S. Patent Ser. 61/166,432
U.S. Patent Ser. 61/170,779
U.S. Patent Publn. 2002/0169288
U.S. Patent Publn. 20050106660
U.S. Patent Publn. 20060058510
U.S. Patent Publn. 20060088908
U.S. Patent Publn. 20100285564

Atherton et al., *Biol. of Reproduction*, 32:155-171, 1985.
Atkins et al., *Mol. Imhnmunol.*, 45:1600-1611, 2008.
Ausubel et al., In: *Current Protocols in Molecular Biology*, John, Wiley & Sons, Inc, New York, 1996.
Baba et al., *J. Bacteriol.*, 190:300-310, 2007.
Baba et al., *Lancet*, 359:1819-1827, 2002.
Barany and Merrifield, In: *The Peptides*, Gross and Meienhofer (Eds.), Academic Press, NY, 1-284, 1979.
Boucher and Corey, *Clin. Infect. Dis.*, 46(5):S344-349, 2008.
Burke et al., *J. Inf. Dis.*, 170:1110-1119, 1994.
Burman et al., *J. Biol. Chem.*, 283:17579-17593, 2008.
Campbell, In: *Monoclonal Antibody Technology, Laboratory Techniques in Biochemistry and Molecular Biology*, Burden and Von Knippenberg (Eds.), Elseview, Amsterdam, 13:71-74/75-83, 1984.
Carbonelli et al., *FEMS Microbiol. Lett.*, 177(1):75-82, 1999.
Cary et al., *Mol. Immunol.*, 36:769-776, 1999.
Chandler et al., *Proc. Natl. Acad. Sci. USA*, 94(8):3596-601, 1997.
Chen and Okayama, *Mol. Cell Biol.*, 7(8):2745-2752, 1987.
Cheng et al., *FASEB J.*, 23:3393-3404, 2009.
Cocea, *Biotechniques*, 23(5):814-816, 1997.
Cumber et al., *J. Immunology*, 149B:120-126, 1992.
de Bono et al., *J. Mol. Biol.*, 342(1):131-143, 2004.
DeDent et al., *Semin. hnmunopathol.*, 34:317-333, 2012.
Dholakia et al., *J. Biol. Chem.*, 264, 20638-20642, 1989.
Emorl and Gaynes, *Clin. Microbiol. Rev.*, 6:428-442, 1993.
Epitope Mapping Protocols In: *Methods in Molecular Biology*, Vol. 66, Morris (Ed.), 1996,
European Patent 0 216 846
European Patent 0 256 055
European Patent 0 323 997
European Patent Appln. 89303964.4
Fechheimer, et al., *Proc Natl. Acad. Sci. USA*, 84:8463-8467, 1987.
Fischetti, Clin. *Microbiol. Rev.*, 2:285-314, 1989.
Fraley et al., *Proc. Natl. Acad. Sci. USA*, 76:3348-3352, 1979.
Gefter et al., *Somatic Cell Genet.*, 3:231-236, 1977.
Goding, In: *Monoclonal Antibodies: Principles and Practice*, 2d ed., Academic Press, Orlando, Fla., pp 60-61, 71-74, 1986.
Goding, In: *Monoclonal Antibodies: Principles and Practice*, 2d ed., Academic Press, Orlando, Fla., pp 65, 66, 1986.

Goodyear and Silverman, *J. Exp. Med.*, 197:1125-1139, 2003.
Gopal, *Mol. Cell Biol.*, 5:1188-1190, 1985.
Graham and Van Der Eb, *Virology*, 52:456-467, 1973.
Harland and Weintraub, *J. Cell Biol.*, 101(3):1094-1099, 1985.
Harlow et al., *Antibodies: A Laboratory Manual*, Cold Spring Harbor Laboratory, Cold Spring Harbor, N.Y., Chapter 8, 1988.
Haupt et al., *PloS Pathog.*, 4:e1000250, 2008.
Hollingshead et al., *Infect. Inmmunun.*, 55:3237-3239, 1987.
Jones and Fischetti, *J. Exp. Med.*, 167:1114-1123, 1988.
Jones et al., *J. Exp. Med.*, 164:1226-1238, 1986.
Kaeppler et al., *Plant Cell Rep.*, 8:415-418, 1990.
Kaneda et al., *Science*, 243:375-378, 1989.
Kato et al, *J. Biol. Chem.*, 266:3361-3364, 1991.
Kennedy et al., *Proc. Natl. Acad. Sci.*, USA, 105(4):1327-1332, 2008.
Khatoon et al., *Ann. of Neurology*, 26, 210-219, 1989.
Kim et al., *FASEB J.*, 25:3605-3612, 2011.
Kim et al., *J. Exp. Med.*, 207:1863-1870, 2010a.
Kim et al., *Vaccine*, 28:6382-6392, 2010b.
King et al., *J. Biol. Chem.*, 269, 10210-10218, 1989.
Klevens et al., *JAMA*, 298:1763-1771, 2007.
Kohl et al., *Proc. Natl. Acad. Sci.*, USA, 100(4):1700-1705, 2003.
Kohler and Milstein, *Eur. J. Immunol.*, 6:511-519, 1976.
Kohler and Milstein, *Nature*, 256:495-497, 1975.
Kyte and Doolittle, *J. Mol. Biol.*, 157(1):105-132, 1982.
Lancefield, *J. Exp. Med.*, 47:91-103, 1928.
Lancefield, *J. Immunol.*, 89:307-313, 1962.
Lee, *Trends Microbiol.*, 4(4): 162-166, 1996.
Levenson et al., *Hum. Gene Ther.*, 9(8):1233-1236, 1998.
Liu et al. *Cell Mol. Biol.*, 49(2):209-216, 2003.
McCarthy and Lindsay, *BMC Microbiology*, 10:173, 2010.
Merrifield, *Science*, 232(4748):341-347, 1986.
Nicolau and Sene, *Biochim. Biophys. Acta*, 721:185-190, 1982.
Nicolau et al., *Methods Enzymol.*, 149:157-176, 1987.
Nimmerjahn and Ravetch, *Nat. Rev. Immunol.*, 8(1):34-47, 2008.
Omirulleh et al., *Plant Mol. Biol.*, 21(3):415-28, 1993.
O'Shannessy et al., *J. Immun. Meth.*, 99, 153-161, 1987.
Owens and Haley, *J. Biol. Chem.*, 259:14843-14848, 1987.
Pack et al., *Biochem.*, 31:1579-1584, 1992.
PCT Appln. PCT/US 11/42845
PCT Appln. WO 00/02523
PCT Appln. WO 00/12132
PCT Appln. WO 00/12689
PCT Appln. WO 00/15238
PCT Appln. WO 01/60852
PCT Appln. WO 2006/032472
PCT Appln. WO 2006/032475
PCT Appln. WO 2006/032500
PCT Appln. WO 2007/113222
PCT Appln. WO 2007/113223
PCT Appln. WO 2011/005341
PCT Appln. WO 94/09699
PCT Appln. WO 95/06128
PCT Appln. WO 98/57994
PCT Publn. WO 2006/056464
PCT Publn. WO 99/26299
Phillips et al., *Proc. Natl. Acad. Sci.*, USA, 78:4689-4693, 1981.
Potrykus et al., *Mol. Gen. Genet.*, 199(2):169-177, 1985.
Potter and Haley, *Methods Enzyrnol*, 91:613-633, 1983.
Rippe, et al., *Mol. Cell Biol.*, 10:689-695, 1990.
Robbins et al., *Adv. Exp. Med. Biol.*, 397:169-182, 1996.
Sambrook et at, In: *Molecular cloning*, Cold Spring Harbor Laboratory Press, Cold Spring Harbor, N.Y., 2001.
Scott et at, *J. Exp. Med.*, 164:1641-1651, 1986.
Silverman and Goodyear, *Nat. Rev. Immunol.*, 6:465-475, 2006.
Skerra, *J. Biotechnol.*, 74(4):257-75, 2001.
Skerra, *J. Mol. Recogn.*, 13:167-187, 2000.
Smith et al., *Mol. Microbiol.*, 83:789-804, 2012.
Stewart and Young, In: *Solid Phase Peptide Synthesis*, 2d. ed., Pierce Chemical Co., 1984.
Stranger-Jones et al., *Proc. Natl. Acad. Sci., USA*, 103: 16942-16947, 2006.
Tam et al., *J. Am. Chem. Soc.*, 105:6442, 1983.
Tigges et al., *J. Immunol.*, 156(10):3901-3910, 1996.
Ton-That et al., *Proc. Natl. Acad. Sci.*, USA, 96:12424-12429, 1999.
Wong et al., *Gene*, 10:87-94, 1980.
Yoo et al., *J. Immunol. Methods*, 261(1-2): 1-20, 2002.
Zhang et al., *Microbiology*, 144:985-991, 1998.
Zhang et al., *Microbiology*, 145:177-183, 1999.

The invention claimed is:

1. A method of treating Staphylococcus infection in a patient determined to have or be at risk for Staphylococcus infection comprising administering to the patient an effective amount of a composition comprising a Coa binding antibody that specifically binds to Domains 1-2 or the repeat Domain of a Staphylococcal Coa polypeptide, wherein the Coa binding antibody comprises the sequence of the six CDR domains of a 7H4.25, 4H9.20, 4B10.44, 2A3.1, 2H10.12, 6D1.22, 6C4.15, 6C10.19, 8C2.9, or 4F1.7 monoclonal antibody, wherein the 7H4.25 monoclonal antibody comprises a light chain CDR1, CDR2, and CDR3 domain with the respective sequences of QSVDYNGISY (SEQ ID NO:9), AAS (SEQ ID NO:21), and HQSIEDPRT (SEQ ID NO:30) and comprises a heavy chain CDR1, CDR2, and CDR3 domain with the respective sequences of GFNIKDIY (SEQ ID NO:12), IDPADGHS (SEQ ID NO:31), and SRSGAI (SEQ ID NO:32), wherein the 4H9.20 monoclonal antibody comprises a light chain CDR1, CDR2, and CDR3 domain with the respective sequences of QSVDYNGISY (SEQ ID NO:9), AAS (SEQ ID NO:10), and QQSIEDPRT (SEQ ID NO:11) and comprises a heavy chain CDR1, CDR2, and CDR3 domain with the respective sequences of GFNIKDIY (SEQ ID NO:12), IDPANGNT (SEQ ID NO:13), and SRSGAY (SEQ ID NO:14), wherein the 4B10.44 monoclonal antibody comprises a light chain CDR1, CDR2, and CDR3 domain with the respective sequences of QSVDYNGISY (SEQ ID NO:9), AAS (SEQ ID NO:21), and HQSIEDPRT (SEQ ID NO:22) and comprises a heavy chain CDR1, CDR2, and CDR3 domain with the respective sequences of GFNIKDIY (SEQ ID NO:12), IDPANGNT (SEQ ID NO:13), and SRSGAF (SEQ ID NO:23), wherein the 2A3.1 monoclonal antibody comprises a light chain CDR1, CDR2, and CDR3 domain with the respective sequences of QSLLNSRARKNY (SEQ ID NO:33), WAS (SEQ ID NO:34), and KQSYNLWT (SEQ ID NO:35) and comprises a heavy chain CDR1, CDR2, and CDR3 domain with the respective sequences of YTLTDYS (SEQ ID NO:37), INTETGEP (SEQ ID NO:38), and ARTARDY (SEQ ID NO:39), wherein the 2H10.12 monoclonal antibody comprises a light chain CDR1, CDR2, and CDR3 domain with the respective sequences of QSLLNSRARKNY (SEQ ID NO:40), WAS (SEQ ID NO:34), and KQSYYLWT (SEQ ID NO:36) and comprises a heavy chain CDR1, CDR2, and CDR3 domain with the respective sequences of GYTLTDYS (SEQ ID NO:41), INTETGEP (SEQ ID NO:38), and GRTARADY (SEQ ID NO:42), wherein the 6D1.22 monoclonal antibody comprises a light chain CDR1, CDR2, and CDR3 domain with the respective sequences of QSLLNSRARKNY (SEQ ID NO:40), WAS (SEQ ID NO:34), and KQSYNLWT (SEQ ID NO:35) and comprises a heavy chain CDR1, CDR2, and CDR3 domain with the respective sequences of GYTLTDYS (SEQ ID NO:41), INTETGDP (SEQ ID NO:43), and ARTARADY (SEQ ID NO:38), wherein the 6C4.15 monoclonal antibody comprises a light chain CDR1, CDR2, and CDR3 domain with the respective sequences of QSLLNSRTRKIY (SEQ ID NO:44), WAS (SEQ ID NO:34), and KQSYYLYT (SEQ ID NO:45) and comprises a heavy chain CDR1, CDR2, and CDR3domain with the respective sequences of GFSFSNYW (SEQ ID NO:46), IRLKSDNYGT (SEQ ID NO:47), and SAYGDYEY (SEQ ID NO:48), wherein the 6C10.19 monoclonal antibody comprises a light chain CDR1, CDR2, and CDR3 domain with the respective sequences of QNIVHSNGNTY (SEQ ID NO:56), KVS (SEQ ID NO:25), and LQGSNCSNH (SEQ ID NO:57) and comprises a heavy chain CDR1, CDR2, and CDR3 domain with the respective sequences of GYEFTDFE (SEQ ID NO:50), FDPETGRS (SEQ ID NO:51), and SRFHYYGRTAY (SEQ ID NO:52), wherein the 8C2.9 monoclonal antibody comprises a light chain CDR1, CDR2, and CDR3 domain with the respective sequences of QSLLNSRARKNY (SEQ ID NO:40), WAS (SEQ ID NO:34), and KQSYNLWT (SEQ ID NO:35) and comprises a heavy chain CDR1, CDR2, and CDR3 domain with the respective sequences of GFTFSNYY (SEQ ID NO:53), IKSNGVST (SEQ ID NO:54), and VRHDGYYFAY (SEQ ID NO:55), and wherein the 4F1.7 monoclonal antibody comprises a light chain CDR1, CDR2, and CDR3 domain with the respective sequences of QSLFNSRARKNY (SEQ ID NO:49), WAS (SEQ ID NO:34), and KQSYNLWT (SEQ ID NO:35) and comprises a heavy chain CDR1, CDR2, and CDR3 domain with the respective sequences of GFSIKDTT (SEQ ID NO:58), IDPTDGHN (SEQ ID NO:59), and KQSYNLWT (SEQ ID NO:60).

2. The method of claim 1, wherein the Coa binding antibody is a single chain antibody.

3. The method of claim 1, wherein the Coa binding antibody is a recombinant fusion protein.

4. The method of claim 1, wherein the Coa binding antibody comprises the sequence of the six CDR domains from the 7H4.25 monoclonal antibody.

5. The method of claim 1, wherein the Coa binding antibody is a humanized or chimeric antibody.

6. The method of claim 1, further comprising administering an antibiotic or a Staphylococcal vaccine composition.

7. A method of treating a patient having or at risk for Staphylococcus infection comprising administering to the patient an effective amount of a composition comprising a purified chimeric antibody comprising the sequence of the six CDR domains from a 7H4.25, 4H9.20, 4B10.44, 2A3.1, 2H10.12, 6D1.22, 6C4.15, 6C10.19, 8C2.9, or 4F1.7 monoclonal antibody, wherein the 7H4.25 monoclonal antibody comprises a light chain CDR1, CDR2, and CDR3 domain with the respective sequences of QSVDYNGISY (SEQ ID NO:9), AAS (SEQ ID NO:21), and HQSIEDPRT (SEQ ID NO:30) and comprises a heavy chain CDR1, CDR2, and CDR3 domain with the respective sequences of GFNIKDIY (SEQ ID NO:12), IDPADGHS (SEQ ID NO:31), and SRSGAI (SEQ ID NO:32), wherein the 4H9.20 monoclonal antibody comprises a light chain CDR1, CDR2, and CDR3 domain with the respective sequences of QSVDYNGISY (SEQ ID NO:9), AAS (SEQ ID NO:10), and QQSIEDPRT (SEQ ID NO:11) and comprises a heavy chain CDR1, CDR2, and CDR3 domain with the respective sequences of GFNIKDIY (SEQ ID NO:12), IDPANGNT (SEQ ID NO:13), and SRSGAY (SEQ ID NO:14), wherein the 4B10.44 monoclonal antibody comprises a light chain CDR1, CDR2, and CDR3 domain with the respective sequences of QSVDYNGISY (SEQ ID NO:9), AAS (SEQ ID NO:21), and HQSIEDPRT (SEQ ID NO:22) and comprises a heavy chain CDR1, CDR2, and CDR3 domain with the respective sequences of GFNIKDIY (SEQ ID NO:12), IDPANGNT (SEQ ID NO:13), and SRSGAF (SEQ ID NO:23), wherein the 2A3.1 monoclonal antibody comprises a light chain CDR1, CDR2, and CDR3 domain with the respective sequences of QSLLNSRARKNY (SEQ ID NO:33), WAS (SEQ ID NO:34), and KQSYNLWT (SEQ ID NO:35) and comprises a heavy chain CDR1, CDR2, and CDR3 domain with the respective sequences of YTLTDYS (SEQ ID NO:37), INTETGEP (SEQ ID NO:38), and ARTARDY (SEQ ID NO:39), wherein the 2H10.12 monoclonal antibody comprises a light chain CDR1, CDR2, and CDR3 domain with the respective sequences of QSLLNSRARKNY (SEQ ID NO:40), WAS (SEQ ID NO:34), and KQSYYLWT (SEQ ID NO:36) and comprises a heavy chain CDR1, CDR2, and CDR3 domain with the respective sequences of GYTLTDYS (SEQ ID NO:41), INTETGEP (SEQ ID NO:38), and GRTARADY (SEQ ID NO:42), wherein the 6D1.22 monoclonal antibody comprises a light chain CDR1, CDR2, and CDR3 domain with the respective sequences of QSLLNSRARKNY (SEQ ID NO:40), WAS (SEQ ID NO:34), and KQSYNLWT (SEQ ID NO:35) and comprises a heavy chain CDR1, CDR2, and CDR3 domain with the respective sequences of GYTLTDYS (SEQ ID NO:41), INTETGDP (SEQ ID NO:43), and ARTARADY (SEQ ID NO:38), wherein the 6C4.15 monoclonal antibody comprises a light chain CDR1, CDR2, and CDR3domain with the respective sequences of QSLLNSRTRKIY (SEQ ID NO:44), WAS (SEQ ID NO:34), and KQSYYLYT (SEQ ID NO:45) and comprises a heavy chain CDR1, CDR2, and CDR3 domain with the respective sequences of GFSFSNYW (SEQ ID NO:46), IRLKSDNYGT (SEQ ID NO:47), and SAYGDYEY (SEQ ID NO:48), wherein the 6C10.19 monoclonal antibody comprises a light chain CDR1, CDR2, and CDR3 domain with the respective sequences of QNIVHSNGNTY (SEQ ID NO:56), KVS (SEQ ID NO:25), and LQGSNCSNH (SEQ ID NO:57) and comprises a heavy chain CDR1, CDR2, and CDR3 domain with the respective sequences of GYEFTDFE (SEQ ID NO:50), FDPETGRS (SEQ ID NO:51), and SRFHYYGRTAY (SEQ ID NO:52), wherein the 8C2.9 monoclonal antibody comprises a light chain CDR1, CDR2, and CDR3 domain with the respective sequences of QSLLNSRARKNY (SEQ ID NO:40), WAS (SEQ ID NO:34), and KQSYNLWT (SEQ ID NO:35) and comprises a heavy chain CDR1, CDR2, and CDR3 domain with the respective sequences of GFTFSNYY (SEQ ID NO:53), IKSNGVST (SEQ ID NO:54), and VRHDGYYFAY (SEQ ID NO:55), and wherein the 4F1.7 monoclonal antibody comprises a light chain CDR1, CDR2, and CDR3 domain with the respective sequences of QSLFNSRARKNY (SEQ ID NO:49), WAS (SEQ ID NO:34), and KQSYNLWT (SEQ ID NO:35) and comprises a heavy chain CDR1, CDR2, and CDR3 domain with the respective sequences of GFSIKDTT (SEQ ID NO:58), IDPTDGHN (SEQ ID NO:59), and KQSYNLWT (SEQ ID NO:60).

8. The method of claim 7 wherein the purified chimeric antibody comprises the sequence of the six CDR domains of the 7H4.25 monoclonal antibody.

9. The method of claim 7 wherein the purified chimeric antibody is humanized.

10. The method of claim 7 wherein the purified chimeric antibody is recombinant.

11. The method of claim 10, wherein the recombinant chimeric antibody comprises the sequence of the six CDR domains from the 7H4.25 monoclonal antibody.

12. The method of claim 7, wherein the purified chimeric antibody is a single chain antibody.

13. The method of claim 7, further comprising administering an antibiotic or a Staphylococcal vaccine composition.

* * * * *